US012245355B2

(12) United States Patent
Zhang et al.

(10) Patent No.: US 12,245,355 B2
(45) Date of Patent: Mar. 4, 2025

(54) GANTRY FOR A PARTICLE THERAPY SYSTEM

(71) Applicant: Mevion Medical Systems, Inc., Littleton, MA (US)

(72) Inventors: Yan Zhang, Hudson, MA (US); Gerrit Townsend Zwart, Durham, NH (US); James Cooley, Boxborough, MA (US); Mark R. Jones, Bolton, MA (US); Honghai Song, Setauket, NY (US); Yan Liu, Kunshan (CN); Xunjie Yu, Southbridge, MA (US)

(73) Assignee: Mevion Medical Systems, Inc., Littleton, MA (US)

( * ) Notice: Subject to any disclaimer, the term of this patent is extended or adjusted under 35 U.S.C. 154(b) by 194 days.

(21) Appl. No.: 17/675,142

(22) Filed: Feb. 18, 2022

(65) Prior Publication Data

US 2022/0272827 A1 Aug. 25, 2022

Related U.S. Application Data

(60) Provisional application No. 63/151,281, filed on Feb. 19, 2021.

(51) Int. Cl.
*H05H 7/04* (2006.01)
*A61N 5/10* (2006.01)
(Continued)

(52) U.S. Cl.
CPC ............. *H05H 7/04* (2013.01); *A61N 5/1081* (2013.01); *G21K 1/093* (2013.01); *H05H 13/02* (2013.01); *H05H 2277/11* (2013.01)

(58) Field of Classification Search
CPC ...... H05H 7/04; H05H 13/02; H05H 2247/11; A61N 5/1081; G21K 1/093
See application file for complete search history.

(56) References Cited

U.S. PATENT DOCUMENTS

| 4,870,287 A | 9/1989 | Cole et al. |
| 5,818,058 A | 10/1998 | Nakanishi et al. |

(Continued)

FOREIGN PATENT DOCUMENTS

| EP | 1396278 | 6/2006 |
| TW | 202039026 A | 11/2020 |

OTHER PUBLICATIONS

English translation of Office Action in TW Application No. 111105938 (May 24, 2023), 2 pages.

(Continued)

*Primary Examiner* — Sean M Luck
(74) *Attorney, Agent, or Firm* — ArentFox Schiff LLP

(57) ABSTRACT

An example particle therapy system includes a gantry having a beamline structure configured to direct a particle beam that is monoenergetic from an output of a particle accelerator towards an irradiation target, where the beamline structure includes magnetic bending elements to bend the particle beam along a length of the beamline structure; and an energy degrader downstream of the beamline structure relative to the particle accelerator, where the energy degrader is configured and controllable to change an energy of the particle beam prior to at least part of the particle beam reaching the irradiation target.

32 Claims, 22 Drawing Sheets

(51) Int. Cl.
*G21K 1/093* (2006.01)
*H05H 13/02* (2006.01)

(56) References Cited

U.S. PATENT DOCUMENTS

| | | |
|---|---|---|
| 6,476,403 B1 | 11/2002 | Dolinskii et al. |
| 6,645,464 B1 | 11/2003 | Hainfeld |
| 6,678,348 B1 | 1/2004 | Kumakhov |
| 6,683,318 B1 | 1/2004 | Haberer et al. |
| 6,705,984 B1 | 3/2004 | Angha |
| 6,724,189 B2 | 4/2004 | Stern |
| 6,730,921 B2 | 5/2004 | Kraft |
| 6,783,760 B1 | 8/2004 | Thorpe et al. |
| 6,803,591 B2 | 10/2004 | Muramatsu et al. |
| 6,822,244 B2 | 11/2004 | Beloussov et al. |
| 6,822,405 B2 | 11/2004 | Jackson |
| 6,859,741 B2 | 2/2005 | Haberer et al. |
| 6,881,970 B2 | 4/2005 | Akiyama et al. |
| 6,889,695 B2 | 5/2005 | Pankratov et al. |
| 6,894,300 B2 | 5/2005 | Reimoser et al. |
| 6,897,451 B2 | 5/2005 | Kaercher et al. |
| 6,900,446 B2 | 5/2005 | Akiyama et al. |
| 6,903,351 B1 | 6/2005 | Akiyama et al. |
| 6,903,356 B2 | 6/2005 | Muramatsu et al. |
| 6,953,943 B2 | 10/2005 | Yanagisawa et al. |
| 6,955,639 B2 | 10/2005 | Hainfeld et al. |
| 6,963,072 B2 | 11/2005 | Kumakhov |
| 6,969,194 B1 | 11/2005 | Nafstadius |
| 6,979,832 B2 | 12/2005 | Yanagisawa et al. |
| 6,992,312 B2 | 1/2006 | Yanagisawa et al. |
| 7,012,267 B2 | 3/2006 | Moriyama et al. |
| 7,030,396 B2 | 4/2006 | Muramatsu et al. |
| 7,067,109 B1 | 6/2006 | Thorpe et al. |
| 7,060,997 B2 | 8/2006 | Norimine et al. |
| 7,084,410 B2 | 8/2006 | Beloussov et al. |
| 7,102,144 B2 | 9/2006 | Matsuda et al. |
| 7,122,811 B2 | 10/2006 | Matsuda et al. |
| 7,173,264 B2 | 2/2007 | Moriyama et al. |
| 7,227,161 B2 | 6/2007 | Matsuda et al. |
| 7,262,424 B2 | 8/2007 | Moriyama et al. |
| 7,276,612 B2 | 10/2007 | Verner et al. |
| 7,288,251 B2 | 10/2007 | Bedian et al. |
| 7,306,925 B2 | 12/2007 | Hallahan et al. |
| 7,319,231 B2 | 1/2008 | Moriyama et al. |
| 7,338,660 B2 | 3/2008 | Bedian et al. |
| 7,345,291 B2 | 3/2008 | Kats |
| 7,345,292 B2 | 3/2008 | Moriyama et al. |
| 7,351,988 B2 | 4/2008 | Naumann et al. |
| 7,367,934 B2 | 5/2008 | Hainfeld et al. |
| 7,368,740 B2 | 5/2008 | Beloussov et al. |
| 7,372,053 B2 | 5/2008 | Yamashita et al. |
| 7,375,357 B2 | 5/2008 | Kaufman |
| 7,378,672 B2 | 5/2008 | Harada |
| 7,381,979 B2 | 6/2008 | Yamashita et al. |
| 7,397,054 B2 | 7/2008 | Natori et al. |
| 7,398,309 B2 | 7/2008 | Baumann et al. |
| 7,402,822 B2 | 7/2008 | Guertin et al. |
| 7,402,823 B2 | 7/2008 | Guertin et al. |
| 7,402,824 B2 | 7/2008 | Guertin et al. |
| 7,420,089 B2 | 9/2008 | Verner et al. |
| 7,425,717 B2 | 9/2008 | Matsuda et al. |
| 7,449,701 B2 | 11/2008 | Fujimaki et al. |
| 7,453,076 B2 | 11/2008 | Welch et al. |
| 7,456,415 B2 | 11/2008 | Yanagisawa et al. |
| 7,465,944 B2 | 12/2008 | Ueno et al. |
| 7,473,913 B2 | 1/2009 | Hermann et al. |
| 7,482,466 B2 | 1/2009 | Verner et al. |
| 7,497,689 B2 | 3/2009 | Sommer |
| 7,517,988 B2 | 4/2009 | Verner et al. |
| 7,525,104 B2 | 4/2009 | Harada |
| 7,527,969 B2 | 5/2009 | Mather et al. |
| 7,530,940 B2 | 5/2009 | Hainfeld et al. |
| 7,531,818 B2 | 5/2009 | Brahme |
| 7,547,901 B2 | 6/2009 | Guertin et al. |
| 7,560,715 B2 | 7/2009 | Pedroni |
| 7,560,717 B2 | 7/2009 | Matsuda et al. |
| 7,563,442 B2 | 7/2009 | Bedian et al. |
| 7,579,603 B2 | 8/2009 | Birgy et al. |
| 7,579,610 B2 | 8/2009 | Grozinger et al. |
| 7,582,886 B2 | 9/2009 | Trbojevic |
| 7,586,112 B2 | 9/2009 | Chiba |
| 7,618,627 B2 | 11/2009 | Park et al. |
| 7,618,633 B2 | 11/2009 | Bedian et al. |
| 7,625,558 B2 | 12/2009 | Greene et al. |
| 7,626,012 B2 | 12/2009 | Bedian et al. |
| 7,638,779 B2 | 12/2009 | Herrmann |
| 7,640,607 B2 | 1/2010 | Guertin et al. |
| 7,645,276 B2 | 1/2010 | Pankratov et al. |
| 7,728,311 B2 | 6/2010 | Gall |
| 7,755,068 B2 | 7/2010 | Ma et al. |
| 7,755,305 B2 | 7/2010 | Umezawa et al. |
| 7,758,891 B2 | 7/2010 | Desai et al. |
| 7,763,867 B2 | 7/2010 | Birgy et al. |
| 7,763,873 B2 | 7/2010 | Flynn et al. |
| 7,780,984 B2 | 8/2010 | Desai et al. |
| 7,791,051 B2 | 9/2010 | Beloussov et al. |
| 7,801,988 B2 | 9/2010 | Baumann et al. |
| 7,812,164 B2 | 10/2010 | Austad et al. |
| 7,812,326 B2 | 10/2010 | Grozinger et al. |
| 7,816,657 B2 | 10/2010 | Hansmann et al. |
| 7,834,054 B2 | 11/2010 | Verner et al. |
| 7,848,488 B2 | 12/2010 | Mansfield |
| 7,875,868 B2 | 1/2011 | Moriyama et al. |
| 7,906,102 B2 | 3/2011 | Hallahan et al. |
| 7,907,987 B2 | 3/2011 | Dempsey |
| 7,919,092 B2 | 4/2011 | Lewicki et al. |
| 7,919,759 B2 | 4/2011 | Furukawa |
| 7,919,765 B2 | 4/2011 | Timmer |
| 7,939,809 B2 | 5/2011 | Balakin |
| 7,947,969 B2 | 5/2011 | Pu |
| 7,957,508 B2 | 6/2011 | Brooks et al. |
| 7,960,359 B2 | 6/2011 | Brown et al. |
| 7,961,844 B2 | 6/2011 | Takeda et al. |
| 7,977,648 B2 | 7/2011 | Westerly et al. |
| 7,977,657 B2 | 7/2011 | Flynn et al. |
| 7,981,889 B2 | 7/2011 | Morrison et al. |
| 7,983,380 B2 | 7/2011 | Guertin et al. |
| 7,984,715 B2 | 7/2011 | Movers |
| 7,989,785 B2 | 8/2011 | Emhofer et al. |
| 7,997,553 B2 | 8/2011 | Sloan et al. |
| 7,999,083 B2 | 8/2011 | Govindan et al. |
| 8,003,964 B2 | 8/2011 | Stark et al. |
| 8,012,945 B2 | 9/2011 | Hallahan et al. |
| 8,016,336 B2 | 9/2011 | Messinger et al. |
| 8,017,648 B2 | 9/2011 | Castro et al. |
| 8,026,371 B2 | 9/2011 | Verner et al. |
| 8,030,350 B2 | 10/2011 | Gainer et al. |
| 8,031,838 B2 | 10/2011 | Bowers et al. |
| 8,033,977 B2 | 10/2011 | Hainfeld et al. |
| 8,034,375 B2 | 10/2011 | Desai et al. |
| 8,041,008 B2 | 10/2011 | Bowers et al. |
| 8,045,678 B2 | 10/2011 | Carroll |
| 8,047,714 B2 | 11/2011 | Bowers et al. |
| 8,049,187 B2 | 11/2011 | Tachikawa et al. |
| 8,050,384 B2 | 11/2011 | Carol |
| 8,053,745 B2 | 11/2011 | Moore |
| 8,053,746 B2 | 11/2011 | Timmer et al. |
| 8,058,250 B2 | 11/2011 | Brown et al. |
| 8,063,381 B2 | 11/2011 | Tsoupas et al. |
| 8,067,748 B2 | 11/2011 | Balakin |
| 8,071,966 B2 | 12/2011 | Kaiser et al. |
| 8,076,657 B2 | 12/2011 | Mackie et al. |
| 8,080,250 B1 | 12/2011 | Govindan et al. |
| 8,083,406 B2 | 12/2011 | Bowers et al. |
| 8,089,054 B2 | 1/2012 | Balakin |
| 8,093,568 B2 | 1/2012 | Mackie |
| 8,101,933 B2 | 1/2012 | Aoi et al. |
| 8,109,865 B2 | 2/2012 | Jackson |
| 8,111,809 B2 | 2/2012 | Bowers et al. |
| 8,116,429 B2 | 2/2012 | Bowers et al. |
| 8,144,832 B2 | 3/2012 | Balakin |
| 8,145,295 B2 | 3/2012 | Boyden et al. |
| 8,153,989 B2 | 4/2012 | Tachikawa et al. |
| 8,153,990 B2 | 4/2012 | Saito |

(56) References Cited

U.S. PATENT DOCUMENTS

| | | |
|---|---|---|
| 8,154,001 B2 | 4/2012 | Flynn et al. |
| 8,160,680 B2 | 4/2012 | Boyden et al. |
| 8,164,075 B2 | 4/2012 | Jung et al. |
| 8,173,611 B2 | 5/2012 | Brown et al. |
| 8,173,981 B2 | 5/2012 | Trbojevic |
| 8,180,436 B2 | 5/2012 | Boyden et al. |
| 8,188,688 B2 | 5/2012 | Balakin |
| 8,190,233 B2 | 5/2012 | Dempsey |
| 8,193,182 B2 | 6/2012 | Ren et al. |
| 8,197,471 B1 | 6/2012 | Tersigni |
| 8,198,608 B2 | 6/2012 | Mattern |
| 8,206,713 B2 | 6/2012 | Lewicki et al. |
| 8,210,899 B2 | 7/2012 | Bush |
| 8,216,173 B2 | 7/2012 | Dacey, Jr. et al. |
| 8,221,442 B2 | 7/2012 | Domb et al. |
| 8,226,943 B2 | 7/2012 | Gurney et al. |
| 8,227,509 B2 | 7/2012 | Castro et al. |
| 8,229,072 B2 | 7/2012 | Balakin |
| 8,246,952 B2 | 8/2012 | Park et al. |
| 8,249,218 B2 | 8/2012 | Bowers et al. |
| 8,253,113 B2 | 8/2012 | Nishiuchi et al. |
| 8,254,521 B2 | 8/2012 | Brooks et al. |
| 8,254,524 B2 | 8/2012 | Bowers et al. |
| 8,257,733 B2 | 9/2012 | Desai et al. |
| 8,263,954 B2 | 9/2012 | Iwata |
| 8,268,348 B2 | 9/2012 | Desai et al. |
| 8,272,088 B2 | 9/2012 | Sliski et al. |
| 8,277,810 B2 | 10/2012 | Long et al. |
| 8,282,541 B2 | 10/2012 | Park |
| 8,282,593 B2 | 10/2012 | Dacey, Jr. et al. |
| 8,283,645 B2 | 10/2012 | Guneysel |
| 8,288,742 B2 | 10/2012 | Balakin |
| 8,298,801 B2 | 10/2012 | Kink et al. |
| 8,299,447 B2 | 10/2012 | Hagino et al. |
| 8,304,751 B2 | 11/2012 | Honda et al. |
| 8,306,184 B2 | 11/2012 | Chang et al. |
| 8,328,785 B2 | 12/2012 | Bensaoula et al. |
| 8,337,382 B2 | 12/2012 | Schneider et al. |
| 8,343,086 B2 | 1/2013 | Dacey, Jr. et al. |
| 8,344,340 B2 | 1/2013 | Gall et al. |
| 8,354,656 B2 | 1/2013 | Beloussov et al. |
| 8,357,652 B2 | 1/2013 | Liang et al. |
| 8,361,437 B2 | 1/2013 | Sharma et al. |
| 8,366,652 B2 | 2/2013 | Dacey, Jr. et al. |
| 8,372,995 B2 | 2/2013 | Krishnan et al. |
| 8,373,143 B2 | 2/2013 | Balakin |
| 8,373,145 B2 | 2/2013 | Balakin |
| 8,373,146 B2 | 2/2013 | Balakin |
| 8,374,312 B2 | 2/2013 | Mansfield |
| 8,376,013 B2 | 2/2013 | Bourke, Jr. et al. |
| 8,378,311 B2 | 2/2013 | Balakin |
| 8,378,321 B2 | 2/2013 | Balakin |
| 8,383,836 B2 | 2/2013 | Toone et al. |
| 8,384,053 B2 | 2/2013 | Balakin |
| 8,384,054 B2 | 2/2013 | Fehrenbacher et al. |
| 8,388,932 B2 | 3/2013 | Hallahan et al. |
| 8,388,971 B2 | 3/2013 | Bedian et al. |
| 8,389,570 B2 | 3/2013 | Verner et al. |
| 8,389,949 B2 | 3/2013 | Harada et al. |
| 8,394,007 B2 | 3/2013 | Henderson |
| 8,399,866 B2 | 3/2013 | Balakin |
| 8,404,237 B2 | 3/2013 | Lewicki et al. |
| 8,405,044 B2 | 3/2013 | MacKinnon |
| 8,405,056 B2 | 3/2013 | Amaldi |
| 8,410,447 B2 | 4/2013 | Tonami |
| 8,414,517 B2 | 4/2013 | Dacey, Jr. et al. |
| 8,415,455 B2 | 4/2013 | Levine et al. |
| 8,415,643 B2 | 4/2013 | Balakin |
| 8,425,903 B2 | 4/2013 | Gurney et al. |
| 8,426,833 B2 | 4/2013 | Trbojevic |
| 8,435,513 B2 | 5/2013 | Gurney et al. |
| 8,436,325 B2 | 5/2013 | Noda et al. |
| 8,436,327 B2 | 5/2013 | Balakin |
| 8,440,987 B2 | 5/2013 | Stephani et al. |
| 8,445,872 B2 | 5/2013 | Behrens |
| 8,466,428 B2 | 6/2013 | Iwata |
| 8,471,228 B2 | 6/2013 | Bert et al. |
| 8,479,743 B2 | 7/2013 | Moyers |
| 8,481,505 B2 | 7/2013 | Croce et al. |
| 8,487,282 B2 | 7/2013 | Iseki et al. |
| 8,497,480 B2 | 7/2013 | Tonami |
| 8,502,177 B2 | 8/2013 | Bert et al. |
| 8,507,734 B2 | 8/2013 | Chen et al. |
| 8,519,365 B2 | 8/2013 | Balakin |
| 8,523,630 B2 | 9/2013 | Bush |
| 8,546,769 B2 | 10/2013 | Uno |
| 8,563,708 B2 | 10/2013 | Brown et al. |
| 8,568,285 B2 | 10/2013 | Keppel et al. |
| 8,569,323 B2 | 10/2013 | Ren et al. |
| 8,569,717 B2 | 10/2013 | Balakin |
| 8,575,563 B2 | 11/2013 | Cameron et al. |
| 8,575,564 B2 | 11/2013 | Iwata |
| 8,580,312 B2 | 11/2013 | Ogino et al. |
| 8,586,941 B2 | 11/2013 | Harada et al. |
| 8,592,778 B2 | 11/2013 | Iwata |
| 8,598,543 B2 | 12/2013 | Balakin |
| 8,598,546 B2 | 12/2013 | Bert et al. |
| 8,601,116 B2 | 12/2013 | Baumann et al. |
| 8,603,521 B2 | 12/2013 | Loury et al. |
| 8,604,016 B2 | 12/2013 | Li et al. |
| 8,604,444 B2 | 12/2013 | Katayose |
| 8,614,429 B2 | 12/2013 | Balakin |
| 8,617,521 B2 | 12/2013 | Hallahan et al. |
| 8,617,522 B2 | 12/2013 | Sharma et al. |
| 8,624,528 B2 | 1/2014 | Balakin |
| 8,625,739 B2 | 1/2014 | Balakin |
| 8,627,822 B2 | 1/2014 | Balakin |
| 8,633,249 B2 | 1/2014 | Towner et al. |
| 8,637,032 B2 | 1/2014 | Long et al. |
| 8,637,839 B2 | 1/2014 | Brauer |
| 8,837,833 B1 | 1/2014 | Balakin |
| 8,642,742 B2 | 2/2014 | Hofer et al. |
| 8,642,979 B2 | 2/2014 | Gutfleisch |
| 8,644,452 B2 | 2/2014 | Carol et al. |
| 8,653,473 B2 | 2/2014 | Yajima |
| 8,658,086 B2 | 2/2014 | Bourke, Jr. et al. |
| 8,658,991 B2 | 2/2014 | Pu |
| 8,664,236 B2 | 3/2014 | Heinrich et al. |
| 8,664,620 B2 | 3/2014 | Haruna et al. |
| 8,669,365 B2 | 3/2014 | Austad et al. |
| 8,674,318 B2 | 3/2014 | Iwata |
| 8,680,132 B2 | 3/2014 | Wang et al. |
| 8,688,197 B2 | 4/2014 | Balakin |
| 8,696,658 B2 | 4/2014 | Pankratov et al. |
| 8,704,201 B2 | 4/2014 | Schippers |
| 8,709,430 B2 | 4/2014 | Thorpe et al. |
| 8,710,462 B2 | 4/2014 | Balakin |
| 8,721,660 B2 | 5/2014 | Ulfarsson et al. |
| 8,741,300 B2 | 6/2014 | Govindan et al. |
| 8,742,348 B2 | 6/2014 | Nagamine |
| 8,747,292 B2 | 6/2014 | Schneider et al. |
| 8,748,379 B2 | 6/2014 | Stout et al. |
| 8,748,446 B2 | 6/2014 | Jones et al. |
| 8,748,852 B2 | 6/2014 | Jongen |
| 8,754,124 B2 | 6/2014 | Ahn et al. |
| 8,757,877 B2 | 6/2014 | Henderson |
| 8,759,496 B2 | 6/2014 | Govindan et al. |
| 8,765,097 B2 | 7/2014 | Hallahan et al. |
| 8,765,709 B2 | 7/2014 | Brown et al. |
| 8,766,217 B2 | 7/2014 | Balakin |
| 8,766,218 B2 | 7/2014 | Jongen |
| 8,779,098 B2 | 7/2014 | Mather et al. |
| 8,779,171 B2 | 7/2014 | Verner et al. |
| 8,779,393 B2 | 7/2014 | Sasai |
| 8,784,811 B2 | 7/2014 | Lewicki et al. |
| 8,785,456 B2 | 7/2014 | Ren et al. |
| 8,785,635 B2 | 7/2014 | Austad et al. |
| 8,790,650 B2 | 7/2014 | Lee et al. |
| 8,791,275 B2 | 7/2014 | Toone et al. |
| 8,791,435 B2 | 7/2014 | Balakin |
| 8,791,437 B2 | 7/2014 | Felici et al. |
| 8,791,656 B1 | 7/2014 | Zwart et al. |
| 8,792,615 B2 | 7/2014 | Rinecker |
| 8,815,805 B2 | 8/2014 | Feng |

(56) References Cited

U.S. PATENT DOCUMENTS

| | | |
|---|---|---|
| 8,829,466 B2 | 9/2014 | Iwata |
| 8,834,883 B2 | 9/2014 | Croy et al. |
| 8,835,885 B2 | 9/2014 | Ogasawara |
| 8,836,332 B2 | 9/2014 | Shvartsman et al. |
| 8,865,718 B2 | 10/2014 | Li et al. |
| 8,872,127 B2 | 10/2014 | Okamura |
| 8,872,140 B2 | 10/2014 | Jung et al. |
| 8,878,142 B2 | 11/2014 | Sano |
| 8,884,256 B2 | 11/2014 | Sugahara et al. |
| 8,888,731 B2 | 11/2014 | Dacey, Jr. et al. |
| 8,895,509 B2 | 11/2014 | McDonald et al. |
| 8,895,575 B2 | 11/2014 | Heinrich et al. |
| 8,895,576 B2 | 11/2014 | Castro et al. |
| 8,907,109 B2 | 12/2014 | Toone et al. |
| 8,907,309 B2 | 12/2014 | Spotts |
| 8,907,311 B2 | 12/2014 | Gall et al. |
| 8,907,594 B2 | 12/2014 | Begg et al. |
| 8,911,786 B2 | 12/2014 | Desai et al. |
| 8,912,187 B2 | 12/2014 | Martin et al. |
| 8,916,545 B2 | 12/2014 | Chen et al. |
| 8,916,838 B2 | 12/2014 | Claereboudt et al. |
| 8,916,841 B2 | 12/2014 | Totake et al. |
| 8,916,843 B2 | 12/2014 | Gall et al. |
| 8,927,288 B2 | 1/2015 | Hallahan et al. |
| 8,927,615 B2 | 1/2015 | Bourke, Jr. et al. |
| 8,927,946 B2 | 1/2015 | Behrens et al. |
| 8,927,950 B2 | 1/2015 | Gall et al. |
| 8,933,421 B2 | 1/2015 | Drees et al. |
| 8,933,651 B2 | 1/2015 | Balakin et al. |
| 8,936,629 B2 | 1/2015 | Boyden et al. |
| 8,941,083 B2 | 1/2015 | Stark et al. |
| 8,945,547 B2 | 2/2015 | Gurney et al. |
| 8,945,873 B2 | 2/2015 | Gurney et al. |
| 8,945,874 B2 | 2/2015 | Gurney et al. |
| 8,946,159 B2 | 2/2015 | Feng |
| 8,946,177 B2 | 2/2015 | Brown et al. |
| 8,946,445 B2 | 2/2015 | Wang |
| 8,952,343 B2 | 2/2015 | Stephani et al. |
| 8,956,277 B2 | 2/2015 | Mishelevich |
| 8,957,393 B2 | 2/2015 | Iwata |
| 8,962,797 B2 | 2/2015 | Jones et al. |
| 8,963,108 B2 | 2/2015 | Matteo et al. |
| 8,964,936 B2 | 2/2015 | Brooks et al. |
| 8,969,291 B2 | 3/2015 | Ilan et al. |
| 8,969,834 B2 | 3/2015 | Balakin |
| 8,975,600 B2 | 3/2015 | Balakin |
| 8,975,836 B2 | 3/2015 | Bromberg et al. |
| 8,980,246 B2 | 3/2015 | Kirn |
| 8,980,260 B2 | 3/2015 | Gurney et al. |
| 8,987,224 B2 | 3/2015 | Yao et al. |
| 8,999,344 B2 | 4/2015 | Govindan et al. |
| 9,004,131 B2 | 4/2015 | Bourke, Jr. et al. |
| 9,005,406 B2 | 4/2015 | Bourke, Jr. |
| 9,006,693 B2 | 4/2015 | Sasai |
| 9,011,309 B2 | 4/2015 | Krishna et al. |
| 9,012,866 B2 | 4/2015 | Benna et al. |
| 9,018,601 B2 | 4/2015 | Balakin |
| 9,028,390 B2 | 5/2015 | Keppel et al. |
| 9,029,502 B2 | 5/2015 | Nyati et al. |
| 9,040,540 B2 | 5/2015 | Collins et al. |
| 9,040,721 B2 | 5/2015 | Jones et al. |
| 9,044,599 B2 | 6/2015 | Bert et al. |
| 9,044,600 B2 | 6/2015 | Balakin |
| 9,044,605 B2 | 6/2015 | Hori et al. |
| 9,045,474 B2 | 6/2015 | Schiestl et al. |
| 9,051,571 B2 | 6/2015 | Brown et al. |
| 9,056,199 B2 | 6/2015 | Balakin |
| 9,061,141 B2 | 6/2015 | Brunker et al. |
| 9,061,144 B2 | 6/2015 | Fujii et al. |
| 9,067,066 B2 | 6/2015 | Yamada et al. |
| 9,068,219 B2 | 6/2015 | Brown et al. |
| 9,072,705 B2 | 7/2015 | Ahn et al. |
| 9,078,856 B2 | 7/2015 | Thodeti et al. |
| 9,084,886 B2 | 7/2015 | Bush |
| 9,084,889 B2 | 7/2015 | Noda et al. |
| 9,084,890 B2 | 7/2015 | Iwata |
| 9,085,630 B2 | 7/2015 | Crowley et al. |
| 9,089,683 B2 | 7/2015 | Mishelevich |
| 9,095,612 B2 | 8/2015 | Jones et al. |
| 9,095,705 B2 | 8/2015 | Trbojevic |
| 9,101,543 B2 | 8/2015 | Desai et al. |
| 9,102,735 B2 | 8/2015 | Govindan et al. |
| 9,107,862 B2 | 8/2015 | Toporik et al. |
| 9,114,158 B2 | 8/2015 | Raman et al. |
| 9,114,253 B2 | 8/2015 | Dempsey |
| 9,132,286 B2 | 9/2015 | Henderson |
| 9,133,085 B2 | 9/2015 | Chen et al. |
| 9,138,485 B2 | 9/2015 | Govindan et al. |
| 9,139,519 B2 | 9/2015 | Scicinski et al. |
| 9,142,385 B1 | 9/2015 | Iwanaga |
| 9,145,422 B2 | 9/2015 | Castro et al. |
| 9,149,648 B2 | 10/2015 | Dacey, Jr. et al. |
| 9,150,846 B2 | 10/2015 | Jefferies et al. |
| 9,155,186 B2 | 10/2015 | Zwart et al. |
| 9,155,911 B1 | 10/2015 | Balakin |
| 9,155,912 B2 | 10/2015 | Yu |
| 9,161,810 B2 | 10/2015 | Gruber |
| 9,161,947 B2 | 10/2015 | Schaapveld et al. |
| 9,162,079 B2 | 10/2015 | Levy et al. |
| 9,162,081 B2 | 10/2015 | Hori et al. |
| 9,168,392 B1 | 10/2015 | Balakin |
| 9,169,235 B2 | 10/2015 | Martin et al. |
| 9,174,190 B2 | 11/2015 | Bourke, Jr. et al. |
| 9,175,090 B2 | 11/2015 | Lee et al. |
| 9,175,280 B2 | 11/2015 | Gregory et al. |
| 9,177,751 B2 | 11/2015 | Balakin |
| 9,180,105 B2 | 11/2015 | Frattini et al. |
| 9,185,789 B2 | 11/2015 | Zwart et al. |
| 9,186,347 B1 | 11/2015 | Verner et al. |
| 9,192,656 B2 | 11/2015 | Kink et al. |
| 9,198,941 B2 | 12/2015 | Palena et al. |
| 9,198,978 B2 | 12/2015 | Govindan et al. |
| 9,206,182 B2 | 12/2015 | Ren et al. |
| 9,206,260 B2 | 12/2015 | Hofer et al. |
| 9,207,193 B2 | 12/2015 | Censor et al. |
| 9,211,269 B2 | 12/2015 | Chen et al. |
| 9,216,982 B2 | 12/2015 | Ren et al. |
| 9,218,933 B2 | 12/2015 | Langveld et al. |
| 9,220,917 B2 | 12/2015 | Boyden et al. |
| 9,220,918 B2 | 12/2015 | Heid |
| 9,226,951 B2 | 1/2016 | Liang et al. |
| 9,226,977 B2 | 1/2016 | Kirn |
| 9,227,083 B2 | 1/2016 | Hastenteufel et al. |
| 9,232,618 B2 | 1/2016 | Bourke, Jr. et al. |
| 9,233,172 B2 | 1/2016 | Govindan et al. |
| 9,238,651 B2 | 1/2016 | Heinrich et al. |
| 9,249,114 B2 | 2/2016 | Karra et al. |
| 9,259,595 B2 | 2/2016 | Brahme et al. |
| 9,260,439 B2 | 2/2016 | Chen et al. |
| 9,278,331 B2 | 3/2016 | Bourke, Jr. et al. |
| 9,283,406 B2 | 3/2016 | Prieels |
| 9,283,407 B2 | 3/2016 | Benna et al. |
| 9,283,408 B2 | 3/2016 | Huber et al. |
| 9,289,436 B2 | 3/2016 | Szmulewitz et al. |
| 9,289,511 B2 | 3/2016 | Bianchi |
| 9,289,624 B2 | 3/2016 | Jongen |
| 9,301,384 B2 | 3/2016 | Zwart et al. |
| 9,302,116 B2 | 4/2016 | Vo-Dinh et al. |
| 9,302,120 B2 | 4/2016 | Wang et al. |
| 9,302,121 B2 | 4/2016 | Totake et al. |
| 9,302,122 B2 | 4/2016 | Balakin |
| 9,302,123 B2 | 4/2016 | Amelia |
| 9,308,218 B2 | 4/2016 | Valadkhan |
| 9,314,649 B2 | 4/2016 | Balakin |
| 9,314,944 B2 | 4/2016 | Shohat et al. |
| 9,320,813 B2 | 4/2016 | Peyman |
| 9,327,025 B2 | 5/2016 | Kazerooni et al. |
| 9,328,105 B2 | 5/2016 | Gupta |
| 9,329,462 B2 | 5/2016 | Matteo et al. |
| 9,333,211 B2 | 5/2016 | Bose et al. |
| 9,333,218 B2 | 5/2016 | Wang et al. |
| 9,340,501 B2 | 5/2016 | Li et al. |
| 9,340,581 B2 | 5/2016 | Hallahan et al. |
| 9,345,783 B2 | 5/2016 | Govindan et al. |

(56) References Cited

U.S. PATENT DOCUMENTS

| | | |
|---|---|---|
| 9,345,787 B2 | 5/2016 | Hemminki et al. |
| 9,351,691 B2 | 5/2016 | Keppel et al. |
| 9,352,040 B2 | 5/2016 | Bourke, Jr. et al. |
| 9,358,292 B2 | 6/2016 | Bourke, Jr. et al. |
| 9,359,395 B2 | 6/2016 | Casebier |
| 9,375,466 B2 | 6/2016 | Cohen-Dayag et al. |
| 9,382,537 B2 | 7/2016 | Brown et al. |
| 9,393,306 B2 | 7/2016 | You et al. |
| 9,393,318 B2 | 7/2016 | Desai et al. |
| 9,393,439 B2 | 7/2016 | Goer |
| 9,394,303 B2 | 7/2016 | Nikolovska-Coleska et al. |
| 9,399,147 B2 | 7/2016 | Haruna et al. |
| 9,402,298 B2 | 7/2016 | Sugahara et al. |
| 9,403,032 B2 | 8/2016 | Loury et al. |
| 9,403,797 B2 | 8/2016 | Collins et al. |
| 9,408,928 B2 | 8/2016 | Azhdarinia et al. |
| 9,409,040 B2 | 8/2016 | Carol et al. |
| 9,409,868 B2 | 8/2016 | Schonbrunn et al. |
| 9,421,257 B2 | 8/2016 | Iwata |
| 9,421,398 B2 | 8/2016 | Shvartsman et al. |
| 9,428,465 B2 | 8/2016 | Piomelli et al. |
| 9,433,800 B2 | 9/2016 | Levy et al. |
| 9,439,912 B2 | 9/2016 | Njar et al. |
| 9,447,414 B2 | 9/2016 | Brown et al. |
| 9,452,300 B2 | 9/2016 | Anferov |
| 9,452,301 B2 | 9/2016 | Gall et al. |
| 9,457,200 B2 | 10/2016 | Matteo et al. |
| 9,458,095 B2 | 10/2016 | Ahn et al. |
| 9,468,625 B2 | 10/2016 | Scicinski et al. |
| 9,468,777 B2 | 10/2016 | Fallone et al. |
| 9,474,748 B2 | 10/2016 | Towner et al. |
| 9,474,769 B2 | 10/2016 | Hwu et al. |
| 9,475,028 B2 | 10/2016 | Krishna et al. |
| 9,480,659 B2 | 11/2016 | Chen et al. |
| 9,480,699 B2 | 11/2016 | Croce et al. |
| 9,480,756 B2 | 11/2016 | Govindan et al. |
| 9,492,427 B2 | 11/2016 | Frattini et al. |
| 9,492,435 B2 | 11/2016 | Austad et al. |
| 9,492,684 B2 | 11/2016 | Takavanaai et al. |
| 9,493,842 B2 | 11/2016 | Giaccone et al. |
| 9,498,167 B2 | 11/2016 | Mostafavi et al. |
| 9,498,448 B2 | 11/2016 | Chen et al. |
| 9,498,643 B2 | 11/2016 | Bourke, Jr. et al. |
| 9,498,649 B2 | 11/2016 | Balakin |
| 9,499,461 B2 | 11/2016 | Chen et al. |
| 9,499,613 B2 | 11/2016 | Gurney et al. |
| 9,505,763 B2 | 11/2016 | Hong et al. |
| 9,505,832 B2 | 11/2016 | Gurney et al. |
| 9,506,061 B2 | 11/2016 | Brown et al. |
| 9,511,242 B2 | 12/2016 | Uhlemann |
| 9,512,423 B2 | 12/2016 | Stout et al. |
| 9,522,146 B2 | 12/2016 | Ren et al. |
| 9,526,463 B2 | 12/2016 | Brachman et al. |
| 9,526,913 B2 | 12/2016 | Vo-Dinh et al. |
| 9,526,914 B2 | 12/2016 | Vo-Dinh et al. |
| 9,526,915 B2 | 12/2016 | Kovach |
| 9,539,442 B2 | 1/2017 | Goebel |
| 9,543,106 B2 | 1/2017 | Balakin |
| 9,545,526 B1 | 1/2017 | Partain |
| 9,545,528 B1 | 1/2017 | Gall et al. |
| 9,546,365 B2 | 1/2017 | Yao et al. |
| 9,550,071 B2 | 1/2017 | Bensaoula et al. |
| 9,550,075 B2 | 1/2017 | Matteo et al. |
| 9,555,087 B2 | 1/2017 | Toporik et al. |
| 9,555,263 B2 | 1/2017 | Groke et al. |
| 9,556,113 B2 | 1/2017 | Guan et al. |
| 9,561,253 B2 | 2/2017 | Strober et al. |
| 9,566,276 B2 | 2/2017 | Martin et al. |
| 9,566,452 B2 | 2/2017 | Latham et al. |
| 9,566,453 B2 | 2/2017 | Tachibana |
| 9,572,881 B2 | 2/2017 | Jones et al. |
| 9,572,999 B2 | 2/2017 | Dempsey |
| 9,574,007 B2 | 2/2017 | Mather et al. |
| 9,579,337 B2 | 2/2017 | Stover et al. |
| 9,579,525 B2 | 2/2017 | Balakin |
| 9,580,372 B2 | 2/2017 | Chen et al. |
| 9,597,409 B2 | 3/2017 | Desai et al. |
| 9,608,395 B2 | 3/2017 | Overweg |
| 9,616,251 B2 | 4/2017 | Filiberti et al. |
| 9,616,252 B2 | 4/2017 | Balakin |
| 9,617,336 B2 | 4/2017 | Cojocaru et al. |
| 9,622,335 B2 | 4/2017 | Gall et al. |
| 9,623,097 B2 | 4/2017 | Palena et al. |
| 9,629,812 B2 | 4/2017 | Medarova et al. |
| 9,629,930 B2 | 4/2017 | Gregory et al. |
| 9,630,021 B2 | 4/2017 | Jackson |
| 9,630,022 B2 | 4/2017 | Bourke, Jr. et al. |
| RE46,383 E | 5/2017 | Jackson |
| 9,636,524 B2 | 5/2017 | Pantell et al. |
| 9,636,525 B1 | 5/2017 | Sahadevan |
| 9,649,298 B2 | 5/2017 | Djonov et al. |
| 9,649,510 B2 | 5/2017 | Balakin |
| 9,655,892 B2 | 5/2017 | Ren et al. |
| 9,656,098 B2 | 5/2017 | Goer |
| 9,661,736 B2 | 5/2017 | O'Neal, III et al. |
| 9,662,512 B2 | 5/2017 | Vahala et al. |
| 9,663,428 B2 | 5/2017 | Chen et al. |
| 9,666,320 B2 | 5/2017 | Miura et al. |
| 9,669,011 B2 | 6/2017 | Castro et al. |
| 9,669,049 B2 | 6/2017 | Gruber et al. |
| 9,675,571 B2 | 6/2017 | Balog et al. |
| 9,675,706 B2 | 6/2017 | Govindan et al. |
| 9,676,865 B2 | 6/2017 | Lewicki et al. |
| 9,681,531 B2 | 6/2017 | Gall et al. |
| 9,682,146 B2 | 6/2017 | Bourke, Jr. et al. |
| 9,682,247 B2 | 6/2017 | Susedik et al. |
| 9,682,250 B2 | 6/2017 | Bourke, Jr. et al. |
| 9,682,254 B2 | 6/2017 | Balakin |
| 9,687,485 B2 | 6/2017 | Steggerda et al. |
| 9,687,668 B2 | 6/2017 | McKenna et al. |
| 9,687,670 B2 | 6/2017 | Dacey, Jr. et al. |
| 9,694,048 B2 | 7/2017 | Bauzon et al. |
| 9,700,524 B2 | 7/2017 | Chen et al. |
| 9,700,621 B2 | 7/2017 | Levy et al. |
| 9,700,634 B2 | 7/2017 | Govindan et al. |
| 9,706,636 B2 | 7/2017 | Zwart et al. |
| 9,711,254 B2 | 7/2017 | Bromberg et al. |
| 9,717,781 B2 | 8/2017 | Shneider et al. |
| 9,718,888 B2 | 8/2017 | Magliery et al. |
| 9,723,705 B2 | 8/2017 | Gall et al. |
| 9,725,520 B2 | 8/2017 | Zhang et al. |
| 9,730,308 B2 | 8/2017 | Zwart et al. |
| 9,731,013 B2 | 8/2017 | Krishna et al. |
| 9,737,272 B2 | 8/2017 | Lee et al. |
| 9,737,731 B2 | 8/2017 | Balakin |
| 9,737,733 B2 | 8/2017 | Lee et al. |
| 9,737,734 B2 | 8/2017 | Michaud et al. |
| 9,744,380 B2 | 8/2017 | Michaud et al. |
| 9,745,314 B2 | 8/2017 | Wang et al. |
| 9,750,957 B2 | 9/2017 | Fujii et al. |
| 9,757,590 B2 | 9/2017 | Hiramoto et al. |
| 9,757,592 B2 | 9/2017 | Benna et al. |
| 9,757,594 B2 | 9/2017 | Balakin |
| 9,757,952 B2 | 9/2017 | Tanaka et al. |
| 9,763,891 B2 | 9/2017 | Medarova et al. |
| 9,764,005 B2 | 9/2017 | Liang et al. |
| 9,765,059 B2 | 9/2017 | Collins et al. |
| 9,770,604 B2 | 9/2017 | Iwata |
| 9,782,140 B2 | 10/2017 | Michaud et al. |
| 9,782,386 B2 | 10/2017 | Frattini et al. |
| 9,782,606 B2 | 10/2017 | Park et al. |
| 9,783,550 B2 | 10/2017 | Lum et al. |
| 9,786,054 B2 | 10/2017 | Taguchi et al. |
| 9,789,335 B2 | 10/2017 | Kumada et al. |
| 9,789,343 B2 | 10/2017 | Amelia et al. |
| 9,801,893 B2 | 10/2017 | Szmulewitz et al. |
| 9,808,447 B2 | 11/2017 | Schonbrunn et al. |
| 9,809,574 B2 | 11/2017 | Davidson et al. |
| 9,821,173 B2 | 11/2017 | Berdis |
| 9,839,690 B2 | 12/2017 | You et al. |
| 9,839,794 B2 | 12/2017 | Kato |
| 9,844,684 B2 | 12/2017 | Luan et al. |
| 9,850,472 B2 | 12/2017 | Vitalis et al. |
| 9,855,444 B2 | 1/2018 | Penfold et al. |

(56) References Cited

U.S. PATENT DOCUMENTS

| | | |
|---|---|---|
| 9,855,445 B2 | 1/2018 | Mansfield |
| 9,868,747 B2 | 1/2018 | Li et al. |
| 9,873,003 B2 | 1/2018 | Tsunoo et al. |
| 9,881,711 B2 | 1/2018 | Odawara et al. |
| 9,884,067 B2 | 2/2018 | Njar et al. |
| 9,889,092 B2 | 2/2018 | Corbin |
| 9,889,319 B2 | 2/2018 | Sakamoto et al. |
| 9,899,112 B2 | 2/2018 | Takayanagi et al. |
| 9,907,978 B2 | 3/2018 | Pankratov et al. |
| 9,907,981 B2 | 3/2018 | Michaud et al. |
| 9,919,062 B2 | 3/2018 | Kirn |
| 9,925,395 B2 | 3/2018 | Gall et al. |
| 9,927,805 B2 | 3/2018 | Ju |
| 9,931,522 B2 | 4/2018 | Bharadwaj et al. |
| 9,937,136 B2 | 4/2018 | Barak |
| 9,937,269 B2 | 4/2018 | Stout et al. |
| 9,937,360 B1 | 4/2018 | Papeer et al. |
| 9,937,362 B2 | 4/2018 | Lee et al. |
| 9,937,363 B2 | 4/2018 | Takizawa et al. |
| 9,938,267 B2 | 4/2018 | Li et al. |
| 9,943,570 B2 | 4/2018 | Androutsellis-Theotokis |
| 9,943,598 B2 | 4/2018 | Kysela |
| 9,944,932 B2 | 4/2018 | Schaapveld et al. |
| 9,950,067 B2 | 4/2018 | Gainer et al. |
| 9,951,083 B2 | 4/2018 | Austad et al. |
| 9,962,560 B2 | 5/2018 | Zwart et al. |
| 9,962,562 B2 | 5/2018 | Fahrig et al. |
| 9,968,569 B2 | 5/2018 | Towner et al. |
| 9,974,494 B2 | 5/2018 | Mostafavi et al. |
| 9,974,496 B2 | 5/2018 | Liu et al. |
| 9,974,807 B2 | 5/2018 | Strober et al. |
| 9,974,978 B2 | 5/2018 | Lee et al. |
| 9,974,980 B2 | 5/2018 | Liu et al. |
| 9,977,138 B2 | 5/2018 | Kunimoto |
| 9,981,147 B2 | 5/2018 | Lee et al. |
| 9,983,194 B2 | 5/2018 | Bar-Sagi et al. |
| 9,987,237 B2 | 6/2018 | Chen et al. |
| 9,987,270 B1 | 6/2018 | Oronsky et al. |
| 9,988,452 B2 | 6/2018 | Freeman et al. |
| 9,993,663 B2 | 6/2018 | Sabczynski et al. |
| 10,000,575 B2 | 6/2018 | Birkle et al. |
| 10,004,805 B2 | 6/2018 | Chen |
| 10,004,920 B2 | 6/2018 | Aoki |
| 10,016,617 B2 | 7/2018 | Mason et al. |
| 10,016,623 B2 | 7/2018 | Claereboudt et al. |
| 10,029,117 B2 | 7/2018 | Bourke, Jr. et al. |
| 10,029,124 B2 | 7/2018 | Lee et al. |
| 10,035,025 B2 | 7/2018 | Wang et al. |
| 10,037,863 B2 | 7/2018 | Amato et al. |
| 10,039,935 B1 | 8/2018 | Papeer et al. |
| 10,045,970 B2 | 8/2018 | Castro et al. |
| 10,046,022 B2 | 8/2018 | Baileykobayashi et al. |
| 10,047,401 B2 | 8/2018 | Harris et al. |
| 10,052,498 B2 | 8/2018 | Jongen et al. |
| 10,064,957 B2 | 9/2018 | Govindan et al. |
| 10,071,263 B1 | 9/2018 | Prince et al. |
| 10,076,542 B2 | 9/2018 | Strober et al. |
| 10,076,675 B2 | 9/2018 | Johnstone et al. |
| 10,080,275 B2 | 9/2018 | Bourke, Jr. et al. |
| 10,085,699 B2 | 10/2018 | Brachman et al. |
| 10,086,073 B2 | 10/2018 | Hallahan et al. |
| 10,086,214 B2 | 10/2018 | Balakin |
| 10,092,562 B2 | 10/2018 | Chen et al. |
| 10,092,645 B2 | 10/2018 | Stewart et al. |
| 10,092,775 B2 | 10/2018 | Uhlemann et al. |
| 10,092,776 B2 | 10/2018 | Michaud et al. |
| 10,093,745 B2 | 10/2018 | Morrison et al. |
| 10,098,934 B2 | 10/2018 | Levine et al. |
| 10,099,069 B2 | 10/2018 | Partanen et al. |
| 10,099,070 B2 | 10/2018 | Mougenot |
| 10,105,552 B2 | 10/2018 | Loury et al. |
| 10,112,060 B2 | 10/2018 | Lee et al. |
| 10,117,320 B2 | 10/2018 | Aoki et al. |
| 10,118,052 B2 | 11/2018 | Spotts et al. |
| 10,123,992 B2 | 11/2018 | Frattini et al. |
| 10,124,191 B2 | 11/2018 | Debatty et al. |
| 10,137,316 B2 | 11/2018 | Balakin |
| 10,143,436 B2 | 12/2018 | Nishimura et al. |
| 10,143,854 B2 | 12/2018 | Michaud et al. |
| 10,143,856 B2 | 12/2018 | Siljamäki et al. |
| 10,155,123 B2 | 12/2018 | Mukawa et al. |
| 10,155,124 B2 | 12/2018 | Gall et al. |
| 10,157,693 B2 | 12/2018 | Liu et al. |
| 10,159,694 B2 | 12/2018 | Strober et al. |
| 10,166,408 B2 | 1/2019 | Michaud et al. |
| 10,179,248 B2 | 1/2019 | Asao |
| 10,179,250 B2 | 1/2019 | Ruebel et al. |
| 10,180,505 B2 | 1/2019 | Censor et al. |
| 10,183,043 B2 | 1/2019 | Strober et al. |
| 10,188,356 B2 | 1/2019 | Guertin et al. |
| 10,188,875 B2 | 1/2019 | Kwak et al. |
| 10,188,877 B2 | 1/2019 | Lee et al. |
| 10,195,461 B2 | 2/2019 | Fuentes |
| 10,199,148 B2 | 2/2019 | Otani et al. |
| 10,201,796 B2 | 2/2019 | Bourke, Jr. et al. |
| 10,208,012 B2 | 2/2019 | Ford, Jr. et al. |
| 10,213,624 B2 | 2/2019 | Lee et al. |
| 10,213,625 B2 | 2/2019 | Goebel |
| 10,213,626 B2 | 2/2019 | Balakin et al. |
| 10,213,763 B2 | 2/2019 | Bourke, Jr. et al. |
| 10,231,679 B2 | 3/2019 | Worstell |
| 10,231,680 B2 | 3/2019 | Coppens et al. |
| 10,232,010 B2 | 3/2019 | Gelder et al. |
| 10,239,871 B2 | 3/2019 | Gupta |
| 10,254,739 B2 | 4/2019 | Jones et al. |
| 10,256,004 B2 | 4/2019 | Takayama et al. |
| 10,258,648 B2 | 4/2019 | Strober et al. |
| 10,258,810 B2 | 4/2019 | Zwart et al. |
| 10,259,846 B2 | 4/2019 | Su et al. |
| 10,260,103 B2 | 4/2019 | Gonzalez Diaz et al. |
| 10,265,414 B2 | 4/2019 | Govindan et al. |
| 10,265,510 B2 | 4/2019 | Harel et al. |
| 10,266,490 B2 | 4/2019 | Rosen et al. |
| 10,279,198 B2 | 5/2019 | Lee et al. |
| 10,279,199 B2 | 5/2019 | Gall et al. |
| 10,292,956 B2 | 5/2019 | Serrano-Ojeda |
| 10,300,076 B2 | 5/2019 | Szmulewitz et al. |
| 10,306,745 B2 | 5/2019 | Aoki et al. |
| 10,307,616 B2 | 6/2019 | Vahala et al. |
| 10,307,618 B2 | 6/2019 | Mansfield |
| 10,314,827 B2 | 6/2019 | Castro et al. |
| 10,322,051 B2 | 6/2019 | Arimura et al. |
| 10,322,193 B1 | 6/2019 | Govindan et al. |
| 10,342,778 B1 | 7/2019 | Oronsky et al. |
| 10,349,906 B2 | 7/2019 | Bennett et al. |
| 10,357,566 B2 | 7/2019 | Wheeler et al. |
| 10,357,665 B2 | 7/2019 | Ju et al. |
| 10,357,666 B2 | 7/2019 | Lee et al. |
| 10,358,454 B2 | 7/2019 | Li et al. |
| 10,358,501 B2 | 7/2019 | Zhang et al. |
| 10,363,294 B2 | 7/2019 | Palena et al. |
| 10,363,310 B2 | 7/2019 | Chen |
| 10,363,438 B2 | 7/2019 | Nagamoto et al. |
| 10,363,541 B2 | 7/2019 | Bourke, Jr. et al. |
| 10,368,429 B2 | 7/2019 | Gall et al. |
| 10,376,713 B2 | 8/2019 | Takayanagi et al. |
| 10,376,717 B2 | 8/2019 | Bennett et al. |
| 10,378,060 B2 | 8/2019 | DePinho et al. |
| 10,381,195 B2 | 8/2019 | Kamiguchi |
| 10,384,071 B2 | 8/2019 | Vo-Dinh et al. |
| 10,385,400 B2 | 8/2019 | Zhu et al. |
| 10,390,877 B2 | 8/2019 | Heggeness et al. |
| 10,391,056 B2 | 8/2019 | Kan et al. |
| 10,391,172 B2 | 8/2019 | Petit et al. |
| 10,391,174 B2 | 8/2019 | Levy et al. |
| 10,391,330 B2 | 8/2019 | Bourke, Jr. et al. |
| 10,395,881 B2 | 8/2019 | Papeer et al. |
| 10,398,014 B2 | 8/2019 | Ishida |
| 10,398,659 B2 | 9/2019 | Towner et al. |
| 10,398,777 B2 | 9/2019 | Bourke, Jr. et al. |
| 10,406,139 B2 | 9/2019 | Austad et al. |
| 10,413,751 B2 | 9/2019 | Dempsey et al. |
| 10,417,390 B2 | 9/2019 | Svatos et al. |
| 10,418,141 B2 | 9/2019 | Kamiguchi |

(56) References Cited

U.S. PATENT DOCUMENTS

| | | |
|---|---|---|
| 10,420,959 B2 | 9/2019 | Murakami et al. |
| 10,426,977 B2 | 10/2019 | Stacey et al. |
| 10,428,050 B2 | 10/2019 | Lee et al. |
| 10,429,826 B2 | 10/2019 | Ju |
| 10,434,331 B2 | 10/2019 | O'Neal, III et al. |
| 10,434,333 B2 | 10/2019 | Liu et al. |
| 10,434,337 B2 | 10/2019 | Hanada et al. |
| 10,441,226 B2 | 10/2019 | Guertin et al. |
| 10,441,810 B2 | 10/2019 | Oldham et al. |
| 10,441,816 B2 | 10/2019 | Liu et al. |
| 10,449,192 B2 | 10/2019 | Martin et al. |
| 10,449,385 B2 | 10/2019 | Ju et al. |
| 10,453,642 B2 | 10/2019 | Kim et al. |
| 10,456,468 B2 | 10/2019 | Unger |
| 10,456,591 B2 | 10/2019 | Zwart et al. |
| 10,456,600 B2 | 10/2019 | Owens et al. |
| 10,456,602 B2 | 10/2019 | Ebina et al. |
| 10,457,618 B2 | 10/2019 | Chen et al. |
| 10,457,642 B2 | 10/2019 | Pryma et al. |
| 10,463,627 B2 | 11/2019 | Medarova et al. |
| 10,463,881 B2 | 11/2019 | Gerbershagen et al. |
| 10,463,883 B2 | 11/2019 | Shvartsman et al. |
| 10,465,009 B2 | 11/2019 | Armitage et al. |
| 10,478,641 B2 | 11/2019 | Kaneko et al. |
| 10,485,994 B2 | 11/2019 | Kumata et al. |
| 10,485,995 B2 | 11/2019 | Anferov et al. |
| 10,493,296 B2 | 12/2019 | Vo-Dinh et al. |
| 10,507,339 B2 | 12/2019 | Filiberti et al. |
| 10,518,109 B2 | 12/2019 | Reno et al. |
| 10,525,281 B2 | 1/2020 | Fukumoto et al. |
| 10,532,225 B2 | 1/2020 | Kwak et al. |
| 10,532,226 B2 | 1/2020 | Desimone et al. |
| 10,532,227 B2 | 1/2020 | Takizawa et al. |
| 10,532,228 B2 | 1/2020 | Petterson et al. |
| 10,532,229 B2 | 1/2020 | Timmer et al. |
| 10,543,208 B2 | 1/2020 | Oronsky et al. |
| 10,543,380 B2 | 1/2020 | Uhlemann et al. |
| 10,548,212 B2 | 1/2020 | Aoki et al. |
| 10,548,551 B2 | 2/2020 | Lee et al. |
| 10,549,082 B2 | 2/2020 | Lowsky et al. |
| 10,549,124 B2 | 2/2020 | Lee et al. |
| 10,555,710 B2 | 2/2020 | Bennett et al. |
| 10,555,936 B2 | 2/2020 | Baskin et al. |
| 10,556,126 B2 | 2/2020 | Amato et al. |
| 10,556,127 B2 | 2/2020 | Liu |
| 10,556,131 B2 | 2/2020 | Hori et al. |
| 10,561,738 B2 | 2/2020 | Govindan et al. |
| 10,561,746 B2 | 2/2020 | Andresen et al. |
| 10,566,102 B2 | 2/2020 | Kamiguchi |
| 10,566,121 B2 | 2/2020 | Radovinsky et al. |
| 10,570,204 B2 | 2/2020 | Johnson et al. |
| 10,576,303 B2 | 3/2020 | Bharadwaj et al. |
| 10,586,678 B2 | 3/2020 | Caspi et al. |
| 10,589,128 B2 | 3/2020 | Michaud et al. |
| 10,596,387 B2 | 3/2020 | Walder et al. |
| 10,603,340 B2 | 3/2020 | Strober et al. |
| 10,603,510 B2 | 3/2020 | Nelson et al. |
| 10,603,516 B2 | 3/2020 | Pantell et al. |
| 10,603,518 B2 | 3/2020 | Hassan et al. |
| 10,604,568 B2 | 3/2020 | Sahin et al. |
| 10,605,928 B2 | 3/2020 | Ueno et al. |
| 10,609,806 B2 | 3/2020 | Roecken et al. |
| 10,617,723 B2 | 4/2020 | Saha et al. |
| 10,622,114 B2 | 4/2020 | Purwar et al. |
| 10,625,094 B2 | 4/2020 | Van Voorst et al. |
| 10,625,097 B2 | 4/2020 | Reno et al. |
| 10,638,988 B2 | 5/2020 | Penfold et al. |
| 10,639,499 B2 | 5/2020 | Liu et al. |
| 10,643,761 B2 | 5/2020 | Liu et al. |
| 10,646,570 B2 | 5/2020 | Xie et al. |
| 10,646,728 B2 | 5/2020 | Zwart et al. |
| 10,653,892 B2 | 5/2020 | Jones et al. |
| 10,675,487 B2 | 6/2020 | Zwart et al. |
| 10,682,529 B2 | 6/2020 | Schneider et al. |
| 10,682,624 B2 | 6/2020 | Bourke, Jr. et al. |
| 10,684,380 B2 | 6/2020 | Lee et al. |
| 10,688,125 B2 | 6/2020 | Golding et al. |
| 10,688,318 B2 | 6/2020 | Ie et al. |
| 10,688,319 B2 | 6/2020 | Dempsey |
| 10,689,364 B2 | 6/2020 | Davidson et al. |
| 10,695,587 B2 | 6/2020 | Yamashita et al. |
| 10,716,837 B2 | 7/2020 | Shneider et al. |
| 10,716,954 B2 | 7/2020 | Goebel et al. |
| 10,717,062 B2 | 7/2020 | Bourke, Jr. et al. |
| 10,722,555 B2 | 7/2020 | Feng |
| 10,722,735 B2 | 7/2020 | Gall et al. |
| 10,722,736 B2 | 7/2020 | Hassan et al. |
| 10,723,797 B2 | 7/2020 | Ilan et al. |
| 10,729,699 B2 | 8/2020 | Szmulewitz et al. |
| 10,729,921 B2 | 8/2020 | Schippers |
| 10,736,886 B2 | 8/2020 | Aftab et al. |
| 10,737,121 B2 | 8/2020 | Piestrup et al. |
| 10,744,345 B2 | 8/2020 | Liu |
| 10,744,346 B2 | 8/2020 | Brodrick |
| 10,751,551 B2 | 8/2020 | Bennett et al. |
| 10,751,553 B2 | 8/2020 | Ueno et al. |
| 10,751,554 B2 | 8/2020 | Penfold et al. |
| 10,751,555 B2 | 8/2020 | Raymond et al. |
| 10,751,937 B2 | 8/2020 | Yamaguchi et al. |
| 10,757,799 B2 | 8/2020 | Hori et al. |
| 10,758,127 B2 | 9/2020 | Patch |
| 10,765,387 B2 | 9/2020 | Kobayashi et al. |
| 10,773,098 B2 | 9/2020 | Liu et al. |
| 10,773,104 B2 | 9/2020 | Liu |
| 10,780,164 B2 | 9/2020 | Wu et al. |
| 10,786,689 B2 | 9/2020 | Zwart et al. |
| 10,792,511 B2 | 10/2020 | Pankratov et al. |
| 10,792,517 B2 | 10/2020 | Lee et al. |
| 10,799,714 B2 | 10/2020 | Jongen |
| 10,799,721 B2 | 10/2020 | Nagamoto et al. |
| 10,799,722 B2 | 10/2020 | Piestrup et al. |
| 10,806,409 B2 | 10/2020 | Kruesi et al. |
| 10,806,801 B2 | 10/2020 | Su et al. |
| 10,806,950 B2 | 10/2020 | Fahrig et al. |
| 10,821,102 B2 | 11/2020 | Castro et al. |
| 10,821,301 B2 | 11/2020 | Nishio et al. |
| 10,822,427 B2 | 11/2020 | Morrison et al. |
| 10,843,011 B2 | 11/2020 | Trail et al. |
| 10,850,122 B2 | 12/2020 | Luan et al. |
| 10,850,127 B2 | 12/2020 | Overweg |
| 10,850,130 B2 | 12/2020 | Piestrup et al. |
| 10,850,131 B2 | 12/2020 | Piestrup et al. |
| 10,850,132 B2 | 12/2020 | Ebina |
| 10,851,165 B2 | 12/2020 | Freeman et al. |
| 10,857,390 B2 | 12/2020 | Robar |
| 10,864,272 B2 | 12/2020 | Makale et al. |
| 10,864,384 B2 | 12/2020 | Huggins et al. |
| 10,870,020 B2 | 12/2020 | Piestrup et al. |
| 10,874,878 B2 | 12/2020 | Brusasco |
| 10,874,881 B2 | 12/2020 | Piestrup et al. |
| 10,874,882 B2 | 12/2020 | Lee et al. |
| 10,880,983 B2 | 12/2020 | Bortfeld et al. |
| 10,881,881 B2 | 1/2021 | Nonaka et al. |
| 10,894,075 B2 | 1/2021 | Bauzon et al. |
| 10,898,731 B2 | 1/2021 | Liu et al. |
| 10,898,732 B2 | 1/2021 | Petterson et al. |
| 10,898,733 B2 | 1/2021 | Liu et al. |
| 10,899,691 B2 | 1/2021 | Chen et al. |
| 10,910,188 B2 | 2/2021 | Star-Lack et al. |
| 10,918,887 B2 | 2/2021 | Shvartsman et al. |
| 10,919,979 B2 | 2/2021 | Magliery et al. |
| 10,925,147 B2 | 2/2021 | Cooley et al. |
| 10,925,926 B2 | 2/2021 | Bauzon et al. |
| 10,926,103 B2 | 2/2021 | Cruz |
| 10,926,110 B2 | 2/2021 | Liu et al. |
| 10,940,217 B2 | 3/2021 | Cormode et al. |
| 10,945,965 B2 | 3/2021 | Pottier et al. |
| 10,946,097 B2 | 3/2021 | Unger |
| 10,946,218 B2 | 3/2021 | Vahala et al. |
| 10,946,220 B2 | 3/2021 | Swerdloff |
| 10,960,229 B2 | 3/2021 | Ni et al. |
| 10,960,231 B2 | 3/2021 | Mansfield |
| RE48,526 E | 4/2021 | Yabe et al. |
| 10,967,201 B2 | 4/2021 | Ueno et al. |

(56) References Cited

U.S. PATENT DOCUMENTS

| | | |
|---|---|---|
| 10,974,077 B2 | 4/2021 | Guha et al. |
| 10,980,892 B2 | 4/2021 | Castaigne et al. |
| 10,984,935 B2 | 4/2021 | Zheng et al. |
| 10,993,680 B2 | 5/2021 | Ruebel et al. |
| 10,994,154 B2 | 5/2021 | Liu |
| 11,000,696 B2 | 5/2021 | Elgart et al. |
| 11,000,705 B2 | 5/2021 | Lee et al. |
| 11,007,181 B2 | 5/2021 | Austad et al. |
| 11,007,220 B2 | 5/2021 | Strober et al. |
| 11,008,573 B2 | 5/2021 | Yao et al. |
| 11,013,804 B2 | 5/2021 | Chen et al. |
| 11,020,428 B2 | 6/2021 | Strober et al. |
| 11,020,489 B2 | 6/2021 | Govindan et al. |
| 11,026,320 B1 | 6/2021 | Furukawa et al. |
| 11,026,647 B2 | 6/2021 | Bennett et al. |
| 11,028,070 B2 | 6/2021 | Davidson et al. |
| 11,033,758 B2 | 6/2021 | Dempsey et al. |
| 11,034,580 B2 | 6/2021 | Ostrovska |
| 11,040,067 B2 | 6/2021 | Strober et al. |
| 11,045,446 B2 | 6/2021 | Frattini et al. |
| 11,045,664 B2 | 6/2021 | Arai et al. |
| 11,058,899 B1 | 7/2021 | Furukawa et al. |
| 11,291,861 B2 | 4/2022 | Cooley et al. |
| 2006/0145088 A1* | 7/2006 | Ma ............ H05H 15/00 250/396 ML |
| 2006/0273264 A1 | 12/2006 | Nakayama et al. |
| 2007/0262269 A1 | 11/2007 | Trbojevic |
| 2008/0315113 A1 | 12/2008 | Diehl et al. |
| 2009/0090871 A1 | 4/2009 | Diehl et al. |
| 2009/0101832 A1 | 4/2009 | Diehl et al. |
| 2010/0051833 A1 | 3/2010 | Guertin et al. |
| 2011/0101236 A1 | 5/2011 | Cameron et al. |
| 2012/0280150 A1 | 11/2012 | Jongen |
| 2013/0001432 A1 | 1/2013 | Jongen |
| 2013/0187060 A1 | 7/2013 | Jongen |
| 2014/0088336 A1 | 3/2014 | Hagino et al. |
| 2014/0371511 A1 | 12/2014 | Zwart et al. |
| 2015/0087887 A1 | 3/2015 | Iwata |
| 2015/0352372 A1 | 12/2015 | Takayanagi et al. |
| 2016/0030769 A1 | 2/2016 | Cameron et al. |
| 2017/0128746 A1 | 5/2017 | Zwart et al. |
| 2017/0368373 A1* | 12/2017 | Sahadevan ............ A61N 5/1067 |
| 2017/0372867 A1 | 12/2017 | Caspi et al. |
| 2018/0178038 A1 | 6/2018 | Anferov et al. |
| 2018/0256919 A1 | 9/2018 | Shen |
| 2020/0002980 A1 | 1/2020 | Ketels et al. |
| 2020/0303165 A1 | 9/2020 | Kamiguchi |
| 2020/0306561 A1 | 10/2020 | Huggins et al. |
| 2020/0306562 A1 | 10/2020 | Godeke et al. |

OTHER PUBLICATIONS

File History of U.S. Appl. No. 16/370,145, 337 pages.
Written Opinion of the International Preliminary Examining Authority for International Application No. PCT/US2022/016928, issued Oct. 24, 2022, (12 pages).
Pedroni, Eros. A Novel Gantry for Proton Therapy at the Paul Scherrer Institute. CP600, Cyclotrons and Their Applications 2001, Sixteenth International Conference, American Institute of Physics, (May 1, 2001), p. 13-17. (5 pages).
Levichev, E.B., Carbon Ion Accelerator Facility for Cancer Therapy. Proceedings of RuPAC 2006, Novosibirsk, Russia, (2006), p. 363-365. (3 pages).
Gantry 1. Paul Scherrer Institute Center for Proton Therapy, Switzerland, (1990) (2 pages), https://www.psi.ch/en/protontherapy/gantry-1.
Pedroni, Eros. (Apr. 20, 2009). Gantry Design and Experience at PSI [Workshop on Hadron Beam Therapy of Cancer Erice]. Paul Scherrer Institute Center for Proton Therapy, Switzerland, (36 pages).
Pedroni, Eros. (May 19, 2008), Proton Beam Delivery Technique and Commissioning Issues: Scanned Protons [PTCOG Educational meeting Jacksonville]. Paul Scherrer Institute Center for Proton Therapy, Switzerland, (36 pages).
Pedroni, Eros. Beam optics design of compact gantry for proton therapy. Med Biol Eng Comput. May 1995;33(3):271-7. doi: 10.1007/BF02510499. PMID: 7475362, (7 pages).
Trbojevic, D. "Superconducting non-scaling FFAG gantry for carbon/proton cancer therapy," 2007 IEEE Particle Accelerator Conference (PAC), 2007, pp. 3199-3201, doi: 10.1109/PAC.2007.4440714.
Chen, Yu-Jiuan. Compact Proton Accelerator for Cancer Therapy. Lawrence Livermore National Laboratory, Proceedings of PAC07, Albuquerque, New Mexico, (2007), p. 1787-1789. (3 pages).
PIMMS. Proton-Ion Medical Machine Study (PIMMS) Part II. European Organization for Nuclear Research CERN—PS Division, Accelerator Complex Study Group, supported by the Med-AUSTRON, Onkologie-2000 and the TERA Foundation and hosted by CERN, Geneva, Switzerland, (Aug. 2000), p. 1787-1789. (352 pages).
Trbojevic, R. Superconducting non-scaling FFAG gantry for carbon/proton cancer therapy. Brookhaven National Laboratory, 22nd Particle Accelerator Conference (PAC), Albuquerque, New Mexico, (2007), (5 pages).
Trbojevic, R. A Dramatically Reduced Size in the Gantry Design for the Proton-Carbon Therapy. 08 Applications of Accelerators, Technology Transfer and Industrial Relations U01 Medical Applications, Proceedings of EPAC 2006, Edinburgh, Scotland, (2006), p. 2352-2354. (3 pages).
Reimoser, Stefan, Development and Engineering Design of a Novel Exocentric Carbon-Ion Gantry for Cancer Therapy (The "Riesenrad" Gantry). 2000, PHD thesis, (170 pages).
U.S. Appl. No. 61/257,329, filed Nov. 2, 2019. Retrieved Nov. 2, 2019, 30 pages.
Office Action and Search Report in TW Application No. 111105938 dated May 16, 2023 (with English translation of Search Report), 6 pages.
Pavlovic, Marius. (1997). Beam-optics study of the gantry beam delivery system for light-ion cancer therapy. Nuclear Inst. and Methods in Physics Research, A, vol. 399, Issue 2, p. 439-454. (16 pages).
International Search Report for International Application No. PCT/US2022/016928, issued Jul. 11, 2022, (8 pages).
Written Opinion for International Application No. PCT/US2022/016928, issued Jul. 11, 2022, (15 pages).
Pavlovic et al., "A Study of Dispersion Effects in Transport of Ion-Therapy Beams," J. Elect. Eng., vol. 58, No. 1, pp. 33-38 (2007).
International Preliminary Report on Patentability for International Application No. PCT/US2022/016928, issued Feb. 1, 2023, (13 pages).
T. Furukawa, et al., Design study of a rotating gantry for the HIMAC new treatment facility, Nuclear Instruments and Methods in Physics Research Section B: Beam Interactions with Materials and Atoms, vol. 266, Issue 10, 2008, pp. 2186-2189, ISSN 0168-583X.
Patent Prosecution Case History downloaded on Sep. 19, 2024, for Application No. EP22708676.6 (137 pages).

* cited by examiner

GANTRY FOR A PARTICLE THERAPY SYSTEM

CROSS-REFERENCE TO RELATED APPLICATION

The benefit of priority is hereby claimed to U.S. Provisional Application No. 63/151,281 titled "Gantry For A Particle Therapy System", which was filed on Feb. 19, 2021. The contents of U.S. Provisional Application No. 63/151,281 are incorporated herein by reference.

TECHNICAL FIELD

This specification describes examples of particle therapy systems and gantries for use therewith.

BACKGROUND

Particle therapy systems use a particle accelerator to generate a particle beam for treating afflictions, such as tumors. Particle therapy systems may use a gantry to direct the particle beam toward a patient from multiple angles. In some examples, a gantry includes a device that supports a radiation delivery apparatus during treatment.

SUMMARY

An example system includes a gantry having a beamline structure configured to direct a particle beam that is monoenergetic from an output of a particle accelerator towards an irradiation target, where the beamline structure includes magnetic bending elements to bend the particle beam along a length of the beamline structure; and an energy degrader downstream of the beamline structure relative to the particle accelerator, where the energy degrader is configured and controllable to change an energy of the particle beam prior to at least part of the particle beam reaching the irradiation target. The example system may include one or more of the following features, either alone or in combination.

The energy degrader may be the sole mechanism by which to actively control the change in energy of the particle beam after the particle beam is output by the particle accelerator and prior to the particle beam reaching the irradiation target. The beamline structure may be configured so as not to actively control the energy of the particle beam after the particle beam is output by the particle accelerator and prior to the particle beam reaching the energy degrader. The magnetic bending elements may include a magnet having a magnetic field of 2.5 Tesla (T) or more. The magnetic bending elements may include a magnet having a magnetic field of 3 Tesla (T) or more.

The example system may include a collimator downstream of the energy degrader relative to the particle accelerator. The collimator may be for blocking at least part of the particle beam prior to at least part of the particle beam reaching the patient. The gantry may include a support structure configured to move part of the beamline structure in a circular path around the irradiation target.

The support structure may have a dimension that is 6 meters or less. The dimension may be a diameter of the support structure. A length of the beamline structure may be 6 meters (m) or less. The length of the beamline structure may be 5 meters (m) or less. An energy of the particle beam may not vary within the beamline structure by more than 1%. A distance between an output of the beamline structure and an isocenter containing the irradiation target may be 1.5 meters (m) or less.

The example system may include a scanning system having one or more scanning magnets to move the particle beam in at least two dimensions across at least part of a beam field that covers at least part of the irradiation target. At least one of the scanning magnets may be, or include, a superconducting magnet. At least one of the scanning magnets may be located downstream of the beamline structure relative to the particle accelerator. At least one of the scanning magnets may be located within the beamline structure. The one or more scanning magnets may include a first scanning magnet located within the beamline structure and a second scanning magnet located downstream of the first scanning magnet relative to the particle accelerator.

The first scanning magnet may be separate from the second scanning magnet. The first scanning magnet may be configured to move the particle beam across the at least part of the beam field in the at least two dimensions. The second scanning magnet may be configured to move the particle beam across the at least part of the beam field in the at least two dimensions. The first scanning magnet may be configured to move the particle beam across the at least part of the beam field a first dimension only. The second scanning magnet may be configured to move the particle beam across the at least part of the beam field in a second dimension only. The second dimension may be different from the first dimension. The first scanning magnet may be located among magnetics included in the beamline structure and the second scanning magnet may be located in a particle beam output device downstream of the beamline structure. The particle beam output device may be, or include, a nozzle. The first scanning magnet may be located in the beamline structure and the second scanning magnet may be located in the beamline structure.

The beamline structure may include an output channel that includes magnetic dipoles arranged in series to bend the particle beam by at least 90°. The magnetic dipoles may include at least a first magnetic dipole and a second magnetic dipole. The first magnetic dipole and the second magnetic dipole may be between the first scanning magnet and the second scanning magnet. The beamline structure may include an output channel configured to bend the particle beam by at least 90° towards an irradiation target in a presence of a magnetic field of at least 3 Tesla (T). The beamline structure may include magnetic dipoles to bend the particle beam and two or more magnetic quadrupoles or magnetic sextuples arranged among the magnetic dipoles along a length of the beamline structure to focus the particle beam.

The example system may include the particle accelerator, which may be a compact particle accelerator. The beamline structure may have an efficiency of 10% or more and a length of 6 meters or less. The efficiency of 10% or more may include 10% or more of the particles output from the particle accelerator being output from the beamline structure An example particle therapy system includes a particle accelerator configured to output particles as a particle beam that is monoenergetic and an example gantry. The example gantry includes a beamline structure configured to direct the particle beam, where the beamline structure has an efficiency of 10% or more and a length of 6 meters or less; and a support structure on which part of the beamline structure is mounted and over which the part of the beamline structure is configured to move. An energy degrader may be downstream of the beamline structure relative to the particle accelerator. The energy degrader may be configured and controllable to change an energy of the particle beam. The efficiency of 10% or more may include 10% or more of the particles output from the particle accelerator being output from the beamline structure. The example particle therapy system may include one or more of the following features, either alone or in combination.

The energy degrader may be the sole mechanism by which to actively control the change in energy of the particle beam after the particle beam is output by the particle accelerator and prior to the particle beam reaching the irradiation target. The gantry may be configured so as not to actively control the energy of the particle beam after the particle beam is output by the particle accelerator and prior to the particle beam reaching the energy degrader. The particle accelerator may have a volume that is 3 cubic meters or less.

The example particle therapy system may include a collimator that is downstream of the energy degrader relative to the particle accelerator. The collimator may be for blocking at least part of the particle beam prior to at least part of the particle beam reaching the patient. The example particle therapy system may include a configurable collimator downstream of the energy degrader relative to the particle accelerator. The configurable collimator may include multiple leaves that are dynamically reconfigurable during movement of the particle beam to change a shape of an edge defined by the multiple leaves. The edge may be movable between at least a portion of the particle beam and a target of the particle beam so that a first part of the particle beam on a first side of the edge is at least partly blocked by the multiple leaves and so that a second part of the particle beam on a second side of the edge is allowed to pass to the target.

The support structure may have a diameter that is 6 meters or less. The beamline structure may include an output channel to direct the particle beam relative to an isocenter of the particle therapy system. A distance between an output of the output channel and the isocenter may be 2 meters or less. The distance between the output of the output channel and the isocenter may be 1 meter or less. The beamline structure may have a length that is 5 meters or less. The beamline structure may include an output channel to direct the particle beam relative to an isocenter of the particle therapy system. The output channel may be configured to bend the particle beam by 90° or more in a presence of a magnetic field of 2.5 Tesla or greater. The beamline structure may include an output channel to direct the particle beam relative to an isocenter of the particle therapy system. The isocenter may be 6 meters or less from the particle accelerator. The particle therapy system may have a footprint of 93 square meters or less. At least one of the particle accelerator or the gantry may generate 10 millisieverts or less of neutrons per gray of dose delivered by the particle beam.

The beamline structure may include an output channel to bend the particle beam by 90° or more. The particle therapy system may include a scanning system to move the particle beam in at least two dimensions across at least part of a beam field. The scanning system may include a first scanning magnet and a second scanning magnet. The first scanning magnet may be in a path of the particle beam and may be within the output channel or upstream of the output channel relative to the particle accelerator. The second scanning magnet may be in a path of the particle beam and may be downstream of the output channel relative to the particle accelerator. The first scanning magnet may be within the output channel. The first scanning magnet may be within the beamline structure but not within the output channel. A least one of the first scanning magnet or the second scanning magnet may include a superconducting magnet. The beamline structure may include an output channel to bend the particle beam by 90° or more in combination with a scanning magnet that is downstream of the output channel relative to the particle accelerator, where the scanning magnet that includes one or more superconducting magnets.

An example particle therapy system includes a particle accelerator configured to output particles as a particle beam that is monoenergetic and a gantry. An example gantry includes an output channel that includes magnetics configured to bend the particle beam by at least 90° in a presence of a magnetic field of at least 2.5 Tesla (T), a support structure on which the output channel is mounted for movement at least part-way around an irradiation target, and a conduit to direct the particle beam to the output channel. The example particle therapy system includes an energy degrader that is downstream of the output channel relative to the particle accelerator, and a scanning system that includes two or more scanning magnets. At least one of the scanning magnets is upstream of at least some magnetics in the output channel relative to the particle accelerator. The two or more scanning magnets may be separated by air or other magnetics and may be configured to move the particle beam across at least part of a beam field in at least two dimensions. The example particle therapy system may include one or more of the following features, either alone or in combination.

The energy degrader may be the sole mechanism by which to actively control a change in energy of the particle beam after the particle beam is output by the particle accelerator and prior to the particle beam reaching the irradiation target. The gantry may be configured so as not to actively control an energy of the particle beam after the particle beam is output by the particle accelerator and prior to the particle beam reaching the energy degrader. The conduit and the output channel together may have an efficiency of 10% or more. The efficiency of 10% or more may include 10% or more of the particles output from the particle accelerator being output from the output channel The two or more scanning magnets may be or include one or more superconducting magnets. The two or more scanning magnets may include a first scanning magnet that is within the output channel or upstream of the output channel relative to the particle accelerator. The scanning system may include a second scanning magnet that is downstream of the output channel. The first scanning magnet may be configured to move the particle beam across the at least part of the beam field in the at least two dimensions, and the second scanning magnet may be configured to move the particle beam across the at least part of the beam field in the at least two dimensions. The first scanning magnet may be configured to move the particle beam across the at least part of the beam field in a first dimension only, and the second scanning magnet may be configured to move the particle beam across the at least part of the beam field in a second dimension only. The second dimension may be different from the first dimension.

The gantry may be 5 meters or less in length measured from the particle accelerator. The magnetics may include a first magnetic dipole to bend the particle beam toward an irradiation target; and a second magnetic dipole upstream of the first magnetic dipole relative to the particle accelerator. The second magnetic dipole may be configured to bend the particle beam toward the first magnetic dipole. The gantry and the particle accelerator may be in a same space and may not be separated by shielding external to the particle accelerator that exceeds 30 centimeters in thickness.

The example particle therapy may have a footprint of 75 square meters or less. The particle accelerator may include a synchrocyclotron, and the particle therapy system may be sized to fit within a vault designed for a linear accelerator (LINAC). The energy degrader may be mounted to the gantry between the output channel and an isocenter of the particle therapy system. The energy degrader may include structures that are movable into and out of a path of the particle beam. The structures may include plates. The structures may include wedges.

A distance between an output of the output channel and an isocenter of the particle therapy system may be 2 meters or less. A distance between an output of the output channel and an isocenter of the particle therapy system may be between 0.8 meters and 1.4 meters. The particle accelerator may include a synchrocyclotron. The particle accelerator may include a synchrotron.

The magnetics in the output channel may include a first magnetic dipole, a second magnetic dipole upstream of the first magnetic dipole relative to the particle accelerator, and one or more focusing magnetic quadrupoles and one or more defocusing magnetic quadrupoles between the first magnetic dipole and the second magnetic dipole. The particle accelerator may include an active return system. The active return system may include superconducting coils that conduct current in a reverse direction to main superconducting coils in the particle accelerator.

The example particle therapy system may include one or more imaging devices mounted to the support structure, and a control system configured to control rotation of the one or more imaging devices along the support structure around an irradiation target. The one or more imaging devices may include one or more of: a computerized tomography (CT) scanner, a two-dimensional (2D) X-ray device, a magnetic resonance imaging (MRI) device, a fan-beam CT scanner, a 2D camera, a three-dimensional (3D) camera, a surface imaging device, or a cone-beam CT scanner.

An example particle therapy system includes a particle accelerator configured to output a particle beam and a gantry configured to connect to the particle accelerator. The gantry may include a beamline structure configured to receive the particle beam from the particle accelerator and also may include magnetics to direct the particle beam to a particle beam output device that is downstream of the beamline structure relative to the particle accelerator. A scanning system is configured to move the particle beam in at least two dimensions across at least part of a beam field. The scanning system may include a first scanning magnet located within the beamline structure and a second scanning magnet located downstream of the first scanning magnet relative to the particle accelerator. The first scanning magnet may be separate from the second scanning magnet. At least one of the first scanning magnet or the second scanning magnet may include a superconducting magnet.

The first scanning magnet may be configured to move the particle beam across the at least part of the beam field in the at least two dimensions. The second scanning magnet may be configured to move the particle beam across the at least part of the beam field in the at least two dimensions. The first scanning magnet may be configured to move the particle beam across the at least part of the beam field a first dimension only. The second scanning magnet may be configured to move the particle beam across the at least part of the beam field in a second dimension only. The second dimension may be different from the first dimension. The first scanning magnet may be located among magnetics included in the beamline structure and the second scanning magnet may be located in the particle beam output device. The particle beam output device may be, or include, a nozzle.

The first scanning magnet may be located in the beamline structure and the second scanning magnet may be located downstream of the beamline structure relative to the particle accelerator. The beamline structure may include an output channel configured to bend the particle beam by at least 90° towards an irradiation target in a presence of a magnetic field of at least 2.5 Tesla (T). The beamline structure may include magnetic dipoles to bend the particle beam and two or more magnetic quadrupoles or magnetic sextupoles arranged among the magnetic dipoles along a length of the beamline structure. The beamline structure may include an output channel having magnetic dipoles arranged in series to bend the particle beam by at least 90°. The magnetic dipoles may include at least a first magnetic dipole and a second magnetic dipole. The first magnetic dipole and the second magnetic dipole may be between the first scanning magnet and the second scanning magnet.

The particle accelerator and the gantry may be located in a same treatment space. The treatment space may include a first compartment and a second compartment having no shielding between the first compartment and the second compartment or having shielding between the first compartment and the second compartment that is less than 30 centimeters thick. The particle accelerator may be configured to output the particle beam at one of two energy levels. One of the energy levels may be greater than another of the energy levels.

The particle accelerator may include main superconducting coils to generate a magnetic field for accelerating particles to produce the particle beam. The particle accelerator may include active return coils to conduct current in an opposite direction as in the main superconducting coils. The particle beam may be output from the particle beam output device at FLASH doses. The particle beam may be output from the particle beam output device at a dose that exceeds twenty (20) Gray-per-second for a duration of less than five (5) seconds.

The gantry may include a support structure to which at least part of the beamline structure is mounted. The particle therapy system may include an imaging system coupled to the support structure and configured for rotation about the support structure. The imaging system may be configured to capture images of an irradiation target, the imaging system may include one or more of: a computerized tomography (CT) scanner, a two-dimensional (2D) X-ray device, a magnetic resonance imaging (MRI) device, a fan-beam CT scanner, a 2D camera, a three-dimensional (3D) camera, a surface imaging device, or a cone-beam CT scanner.

The particle therapy system may include a control system programmed to control output of the particle beam to an irradiation target based on the images. The particle accelerator may be configured to output the particle beam at multiple energy levels. The particle therapy system may include a control system to select among the multiple energy levels.

An example particle therapy system includes a particle accelerator having a volume that is 2 cubic meters or less. The particle accelerator is configured to output particles as a particle beam that is monoenergetic. The particles are output to an irradiation target at an efficiency of 10% or more. The efficiency of 10% or more includes 10% or more of the particles output from the particle accelerator reaching the irradiation target. The particle accelerator may be stationary and the particle beam may be fixed for output from the particle accelerator in a single direction only. A treatment couch may be configured to move in three or more degrees of freedom relative to the particle beam. The example particle therapy system may include one or more of the following features, either alone or in combination.

The particle therapy system may have a footprint of 75 square meters or less. The treatment couch may be configured to move in at least four degrees of freedom relative to the particle beam. The particle therapy system may include an energy degrader that is the sole mechanism by which to actively control a change in energy of the particle beam after the particle beam is output by the particle accelerator and prior to the particle beam reaching the irradiation target.

An example scanning magnet is for use in a particle therapy system to treat an irradiation target. The scanning magnet is configured to move a particle beam in at least two dimensions relative to the irradiation target. The scanning magnet includes a first set of superconducting coils to move the particle beam in a first dimension relative to the irradiation target, and a second set of superconducting coils to move the particle beam in a second dimension relative to the irradiation target, where the second dimension is different than the first dimension. The scanning magnet may include one or more of the following features, either alone or in combination.

The second dimension may be orthogonal to the first dimension. The scanning magnet may include an electrically non-superconducting material separating the first set of superconducting coils from the second set of superconducting coils. The scanning magnet may include an electrically nonconductive material separating the first set of superconducting coils from the second set of superconducting coils. The scanning magnet may include a cryocooler to maintain the first set of superconducting coils and the second set of superconducting coils at high-temperature superconducting temperatures.

Each coil in at least one of the first set of superconducting coils or the second set of superconducting coils may include a rare-earth barium copper oxide (ReBCO) superconducting layer. Each coil in at least one of the first set of superconducting coils or the second set of superconducting coils may include a silver (Ag) cap layer adjacent to the rare-earth barium copper oxide (ReBCO) superconducting layer. Each coil in at least one of the first set of superconducting coils or the second set of superconducting coils may include a buffer layer stack adjacent to the rare-earth barium copper oxide (ReBCO) superconducting layer. Each coil in at least one of the first set of superconducting coils or the second set of superconducting coils may include a metal substrate layer adjacent to the buffer layer stack. Each coil in at least one of the first set of superconducting coils or the second set of superconducting coils may include a copper layer encasing the coil.

The scanning magnet may include a cryostat containing the first set of superconducting coils and the second set of superconducting coils. The cryostat may be for maintaining the first set of superconducting coils and the second set of superconducting coils at high-temperature superconducting temperatures. Each coil in at least one of the first set of superconducting coils or the second set of superconducting coils may include a superconducting layer comprised of YBCO or BSCCO.

Any two or more of the features described in this specification, including in this summary section, may be combined to form implementations not specifically described in this specification.

Control of the various systems described herein, or portions thereof, may be implemented via a computer program product that includes instructions that are stored on one or more non-transitory machine-readable storage media and that are executable on one or more processing devices (e.g., microprocessor(s), application-specified integrated circuit (s), programmed logic such as field programmable gate array(s), or the like). The systems described herein, or portions thereof, may be implemented as an apparatus, method, or a medical system that may include one or more processing devices and computer memory to store executable instructions to implement control of the stated functions. The devices, systems, and/or components described herein may be configured, for example, through design, construction, arrangement, placement, programming, operation, activation, deactivation, and/or control.

The details of one or more implementations are set forth in the accompanying drawings and the following description. Other features and advantages will be apparent from the description and drawings, and from the claims.

DESCRIPTION OF THE DRAWINGS

Like reference numerals in different figures indicate like elements.

DETAILED DESCRIPTION

Described herein are example particle therapy systems that may house the patient and the accelerator in the same space. An example system includes a particle accelerator that may be, but is not limited to, a synchrocyclotron that has low radiation leakage and that is small enough to fit within a standard linear accelerator (LINAC) vault. The system also includes a medical gantry configured to deliver a charged particle beam, such as protons or ions, output from the accelerator to treat tumors or other conditions in a patient. The gantry includes a beamline structure to direct the particle beam from the accelerator to a treatment position and to deliver the particle beam to the treatment position. The beamline structure includes magnetics, such as one or more magnetic dipoles and one or more magnetic quadrupoles, to direct the particle beam towards the treatment position. To enable delivery of the particle beam in the same space that is used for treatment, particularly in relatively small spaces such as a standard LINAC vault, at least some of the magnetics in the beamline structure are configured to bend the particle beam at right angles or at obtuse angles. In an example, the magnetics are configured and arranged to bend the particle beam by 90° or greater.

Implementations of the particle therapy system described herein also combine the functionality of large-aperture superconducting magnets with the use of upstream scanning magnets to make the particle therapy system relatively compact. Although compact in construction, the example particle therapy system is configured to enable beam focusing, beam scanning, beam bending, and beam rotation as described below.

Figure 1:
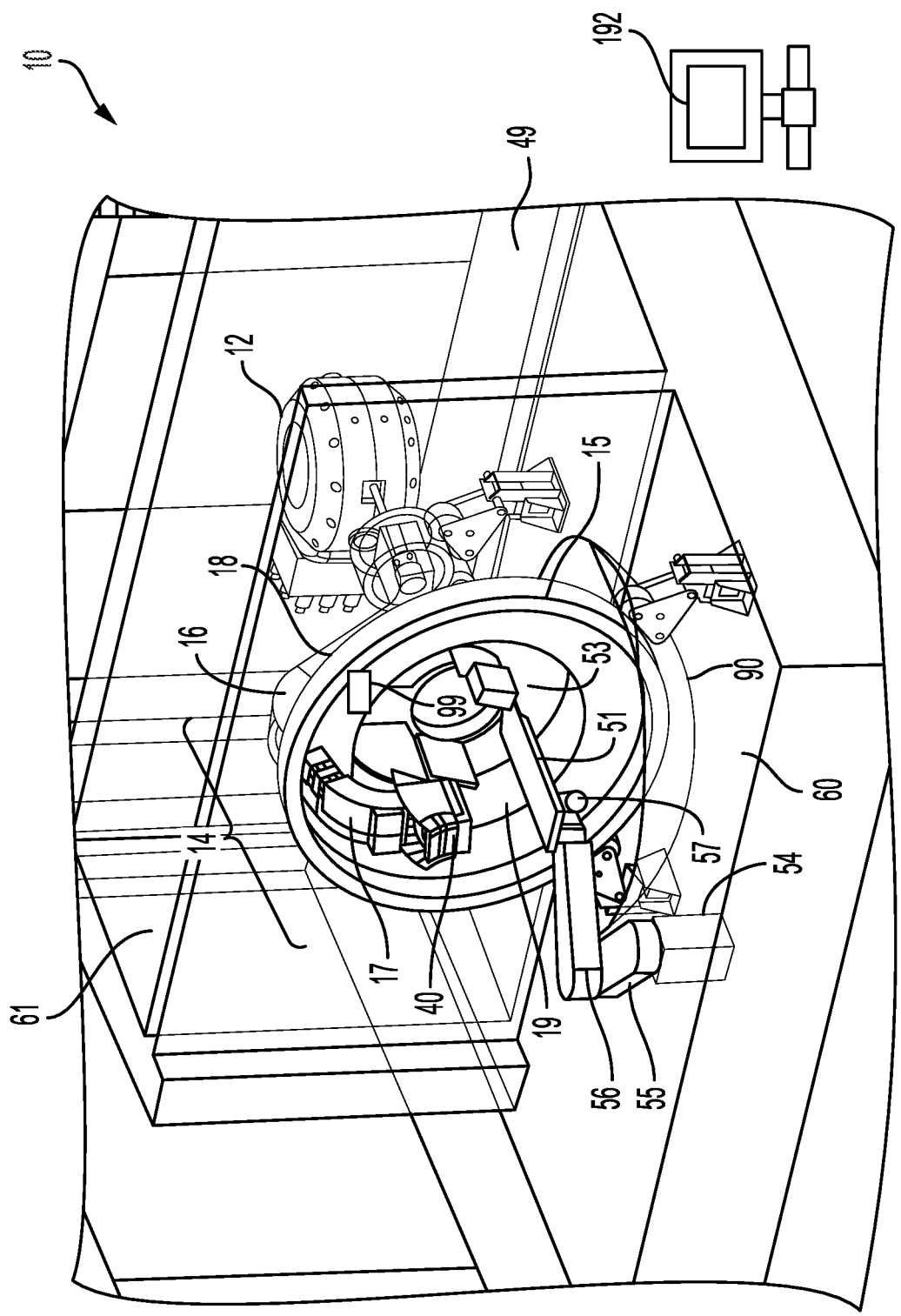
FIG. 1 is a diagram showing a partially transparent perspective view of an example particle therapy system having an example gantry of the type described herein.

FIG. 1 shows an example implementation of a particle therapy system 10 of the type described in the preceding paragraphs. As shown in FIG. 1, particle therapy system 10 includes a particle accelerator 12, examples of which are described herein. In this example, particle accelerator 12 is a synchrocyclotron having a superconducting electromagnetic structure that generates a maximum magnet field strength of 2.5 Tesla (T) or more or 3 T or more. In this regard, a superconductor is an element or metallic alloy such as niobium-tin ($Nb_3Sn$) which, when cooled below a threshold temperature, loses most, if not all, electrical resistance. As a result, current flows through the superconductor substantially unimpeded. Superconducting coils, therefore, are capable of conducting larger currents in their superconducting state than ordinary wires of the same size. Because of the high amounts of current that they are capable of conducting, superconducting coils are particularly useful in particle therapy applications.

An example synchrocyclotron is configured to output protons or ions as a monoenergetic particle beam having an energy level of 150 MegaElectronvolts (MeV) or more. The example synchrocyclotron has a volume of 4.5 cubic meters ($m^3$) or less and a weight of 30 Tons (T) or less. Due to its size, this type of particle accelerator is referred to as "compact". However, as described herein, synchrocyclotrons or other types of particle accelerators having weights, dimensions, magnetic fields, and/or energy levels other than these may be used in particle therapy system 10.

Particle therapy system 10 also includes gantry 14. Gantry 14 includes ring-shaped or circular support structure 15 and a beamline structure 16. The combination of support structure 15 and beamline structure 16 may be referred to as a "compact gantry" due to its relatively small size. Beamline structure 16 includes an output channel 17 that mounts to support structure 15 and a conduit 18 that directs the particle beam to the output channel. Gantry 14 also includes one or more motors (not shown) for moving output channel 17 around support structure 15 relative to a treatment position 19. The treatment position may include a system isocenter where a patient may be positioned for treatment. In an example, the motors may move output channel 17 along a track on structure 15 resulting in rotation of output channel 17 relative to treatment position 19. In an example, a structure to which output channel 17 is attached may rotate relative to treatment position 19, resulting in rotation of output channel 17 relative to the treatment position. In some implementations, the rotation enabled by gantry 14 allows output channel 17 to be positioned at any angle relative to the treatment position. For example, output channel 17 may rotate through 360° and, as such, output channel 17 may be positioned at 0°, 90°, 270°, and back to 0°/360° or any angle among these rotational positions.

As noted previously, beamline structure 16 is configured to direct a particle beam from accelerator 12 to treatment position 19. To this end, output channel 17 includes magnetics to bend the particle beam towards the treatment position. In addition, beamline structure 16 includes conduit 18 containing magnetics along the beamline that direct the particle beam from particle accelerator 12 to output channel 17.

Figure 2:
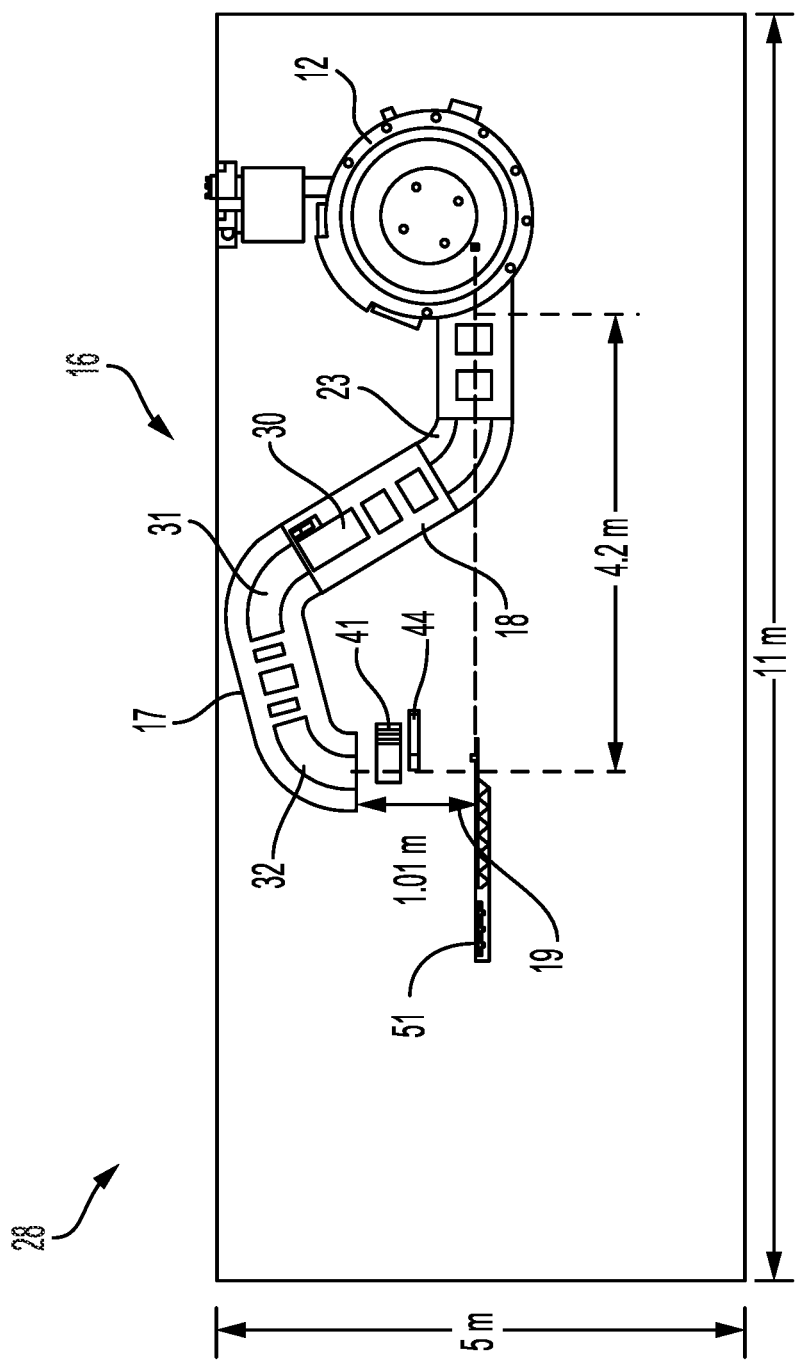
FIG. 2 is a cut-away, side view of components of the particle therapy system shown in FIG. 1, including the example gantry.
Figure 3:
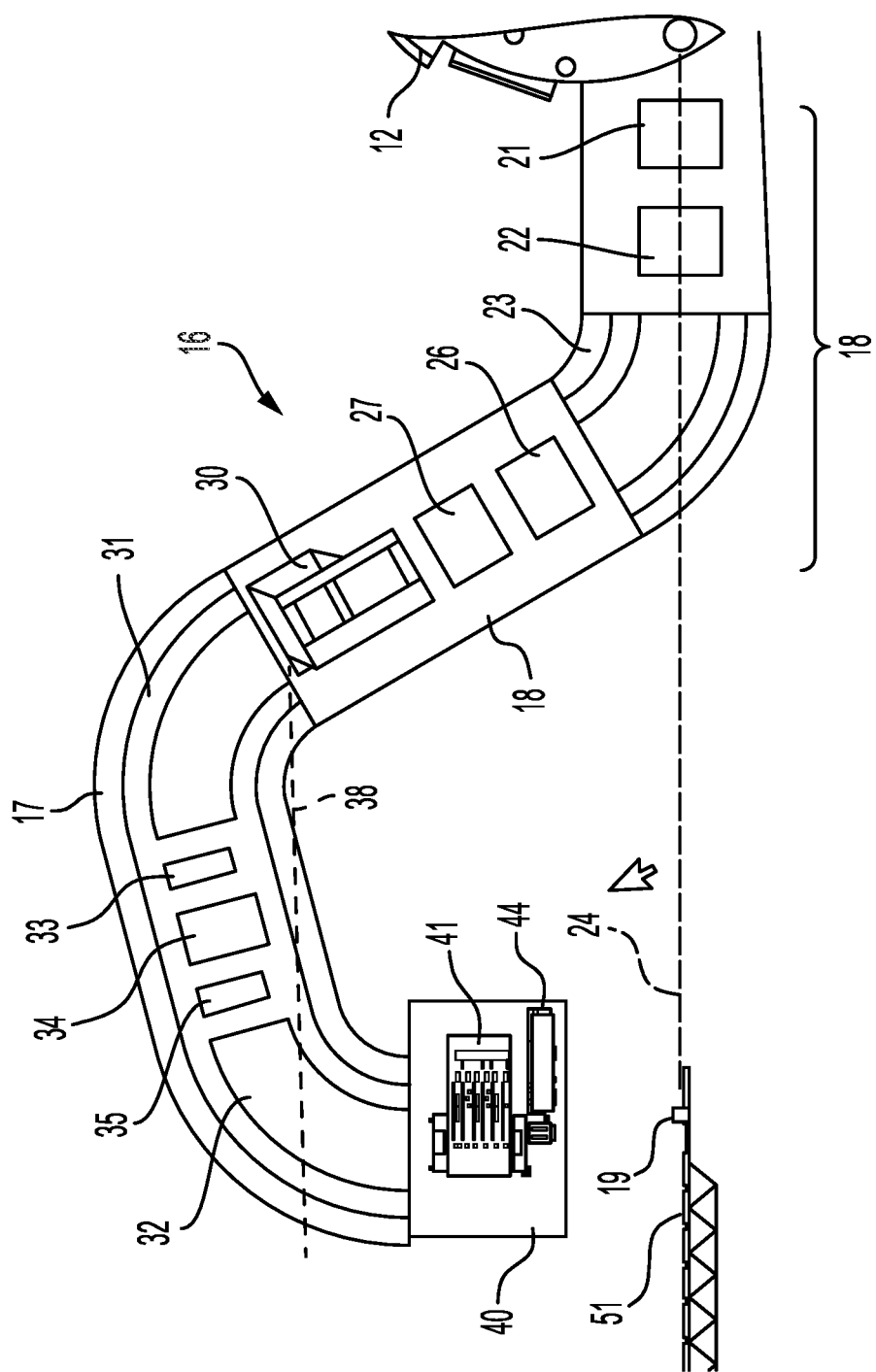
FIG. 3 is a cut-away, close-up, side view of components included in in a nozzle and an example beamline structure that may be part of the gantry shown in FIG. 1.

Referring to FIGS. 2 and 3, conduit 18 of example beamline structure 16 includes non-superconducting magnetic quadrupoles 21 and 22 and superconducting magnetic dipole 23. The outer electromagnetically shielded shell of beamline structure 16 is omitted, in part, from the illustrations of FIGS. 2 and 3. Magnetic quadrupoles 21 and 22 are configured to keep the particle beam focused and traveling straight or substantially straight—for example, a 5% or less deviation from straight—within beamline structure 16. Magnetic quadrupoles 21 and 22 are configured to focus the particle beam to maintain a substantially consistent cross-sectional area of the particle beam, for example, to within a tolerance of ±5%. Magnetic dipole 23 is configured to bend the particle beam towards output channel 17, as shown in the figures. Magnetic dipole 23 may be configured to bend the particle beam anywhere in a range of 20° to 80° relative to horizontal 24. Generally, greater bend angles may reduce the distance between particle accelerator 12 and treatment position 19 or system isocenter, thereby reducing the space required to accommodate the gantry and, thus, the size of the particle therapy system. For example, replacing magnetic dipole 23 with one or more superconducting magnetic dipoles that bend the particle beam by more than 80°—for example, by 90° or more—may further reduce the distance from particle accelerator 12 to support structure 15 and, thus, to treatment position 19 and the isocenter.

In some implementations, higher-order magnetics may be used in place of, or in addition to, any magnetic quadrupoles described herein. For example, the beamline structure may include one or more magnetic sextupoles in place of, or in addition to, the magnetic quadrupoles. The magnetic sextupoles may be configured to keep the particle beam focused and traveling straight or substantially straight—for example, a 5% or less deviation from straight—within beamline structure 16. The magnetic sextupoles may also configured to maintain a consistent cross-sectional area of the particle beam, for example, to within a tolerance of ±5%. Also, sextuple magnets may correct for chromatic effect of a quadrupole magnet. Compared with a magnetic quadrupole, a magnetic sextuple has a greater focusing effect for particles that are displaced farther from an axis that defines the ideal location of the beamline.

Referring back to FIG. 3, in this example, conduit 18 of beamline structure 16 also includes two non-superconducting magnetic quadrupoles 26 and 27. Magnetic quadrupoles 26 and 27 are configured to keep the particle beam focused and traveling straight or substantially straight—for example, a 5% or less deviation from straight—within beamline structure 16. Magnetic quadrupoles 26 and 27 are configured to maintain a consistent cross-sectional area of the particle beam, for example, to within a tolerance of ±5%. As described previously, higher-order magnetics may be substituted for one or more of the magnetic quadrupoles to improve focusing.

Particle therapy system 10 also includes one or more scanning magnets 30 in the path of the particle beam and configured to move the particle beam across at least part of a beam field that covers all or part of (that is, at least part of) the irradiation target. In some examples, the beam field includes the maximum extent that the particle beam can be moved across a plane parallel to a treatment area on a patient for a given position of the compact gantry. Movement of the particle beam across the beam field results in movement across at least part of an irradiation target at a treatment position 19. The scanning magnets may be sized and configured to move the particle beam across a beam field having an area of 20 centimeters (cm) by 20 cm or greater, although system 10 is not limited to any particular beam field size. For example, the scanning magnets may have an aperture of 20 cm by 20 cm or greater, although the scanning magnets are not limited to any particular aperture size.

Figure 4:
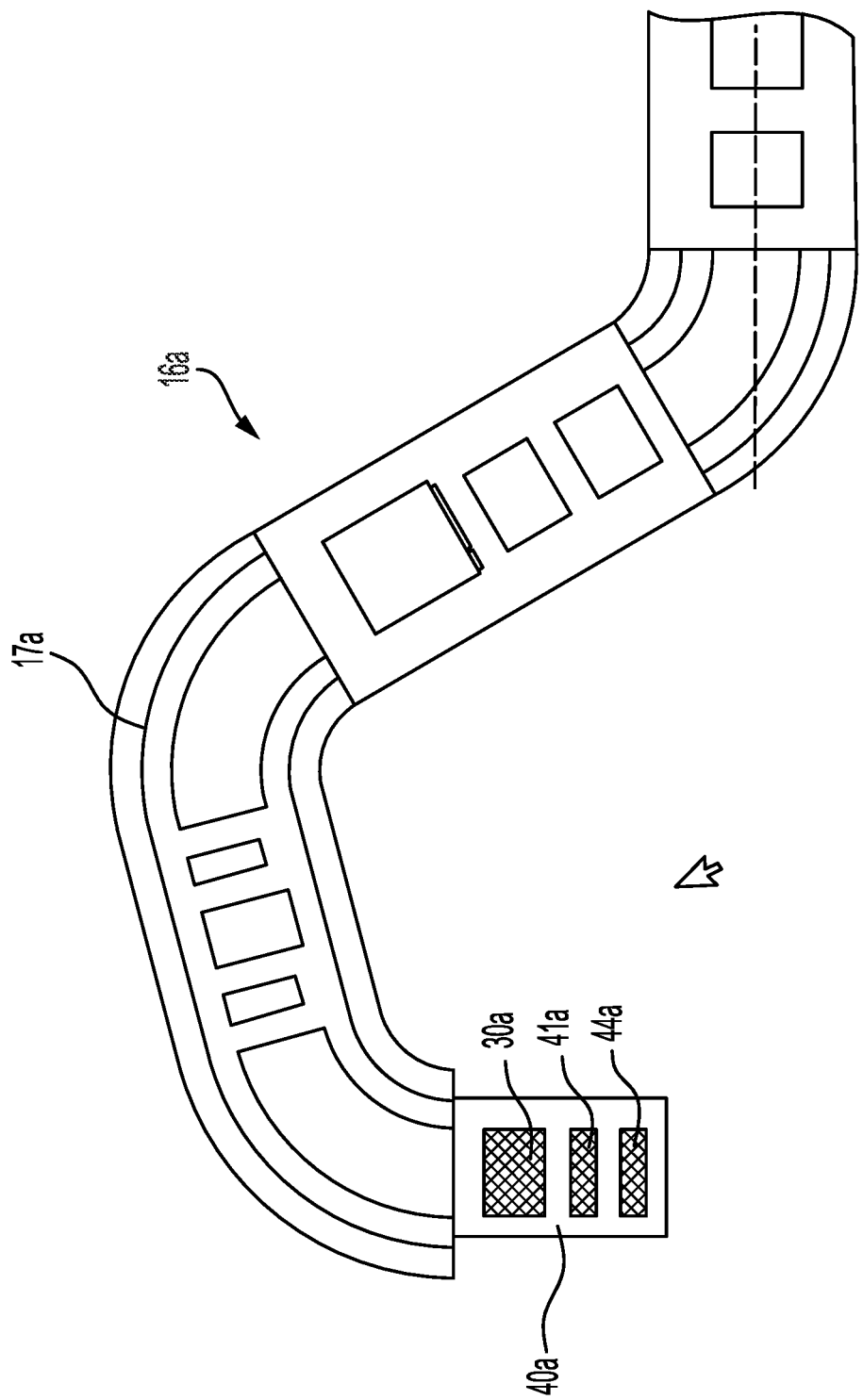
FIG. 4 is a cut-away, close-up, side view of components included in a nozzle and an example beamline structure that may be part of the gantry shown in FIG. 1.
Figure 5:
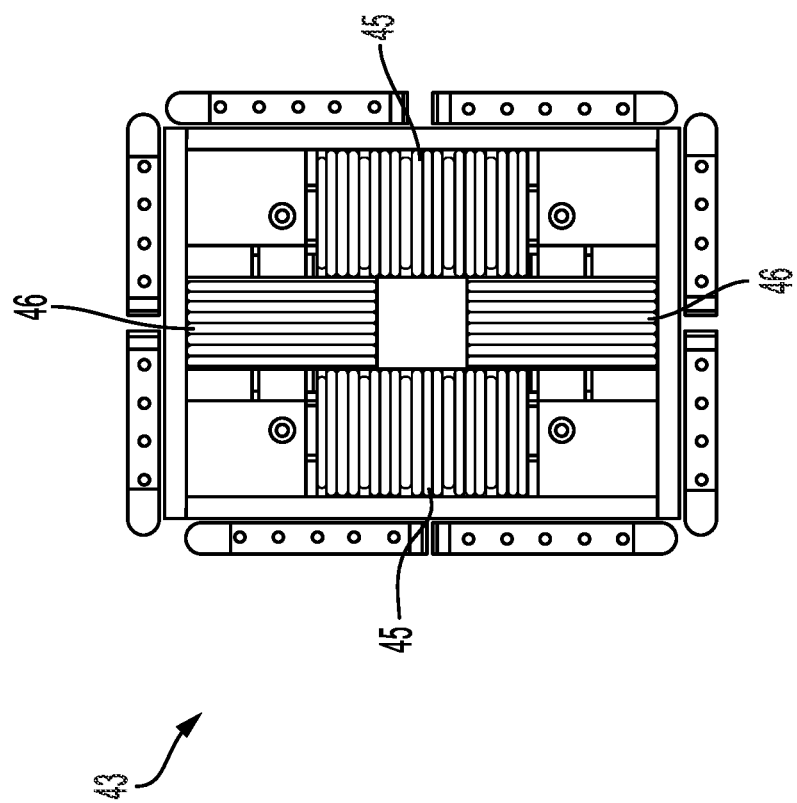
FIG. 5 is an illustration of a front view of an example scanning magnet configured to scan a particle beam in two orthogonal dimensions.

The scanning magnets may be located at different positions within the particle therapy system. For example, in beamline structure 16a shown in FIG. 4, which is a variant of beamline structure 16, all of the scanning magnets 30a may be located in nozzle 40a, along with energy degrader 41a and collimator 44a (both described below), on a path of the particle beam between output channel 17a and the treatment position. Referring to FIG. 5, an example scanning magnet 43 is controllable in two dimensions (e.g., Cartesian XY dimensions) to position the particle beam in those two dimensions and to move the particle beam across at least a part of an irradiation target. In this example, scanning magnet 43 includes a first set 45 of two coils, which control particle beam movement in the Cartesian X dimension of a defined coordinate system, and a second set 46 of two coils, which are orthogonal to the first set of two coils and which control particle beam movement in the Cartesian Y dimension. Control over movement of the particle beam may be achieved by varying current through one or both sets of coils to thereby vary the magnetic field(s) produced thereby. By varying the magnetic field(s) appropriately, the magnetic fields acts on the particle beam to move the particle beam in the X and/or Y dimension across a beam field and, thus, the irradiation target.

In some implementations there may be more than one scanning magnet. Implementations that include multiple scanning magnets that are at different points along the path of the particle beam and that are separated by air or structures such as magnets or beam-absorbing plates may be referred to as split scanning systems. For example, in beamline structure 16b shown in FIG. 6, which is a variant of beamline structure 16, there may be multiple—for example, two—scanning magnets 30b1 and 30b2 between the between output channel 17b and the treatment position. The scanning magnets may be located in nozzle 40b, along with energy degrader 41b and collimator 44b, on a path of the particle beam between output channel 17b and the treatment position. The scanning magnets may be at separate locations and separated by air or an energy-degrading structure. For example, in this implementation, a first scanning magnet 30b1 may move the particle beam in two dimensions (for example, Cartesian X and Y dimensions) and a second scanning magnet 30b2 may move the particle beam in two dimensions (for example, Cartesian X and Y dimensions). In this example, scanning magnets 30b1 and 30b2 may have the same construction and operation as the scanning magnet shown in FIG. 5. Each magnet 30b1 and 30b2 may move the beam partly, with the combined movements produced by the two magnets producing the desired movement specified in a treatment plan.

Figure 6:
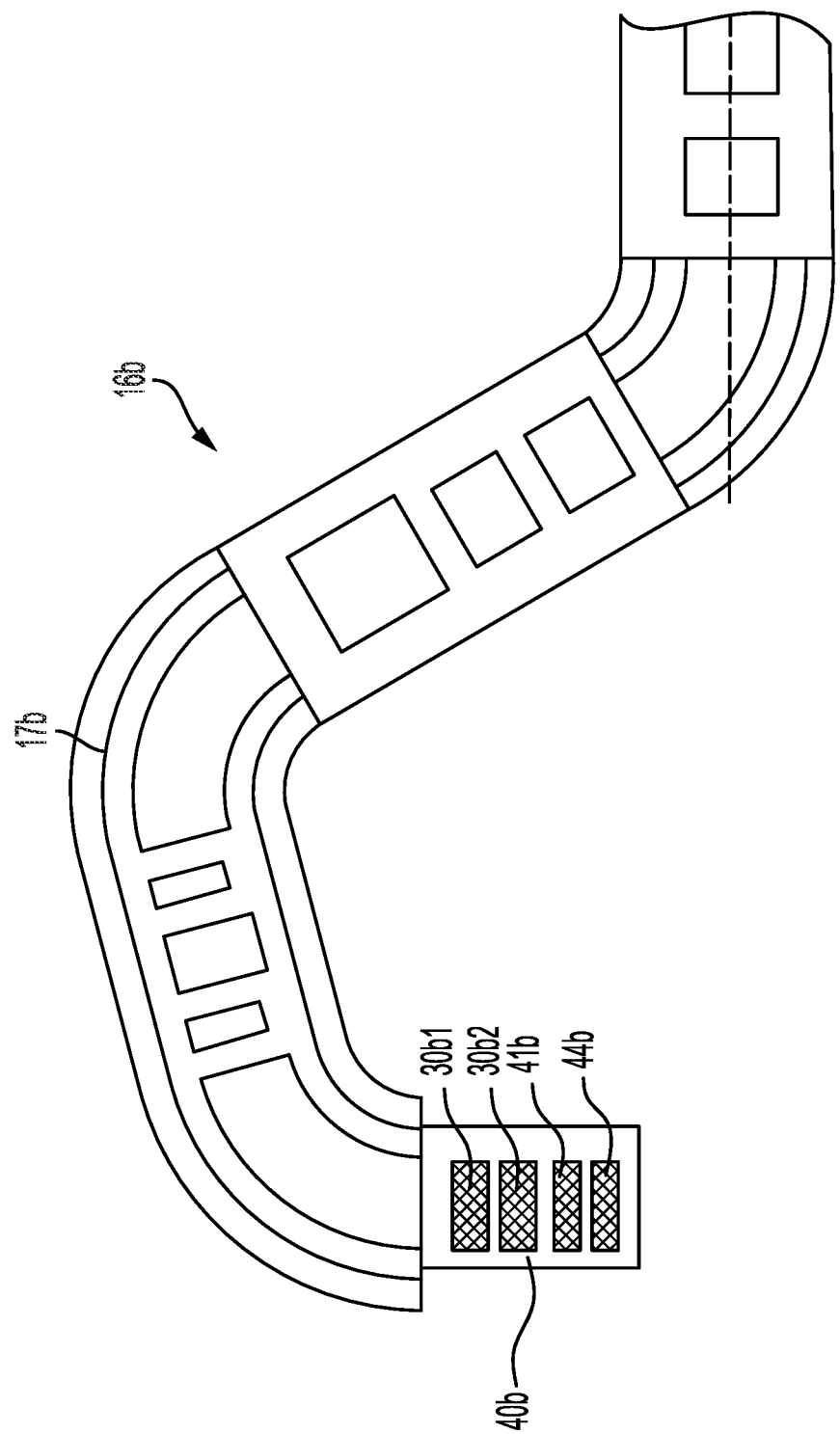
FIG. 6 is a cut-away, close-up, side view of components included in a nozzle and an example beamline structure that may be part of the gantry shown in FIG. 1.
Figure 8:
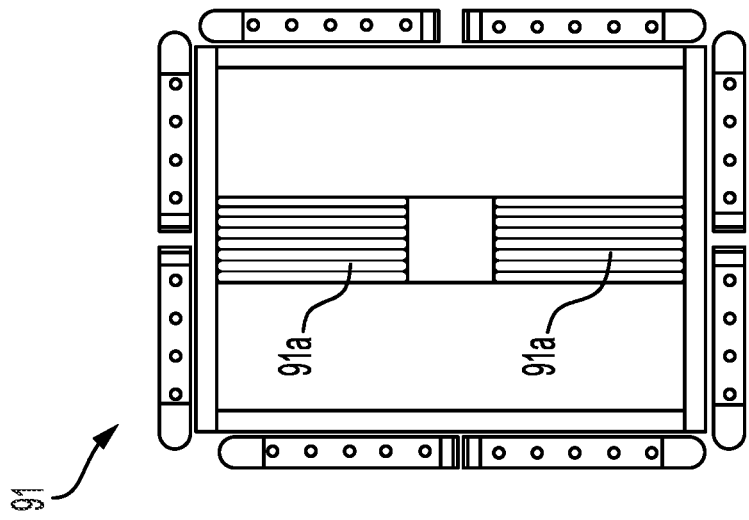
FIG. 8 is an illustration of a front view of an example scanning magnet configured to scan a particle beam in a single dimension.
Figure 7:
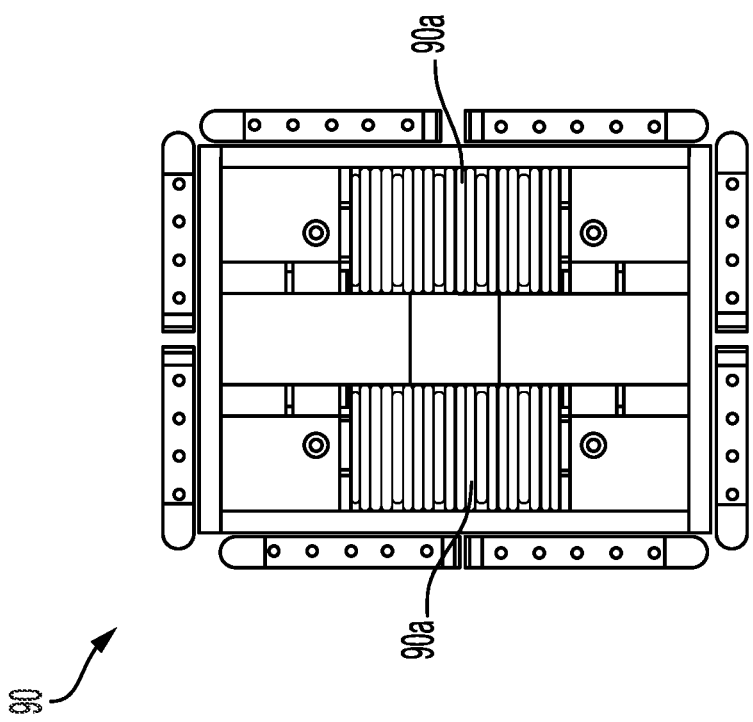
FIG. 7 is an illustration of a front view of an example scanning magnet configured to scan a particle beam in a single dimension.

In a variant of the FIG. 6 implementation, scanning magnet 30b1 may move the particle beam in one dimension only (for example, the Cartesian X dimension) and scanning magnet 30b2 may move the particle beam in one dimension only (for example, the Cartesian Y dimension). One magnet 30b1 may be upstream of the other magnet 30b2 relative to the particle accelerator as shown in the figure. The two may be separated by air or an energy degrading structure as noted above. FIGS. 7 and 8 show example magnets 90 and 91, respectively, having orthogonal coils—coils 90a are orthogonal to coils 91a—to move the particle beam in different dimensions. In this example, scanning magnet 30b1 may be of the type shown in FIG. 7 and include a first set of coils 90a and scanning magnet 30b2 may be of the type shown in FIG. 8 and include a second set of coils 91a that are orthogonal to coils 90a. Each magnet 30b1, 30b2 may move the beam partly, with the combined movements produced by the two magnets producing the desired movement specified in a treatment plan.

Figure 9:
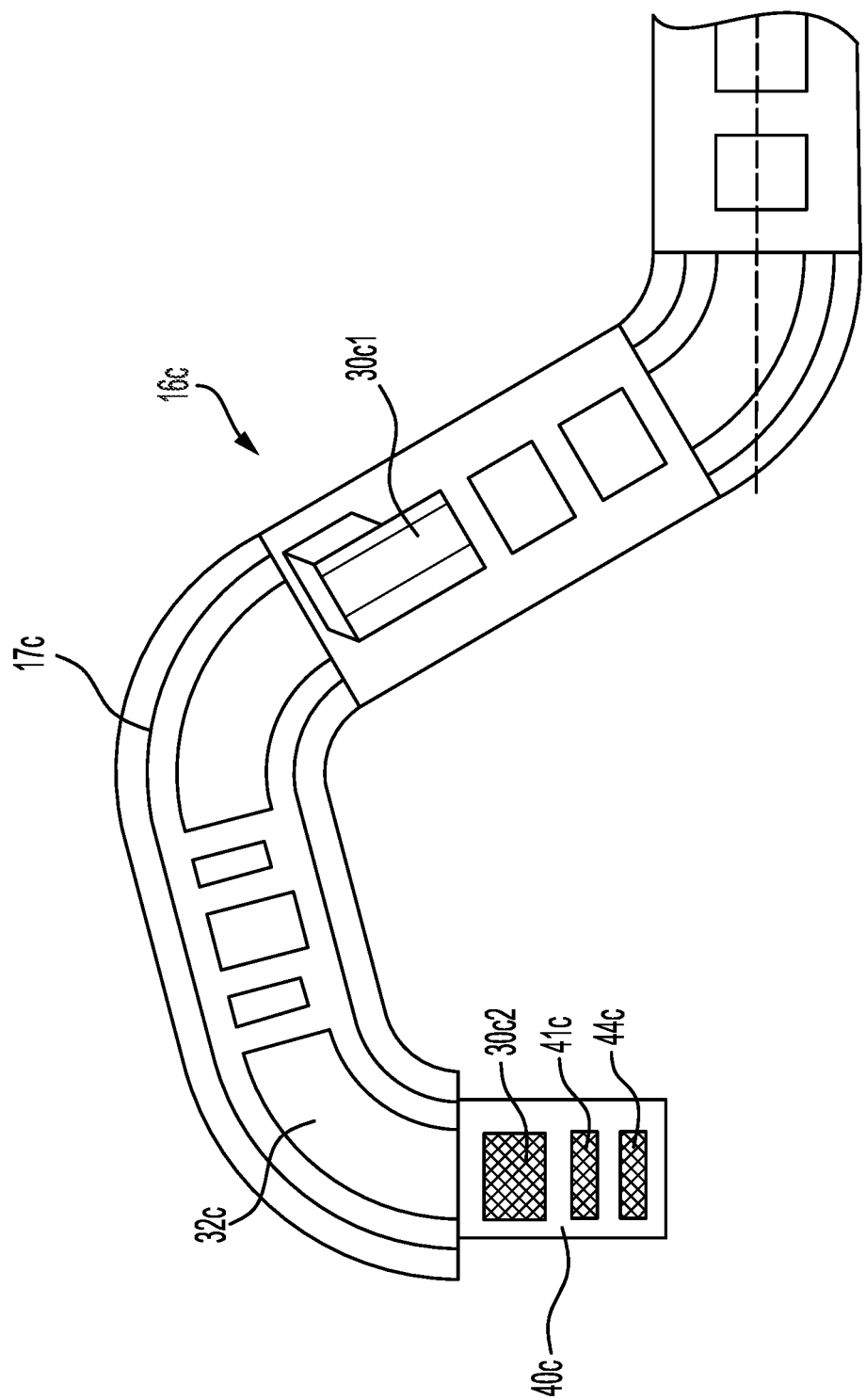
FIG. 9 is a cut-away, close-up, side view of components included in a nozzle and an example beamline structure that may be part of the gantry shown in FIG. 1.

In some implementations, one or more—for example, all or fewer than all—of the scanning magnets may be located in the beamline structure. For example, in beamline structure 16c shown of FIG. 9, which is a variant of beamline structure 16, there may be multiple—for example, two—scanning magnets including a first scanning magnet 30c1 located within beamline structure 16c and a second scanning magnet 30c2 located outside of the beamline structure in nozzle 40c, along with energy degrader 41c and collimator 44c between output channel 17 and the treatment position. The first scanning magnet 30c1 may be located among the magnetics included in beamline structure 16c. For example, first scanning magnet 30c1 may be located within output channel 17c upstream of magnetic dipole 32c relative to the particle accelerator, or as shown in FIG. 9 first scanning magnet 30c1 may be located upstream of output channel 17c relative to the particle accelerator. In an example, first scanning magnet 30c1 may be configured to move the particle beam in two dimensions (for example, Cartesian X and Y dimensions) and second scanning magnet 30c2 may be configured to move the particle beam in two dimensions (for example, Cartesian X and Y dimensions). In this example, scanning magnets 30c1 and 30c2 may have the same construction and operation as the scanning magnet shown in FIG. 5. Each magnet 30c1 and 30c2 may move the beam partly, with the combined movements produced by the two magnets producing the desired movement specified in a treatment plan.

In a variant of the FIG. 9 implementation, first scanning magnet 30c1 may be configured to move the particle beam in one dimension only (for example, the Cartesian X dimension) and second scanning magnet 30c2 may be configured to move the particle beam in one dimension only (for example, the Cartesian Y dimension). In this example, scanning magnet 30c1 may include a first set of coils and scanning magnet 30c2 may include a second set of coils that are orthogonal to the first set of coils. Magnets 30c1 and 30c2 may have configurations like the magnets shown in FIGS. 7 and 8 in this example. Each magnet 30c1 and 30c2 may be configured to move the beam partly, with the combined movements produced by the two magnets producing the desired movement specified in a treatment plan.

Figure 10:
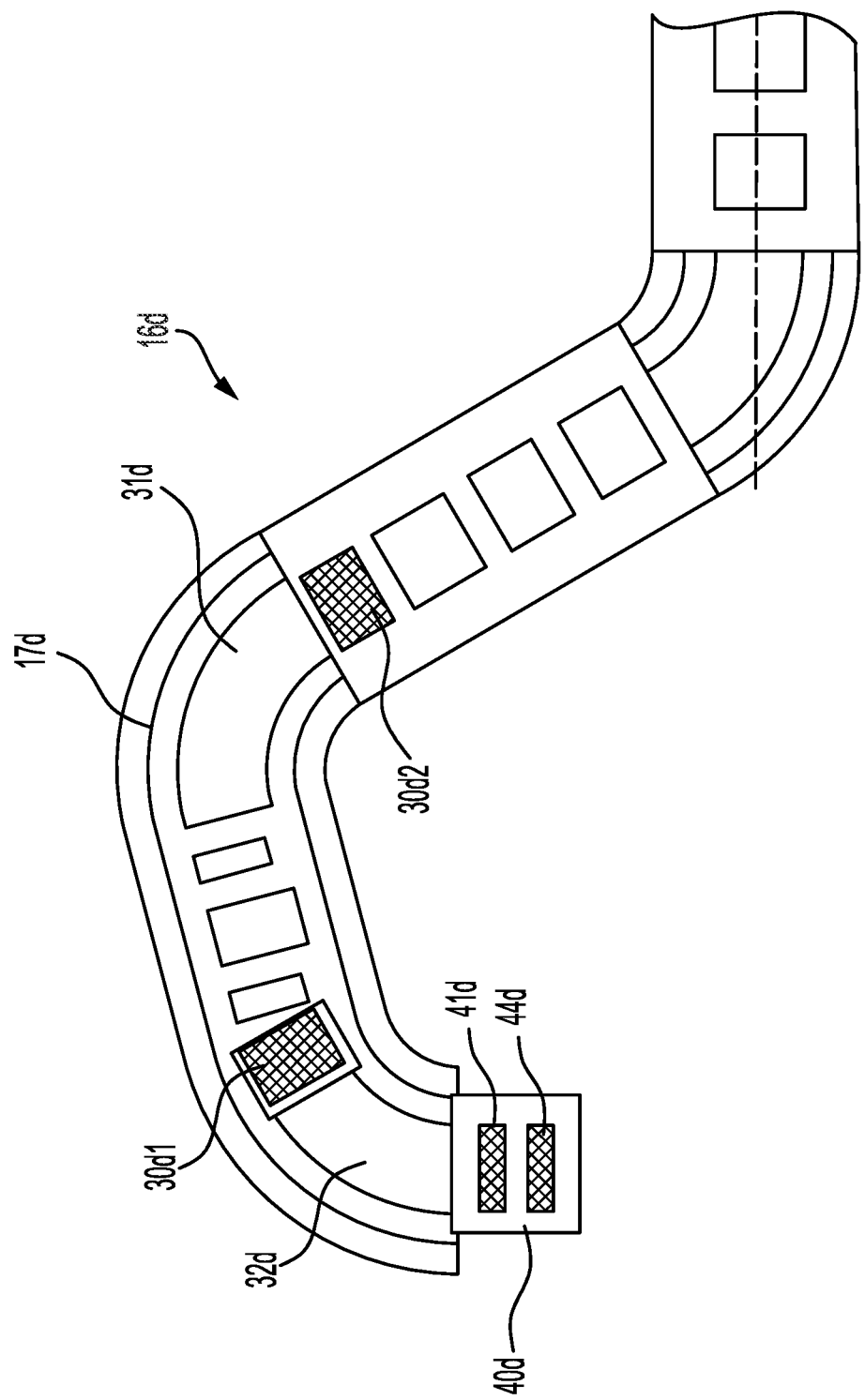
FIG. 10 is a cut-away, close-up, side view of components included in a nozzle and an example beamline structure that may be part of the gantry shown in FIG. 1.

In some implementations, all of the scanning magnets may be located in the beamline structure. As shown in the split scanning system of FIG. 10, both a first scanning magnet 30d1 and a second scanning magnet 30d2 may be located within beamline structure 16d, which is a variant of beamline structure 16. No scanning magnets may be located in nozzle 40d, which includes energy degrader 41d and collimator 44d in this example. In other examples, there may be one or more scanning magnets also in the nozzle. First scanning magnet 30d1 and second scanning magnet 30d2 may be located among the magnetics included in beamline structure 16d. For example, as shown in FIG. 10 first scanning magnet 30d1 may be located within output channel 17d upstream of magnetic dipole 32d relative to the particle accelerator, or the first scanning magnet may be located upstream of output channel 17d relative to the particle accelerator. Second scanning magnet 30d2 may be located upstream of first scanning magnet 30d1 relative to the particle accelerator. In the example shown in FIG. 10, second scanning magnet 30d2 precedes output channel 17d in the beamline. The scanning magnets may be at separate locations within the beamline structure and separated by magnetics, such as a dipole or quadrupole, and/or air within the beamline structure. The separate locations may include different points or locations in series along a path of the particle beam or length of the beamline structure. For example, as shown in FIG. 10, magnetic dipole 31d is between first scanning magnet 30d1 and second scanning magnet 30d1. In another example, scanning magnet 30d1 may be moved after magnetic dipole 32d such that both magnetic dipoles 31d and 32d are between scanning magnets 30d1 and 30d1. In another example, both scanning magnets 30d1 and 30d2 may be within output channel 17d and magnetic dipoles 31d and 32d may be between scanning magnets 30d1 and 30d2. In an example, first scanning magnet 30d1 may be configured to move the particle beam in two dimensions (for example, Cartesian X and Y dimensions) and second scanning magnet 30d2 may be configured to move the particle beam in two dimensions (for example, Cartesian X and Y dimensions). In this example, scanning magnets 30d1 and 30d2 may have the same construction and operation as the scanning magnet shown in FIG. 5. Each magnet 30d1 and 30d2 may move the particle beam partly, with the combined movements produced by the two scanning magnets producing the desired particle beam movement specified in a treatment plan.

In a variant of the FIG. 10 implementation, first scanning magnet 30d1 may be configured to move the particle beam in one dimension only (for example, the Cartesian X dimension) and second scanning magnet 30d2 may be configured to move the particle beam in one dimension only (for example, the Cartesian Y dimension). In this example, scanning magnet 30d1 may include a first set of coils and scanning magnet 30d2 may include a second set of coils that are orthogonal to the first set of coils. Magnets 30d1 and 30d2 may have configurations like the magnets shown in FIGS. 7 and 8 in this example. Each magnet 30d1 and 30d2 may be configured to move the beam partly, with the combined movements produced by the two magnets producing the desired movement specified in a treatment plan.

In some implementations, there may be more than two scanning magnets located within the beamline structure and/or located between the output of the output channel and the treatment position. For example, there may be three or more scanning magnets located at various separate locations within the beamline structure. For example, there may be three or more scanning magnets located at various separate locations between the output of the output channel and the treatment position. In each case, the scanning magnets may be arranged in series.

In some implementations, there may be a single scanning magnet located within the beamline structure upstream of the output of output channel or elsewhere. For example, as shown in FIGS. 2 and 3, scanning magnet 30 may be located upstream of output channel 17 relative to the particle accelerator and at the input of output channel 17. Scanning magnet 30 may be configured to move the particle beam in two dimensions (for example, the Cartesian X and Y dimension). In this example, scanning magnet 30 may have the same construction and operation as the scanning magnet shown in FIG. 5. In this example, all particle beam movement is implemented by controlling current through one or more coils of the single scanning magnet.

In this regard, by positioning all or some of the scanning magnets within a beamline structure, it may be possible to reduce the size of the particle therapy system relative to systems that implement scanning external to the gantry.

In some implementations, one or more the scanning magnets described herein may be superconducting. For example, one or more, including all, of the scanning magnets downstream of the output channel may be superconducting. For example, one or more, including all, of the scanning magnets within the beamline structure may be superconducting. In this regard, it can be difficult to move the particle beam accurately in the presence of high magnetic fields such as those found in the beamline structure. Use of a superconducting magnet for scanning enables generation of magnetic fields of 2.5 T or greater or 3 T or greater to move the particle beam, which can overcome effects on the particle beam of the high magnetic fields, such as 2.5 T or greater or 3 T or greater, produced by the beamline structure.

Figure 11:
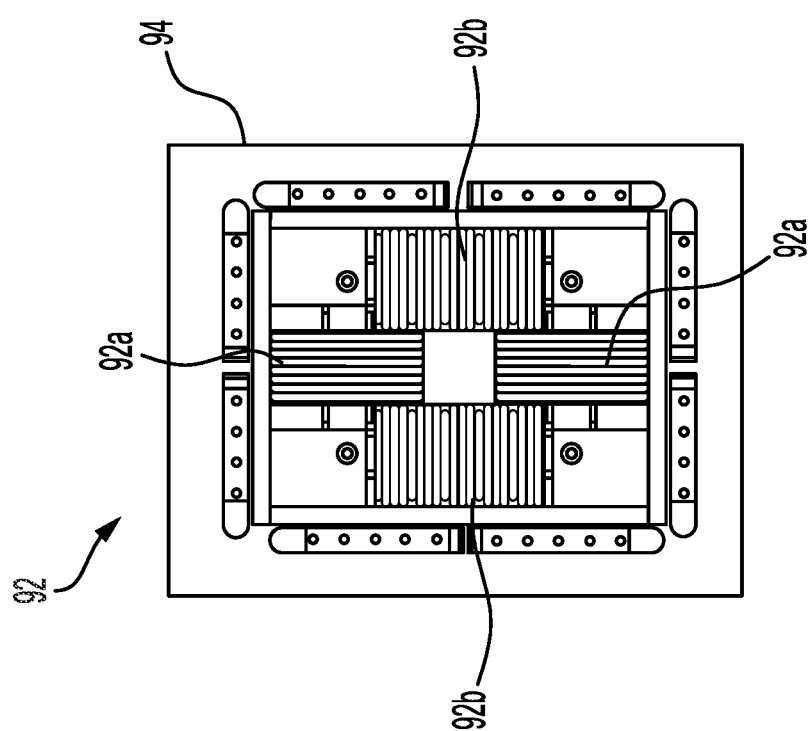
FIG. 11 is an illustration of a front view of an example superconducting scanning magnet configured to scan a particle beam in two orthogonal dimensions.

FIG. 11 shows an example implementation of a superconducting scanning magnet 92 configured to move the particle beam in two dimensions, which may be used in the scanning implementations described herein. In this example, scanning magnet 92 may have the same construction and operation as scanning magnet 43 shown of FIG. 5. Superconducting magnet 92 includes sets of high-temperature superconducting coils 92a and 92b, which are similar in construction to coils 46 and 45, respectively, of FIG. 5. Examples of high-temperature superconductors include, but are not limited to, YBCO (yttrium barium copper oxide) and BSCCO (bismuth strontium calcium copper oxide). Scanning magnet 92 is contained in a cryostat 94 that maintains the superconducting magnet at superconducting temperatures, e.g., above 77° Kelvin (K) or above 90° K. A cryostat may include a device configured to maintain the superconducting coils at cryogenic temperatures. The cryostat may maintain temperature by thermally isolating the superconducting coils from room temperature. This generally is performed using vacuum insulation, thermal radiation shields and/or superinsulation to reduce radiation heat transfer, and low thermal conductivity connections between room temperature and cryogenic temperatures. In some examples, liquid helium may be used to cool the coils to superconducting temperatures in the cryostat using, for example, conductive or immersive cooling. In conductive cooling, heat is transferred away from the superconducting coils using a thermal conductor. In immersive cooling, the superconducting coils may be in direct contact with a cryogen, such as liquid helium. In operation, current is applied to coils 92a and 92b to generate the magnetic fields used for scanning.

Figure 12B:
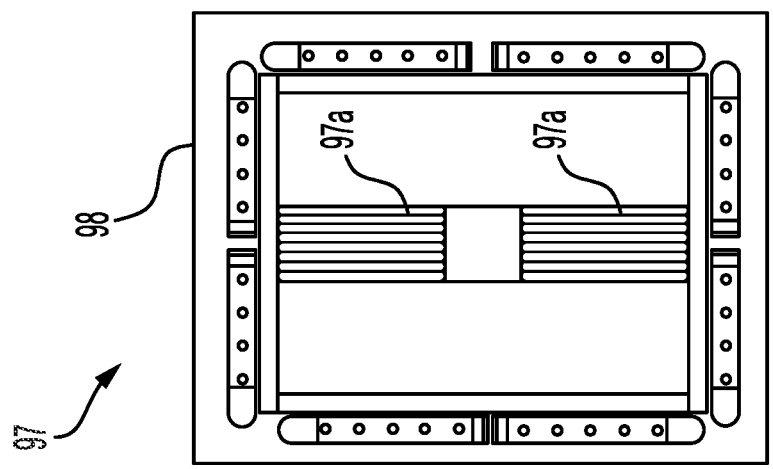
FIG. 12*b* is an illustration of a front view of an example superconducting scanning magnet configured to scan a particle beam in a single dimension orthogonal to the dimension of FIG. 12*a*.
Figure 12A:
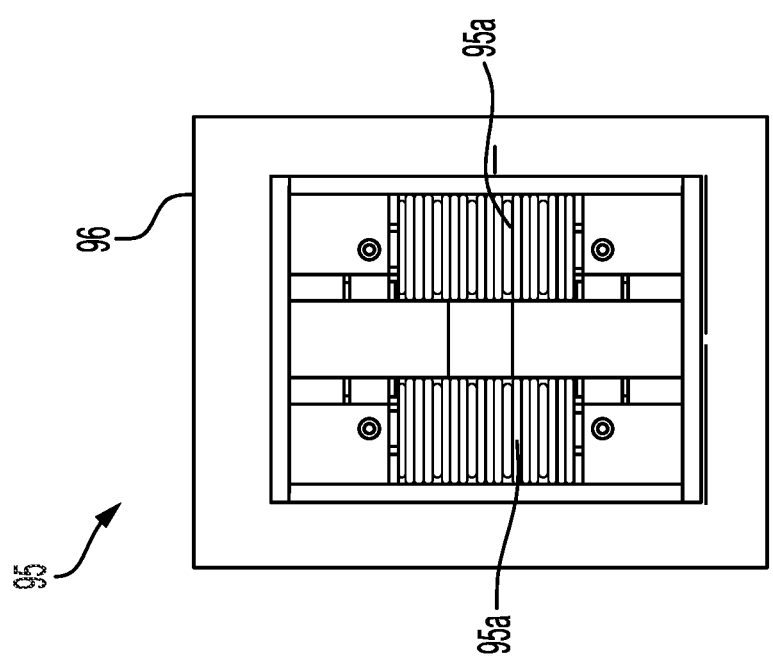
FIG. 12*a* is an illustration of a front view of an example superconducting scanning magnet configured to scan a particle beam in a single dimension.

FIG. 12a shows an example of a superconducting magnet 95 configured to move the particle beam in one dimension only, which may be used in scanning implementations described herein. The superconducting magnet includes high-temperature superconducting coil set 95a, which is configured to move the particle beam in one dimension only (for example, the Cartesian X or Y dimension). Examples of high-temperature superconductors include, but are not limited to, YBCO and BSCCO. Superconducting magnet 95 is contained in a cryostat 96 that maintains the superconducting magnet at superconducting temperatures, e.g., above 77° Kelvin (K). For example, liquid helium may be used to cool the coils to superconducting temperatures. Current is applied to coils 95a to generate the magnetic fields used for scanning. FIG. 12b shows an example of a superconducting scanning magnet 97 configured to move the particle beam in one dimension only. That dimension is different from, such as orthogonal to, the dimension that magnet 95 of FIG. 12a moves the particle beam. Superconducting magnet 97 includes high-temperature superconducting coil set 97a, which is configured to move the particle beam one dimension only (for example, the Cartesian X or Y dimension). Examples of high-temperature superconductors include, but are not limited to, YBCO and BSCCO. Superconducting magnet 95 is contained in a cryostat 98 that maintains the superconducting magnet at superconducting temperatures, e.g., above 77° Kelvin (K). For example, liquid helium may be used to cool the coils to superconducting temperatures. Current is applied to coils 97a to generate the magnetic fields used for scanning.

Figure 23:
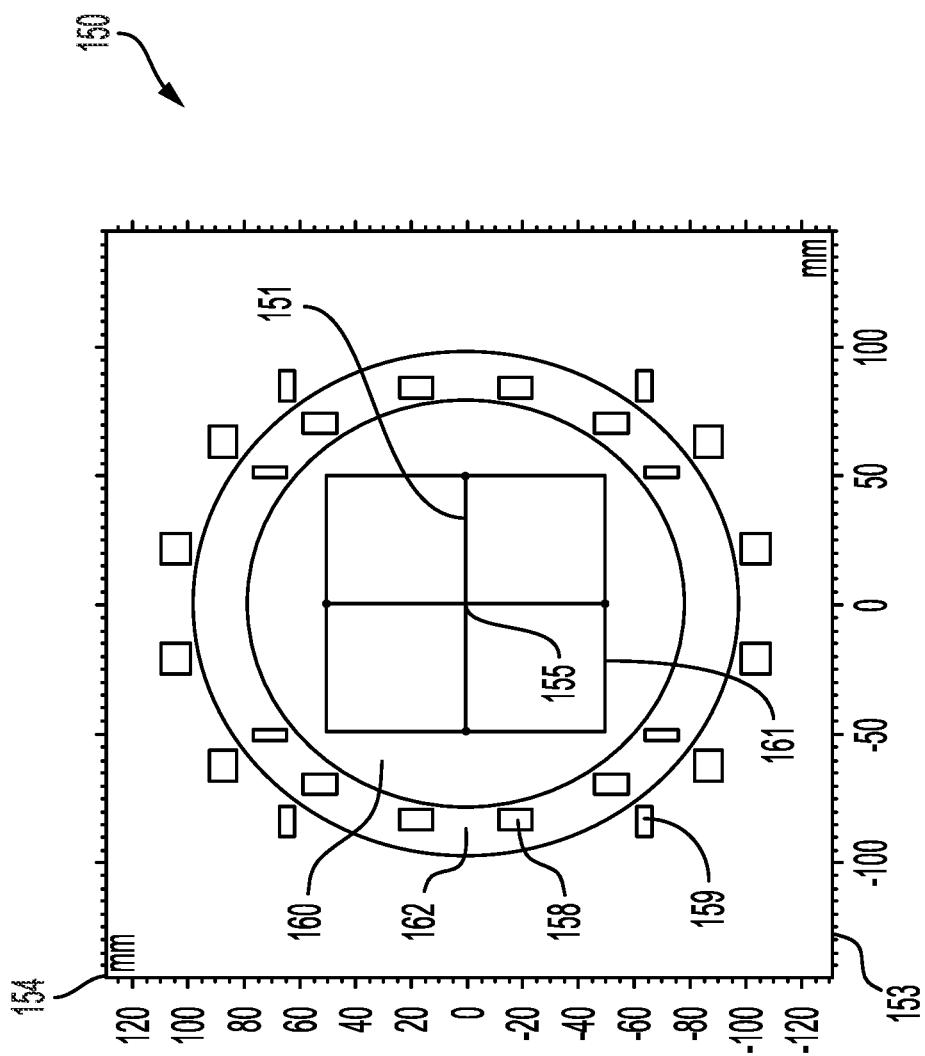
FIG. 23 is a front, cut-away view of an example superconducting magnet that may be used as a scanning magnet in the particle therapy system of claim 1.

FIG. 23 shows a front, cut-away view of another example implementation of a superconducting scanning magnet 150 configured to move the particle beam in two dimensions, which may be used in the scanning implementations described herein. In this example, scanning magnet 150 may be contained in a cryostat (not shown) such as that described above to maintain the superconducting magnet at superconducting temperatures, e.g., between 30° K and 40° K in this example, although the cryostat is not limited to these temperatures. A cryocooler may be used to maintain the temperature of the cryostat at superconducting temperatures. A cryocooler includes a device for providing active cooling of the superconducting coils down to cryogenic temperatures. The cryocooler may be controlled by the control systems described herein.

In FIG. 23, grid 151 shows the scanning beam aperture in both the Cartesian X and Y dimensions, 153 and 154, respectively. For example, grid 151 shows that scanning magnet 150 can move the particle beam ±5 cm in the X dimension and ±5 cm in the Y dimension relative to a reference 0,0 point 155. In other implementations, the scanning magnet may be configured to move the particle beam over lengths that are more or less than ±5 cm in the X dimension and ±5 cm in the Y dimension. In FIG. 23, sets of superconducting coils 158 and 159 are wound around an electrically nonconductive or an electrically non-superconducting material 160 to create aperture 161 that contains grid 151. Inner superconducting coils 158 may be separated from outer superconducting coils 159 by an electrically nonconductive or an electrically non-superconducting material 162. Superconducting coils 158 may be configured so that the magnetic fields generated thereby are orthogonal to the magnetic fields generated by superconducting coils 159. And, superconducting coils 159 may be configured so that the magnetic fields generated thereby are orthogonal to the magnetic fields generated by superconducting coils 158. For example, the windings of superconducting coils 158 and 159 may be orthogonal to each other. In some implementations, the magnetic fields generated by superconducting coils 158 and 159 need not be orthogonal, but rather may be different—for example, at an angle to each other that is less than 90°—yet still enable scanning in a grid such as grid 151.

In this example, superconducting coils 158 control movement of the particle beam in the X dimension. For example, current runs through those superconducting coils to produce a magnetic field. The strength of that magnetic field is proportional to the amount of current running through the superconducting coils. And, the strength of the magnetic field is proportional to the amount that the particle beam moves in the X dimension during scanning. In this example, superconducting coils 159 control movement of the particle beam in the Y dimension. For example, current runs through those superconducting coils to produce a magnetic field. The strength of that magnetic field is proportional to the amount of current running through the superconducting coils. And, the strength of the magnetic field is proportional to the amount that the particle beam moves in the X dimension during scanning. Current may run through superconducting coils 158 and 159 at the same time to produce a cumulative magnetic field that moves the particle beam in both the X and Y dimensions. Current may run through superconducting coils 158 and 159 at different times so that the particle beam moves in the X or Y dimensions at separate times, but still reaches a target location.

An example of electrically non-superconducting material that may be included in scanning magnet 150 is copper; however, scanning magnet 150 is not limited to use with copper. The electrically non-superconducting material promote heat dissipation, for example during a quench of the superconducting coils 158 and 159.

Figure 24:
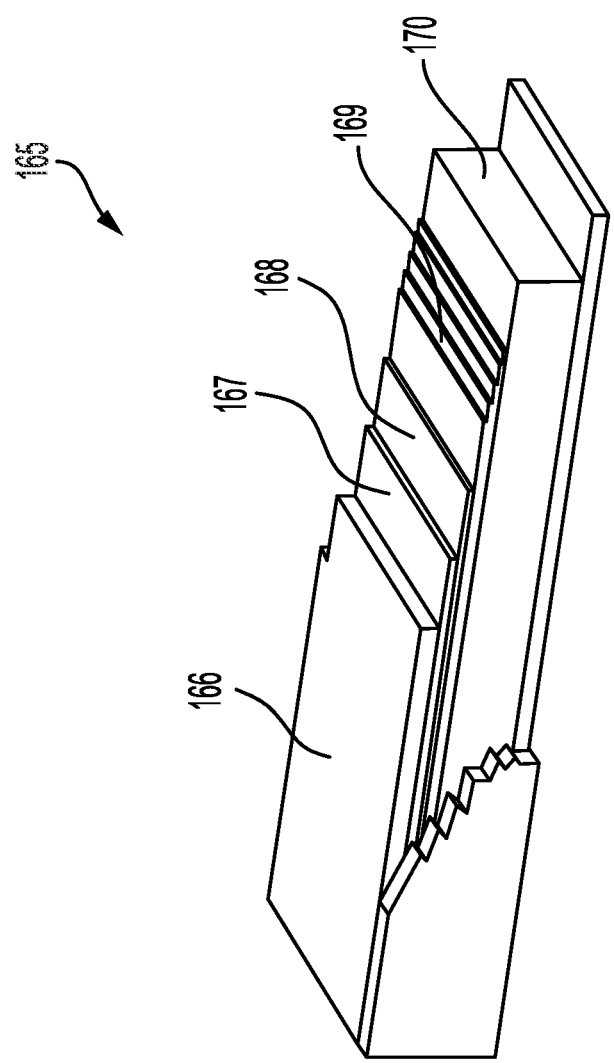
FIG. 24 is a cut-away view of an example superconducting coil that may be used in the superconducting magnet of FIG. 23.

FIG. 24 shows a cross-section of an example superconducting coil 165 that may be used to implement each of superconducting coils 158 and 159. Superconducting coil 165 includes a copper (Cu) stabilization layer 166 that encases or surrounds the other layers of superconducting coil 165. Superconducting coil 165 also includes a silver (Ag) cap layer 167, a rare-earth barium copper oxide (ReBCO) superconducting layer 168 (or layer(s) of other high-temperature superconducting material(s)) adjacent to and in contact with the silver cap layer, a buffer layer stack 169 adjacent to and in contact with the ReBCO superconducting layer to prevent interdiffusion between oxides and a metal substrate, and a substrate layer 170 adjacent to and in contact with the buffer layer stack. Examples of materials that may be included in the substrate layer include, but are not limited to, an electrically-conductive metal such as copper, nickel, or aluminum. Examples of materials that may be included in the buffer layer stack include, but are not limited to, $SrRuO_3$ (strontium ruthenate—SRO) and $LaNiO_3$ (LNO). Superconducting coil 165 may have a different configuration than that shown or may include different materials than those shown. For example, the copper stabilization layer may be omitted or a material other than copper may be used. Other types of superconducting materials may be used, such as YBCO and/or BSCCO.

Referring back to FIG. 3, output channel 17 portion of beamline structure 16 includes large-aperture superconducting magnetic dipole 31 arranged in series with large-aperture superconducting magnetic dipole 32. Examples of large apertures include, but are not limited to 20 cm by 20 cm. Located between magnetic dipole 31 and magnetic dipole 32 are multiple large-aperture superconducting magnetic quadrupoles 33, 34, and 35. In this example, magnetic quadrupoles 33, 34, and 35 include, alternately, one or more focusing magnets and one or more defocusing magnets to focus and defocus the particle beam, respectively, in order to maintain a substantially consistent cross-sectional area of the particle beam. In this regard, the net effect on the particle beam passing through the alternating magnetic field gradients of the magnetic quadrupoles is to cause the beam to converge; that is, to focus. In some implementations, magnetic quadrupole 33 includes a defocusing magnet, magnetic quadrupole 34 includes a focusing magnet, and magnetic quadrupole 35 includes a defocusing magnet. In some implementations, magnetic 33 includes a focusing magnet, magnetic quadrupole 34 includes a defocusing magnet, and magnetic quadrupole 35 includes a focusing magnet. In some implementations, output channel 17 may include different numbers of magnetic quadrupoles in different configurations and/or a different number of magnetic dipoles in a different configuration. In some implementations, output channel 17 may include higher-order magnetics, such as sextupoles, in place of, or in addition to, the magnetic quadrupoles that are shown.

In some implementations, output channel 17 is configured to bend the particle beam in the presence of magnetic fields of 2.5 T, 3 T, or greater in the beamline structure. For example, the magnetic fields may be generated by running current through one or more coils in the magnets in the beamline structure, which may be on the order of 2.5 T or more, 3 T or more, 4 T or more, 5 T or more, 6 T or more, 7 T or more, 8 T or more, 9 T or more, 10 T or more, 11 T or more, 12 T or more, 13 T or more, 14 T or more, or 15 T or more. In the presence of magnetic fields such as these, the magnetics in output channel 17 are configured to produce a combined total bending angle of the particle beam anywhere in a range from 90° to 170°—for example, 90°, 95°, 100°, 105°, 110°, 115°, 120°, 125°, 130°, 135°, 140°, 145°, 150°, 155°, 160°, 165°, or 170°. Alternatively, in some implementations, output channel 17 is configured to bend the particle beam at a combined total bending angle that is less than 90° or that is greater than 170°—for example, 180° or greater. In FIGS. 1 to 3, output channel 17 is configured to bend the particle beam at a combined total bending angle of about 150° relative to line 38. To achieve a bending magnitude having a value from 110° to 170°, magnetic dipole 31 may be configured to bend the particle beam within a range of 20° to 85° relative to line 38, and magnetic dipole 32 may be configured to bend the particle beam within a range of 20° to 85° relative to horizontal line 38.

In some implementations, output channel 17 may include different numbers of magnetic structures in different configurations. For example, output channel 17 may include a magnetic dipole of the type described herein, followed by three alternating magnetic quadrupoles of the type described herein, followed by a magnetic dipole, followed by three alternating magnetic quadrupoles of the type described herein, followed by a magnetic dipole of the type described herein. Additional magnetics may be used, for example, to change where and by how much the particle beam bends. Additional magnetic structures may also be used to focus the particle beam over longer distances. Conversely, fewer numbers of magnetic structures may be used to focus the particle beam over shorter distances, as shown in FIG. 1 for example.

A nozzle 40 (FIG. 1) is located at the output or exit of output channel 17. In the example of FIG. 1, nozzle 40 is connected to output channel 17 and, where applicable, moves along with output channel. Nozzle 40 may, or may not, be considered to be part of the compact gantry. Nozzle 40 is an example of a particle beam output device. In this example, nozzle 40 receives the particle beam from output channel 17 and, in some implementations, conditions the particle beam for output to an irradiation target, such as a tumor in a patient, at the treatment position or isocenter. In this regard, as noted, output channel 17 bends the particle beam by at least 90°. The particle beam is thus directed towards the treatment position or isocenter as it exits output channel 17. In addition, as described herein, scanning magnet(s) 30 may move the particle beam within a plane to move the particle beam across the irradiation target.

In this regard, as explained previously, the nozzle may contain one or more scanning magnets. The energy degrader is downstream of the scanning magnets and the collimator is downstream of the scanning magnets. In FIGS. 2 and 3, energy degrader 41 receives the scanning or moving particle beam from the scanning magnet(s). In this example, energy degrader 41 is mounted to gantry 14 (via nozzle 40) between output channel 17 and the irradiation target at treatment position 19. Energy degrader 41 is configured to, and controllable to, change an energy of the particle beam before the particle beam reaches the irradiation target. In some implementations, the energy degrader is the sole mechanism by which to actively control the change in energy of the particle beam prior to the particle beam reaching the irradiation target. In some implementations, the energy of the particle beam is not actively controllable after the particle beam is output by the particle accelerator and prior to the particle beam reaching the energy degrader. For example, in such implementations, components of the gantry between the particle accelerator and the energy degrader do not, and are not configured to, actively control the beam energy. Stated yet another way, the gantry or the beamline conduit thereof is not configured to actively control the particle beam after the particle beam is output by the particle accelerator and prior to the particle beam reaching the energy degrader. In some cases, there may be some incidental changes in energy caused by movement through the beamline structure; however, those changes are not actively controlled.

As noted previously, the particle beam output by the accelerator may be monoenergetic and the energy degrader is the only/sole or primary vehicle for changing beam energy during treatment of an irradiation target. A monoenergetic particle beam includes a particle beam having a single, fixed energy level, such as 100 MeV, 150 Mev, 200 Mev, 250 Mev, and so forth. A monoenergetic particle beam may deviate from the fixed energy level by a predetermined amount, such as ±10%, ±5%, ±2%, or ±1%, and still be considered monoenergetic. Switching operation of the accelerator during treatment, as is required to switch particle beam energies during treatment, may produce excess stray neutrons, resulting in the need for increased shielding and reducing beamline efficiency. The neutrons may be generated by the particle accelerator and/or by magnetics along the beamline structure. By using a particle beam that is monoenergetic during treatment and relying on the energy degrader to change beam energy, production of stray neutrons may be reduced or minimized and the efficiency of the beamline structure may be increased.

In an example, the energy degrader may include plates that are movable into or out of a path of the particle beam. In another example, the energy degrader may include wedges that overlap at least in part and that are movable within a path of the particle beam. An example wedge is a polyhedron defined by two triangles and three trapezoidal faces. In either configuration, variable amounts of material are movable into the path of the particle beam. The material absorbs energy from the particle beam, resulting reduced-energy beam output. The more material there is in the path of the particle beam, the less energy that the particle beam will have. In some implementations, the energy-absorbing structures are movable across all of the beam field or across only part of the beam field. As noted, in some examples, the beam field includes the maximum extent that the particle beam can be moved across a plane parallel to the treatment area on a patient for a given position of the compact gantry.

Figure 22:
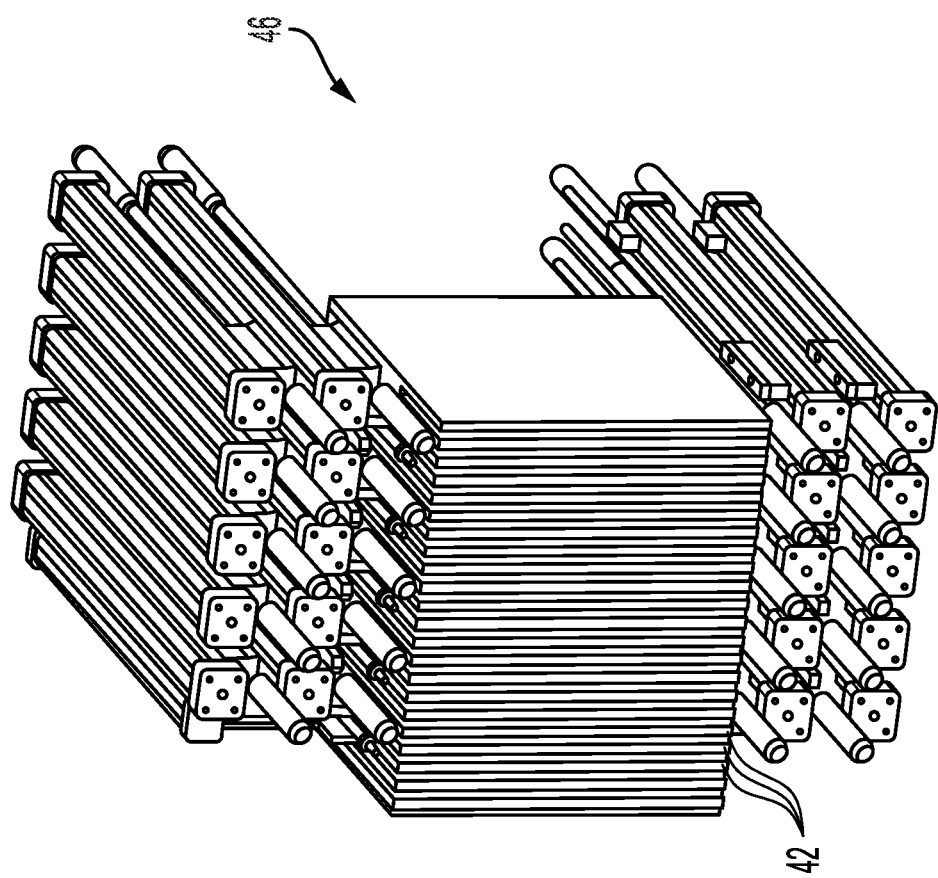
FIG. 22 is a perspective view of an example energy degrader.

Referring to FIG. 22, in an example, energy degrader 48 is a range modulator that is controllable to move structures 42 into, and out of, the path of the particle beam to change the energy of the particle beam and therefore the depth to which dose of the particle beam will be deposited in the irradiation target. Examples of such energy-absorbing structures include, but are not limited to, plates; polyhedra such as wedges, tetrahedra, or toroidal polyhedra; and curved three-dimensional shapes, such as cylinders, spheres, or cones. In this way, the energy degrader can cause the particle beam to deposit doses of radiation in the interior of an irradiation target to treat layers or columns of the target. In this regard, when protons at a particular energy move through tissue, the protons ionize atoms of the tissue and deposit a dose primarily at a predefined tissue depth corresponding to that energy. The energy degrader thus is configured to move the particle beam in the Cartesian Z dimension through the target, thereby enabling the scanning magnet to perform scanning in a third dimension (Cartesian Z) in addition the Cartesian X and Y dimensions. In some implementations, an energy absorbing structure of the energy degrader, such as a plate or wedge, may be configured to move during movement (scanning) of the particle beam and track or trail the particle beam during movement. An example energy degrader that tracks or trails particle beam movement is described in U.S. Pat. No. 10,675,487 (Zwart) entitled "High-Speed Energy Switching". The content of U.S. Pat. No. 10,675,487, particularly the content related to the energy degrader that tracks or trails particle beam movement (e.g., FIGS. 36 to 46 of U.S. Pat. No. 10,675,487 and the accompanying description), is incorporated herein by reference.

The Bragg peak is a pronounced peak on the Bragg curve that plots the energy loss of ionizing radiation during travel through tissue. The Bragg peak represents the depth at which most radiation deposits within tissue. For protons, the Bragg peak occurs right before the particles come to rest. Accordingly, the energy of the particle beam may be changed to change the location of its Bragg peak and, therefore, where a majority of the dose of protons will deposit in depth in the tissue. In this regard, the particle accelerator may be a fixed-energy particle accelerator. In a fixed-energy particle accelerator, the particle beam always exits the particle accelerator at the same, or about the same, energy—for example, within a 10%, 5%, or 1% deviation or less from an expected or target energy. In a fixed-energy particle accelerator, the energy degrader is the primary vehicle or the sole vehicle for varying the energy of the beam applied to an irradiation target in the patient. In some implementations, the particle accelerators described herein are configured to output particle beams at a single energy or at two or more energies within a range between about 100 MeV and about 300 MeV (for example, between 115 MeV and 250 MeV). The fixed energy output may be within that range (e.g., 250 MeV) or, in some examples, above or below that range.

In some implementations, the particle accelerator is a dual-energy accelerator. In a dual-energy particle accelerator, the particle beam exits the particle accelerator at one of two different energy levels—a high energy level or a low energy level. The terms "high" and "low" have no specific numerical connotations but rather are intended to convey relative magnitudes. In some implementations, the particle accelerators described herein are configured to output particle beams at two energies that are within a range that is between about 100 MeV and about 300 MeV. The high energy output and the low energy output may be values within that range or, in some examples, above or below that range. The energy degrader described herein may be used with dual-energy particle accelerators in order to reduce the energy of the particle beam below one of the two energy levels and/or to finely adjust between the two energy levels.

In the figures (FIGS. 2, 3), nozzle 40 also includes a collimator 44 downstream of energy degrader 41 relative to the particle accelerator (that is, closer to the irradiation target). In an example, a collimator is a structure that is controllable to allow some radiation to pass to a target and to block some radiation from passing to the patient. Typically, the radiation that passes is directed to an irradiation target to be treated, and the radiation that is blocked would otherwise hit, and potentially damage, healthy patient tissue. In operation, the collimator is placed in the radiation path between output channel 17 and the irradiation target and is controlled to produce an opening of an appropriate size and shape to allow some radiation to pass through the opening to the irradiation target, while a remainder of the structure blocks some radiation from reaching adjacent tissue.

The collimator may be configurable—for example, its aperture may be controlled and changed during treatment. The collimator may be fixed or not changeable. For example, the collimator may have a fixed shape that cannot be altered.

In some implementations, components of an example configurable collimator include multiple leaves that are dynamically reconfigurable during movement of the particle beam to change a shape of an edge defined by the multiple leaves. The edge is movable between at least a portion of the particle beam and a target of the particle beam so that a first part of the particle beam on a first side of the edge is at least partly blocked by the multiple leaves and so that a second part of the particle beam on a second side of the edge is allowed to pass to the target.

Figure 14:
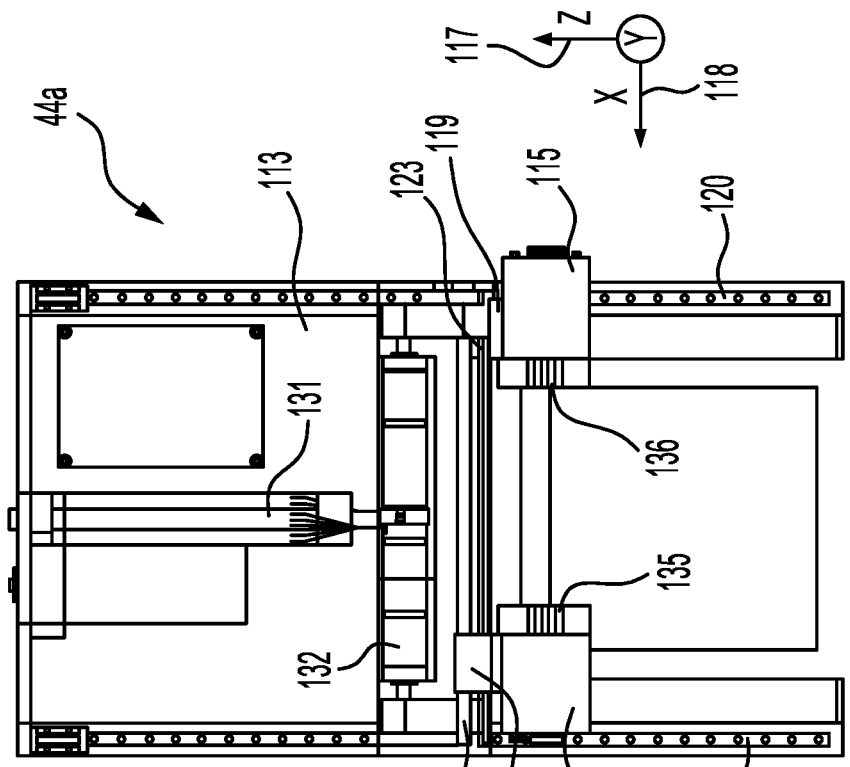
FIG. 14 is a drawing showing a front, partially-transparent view of the configurable collimator of FIG. 13.
Figure 13:
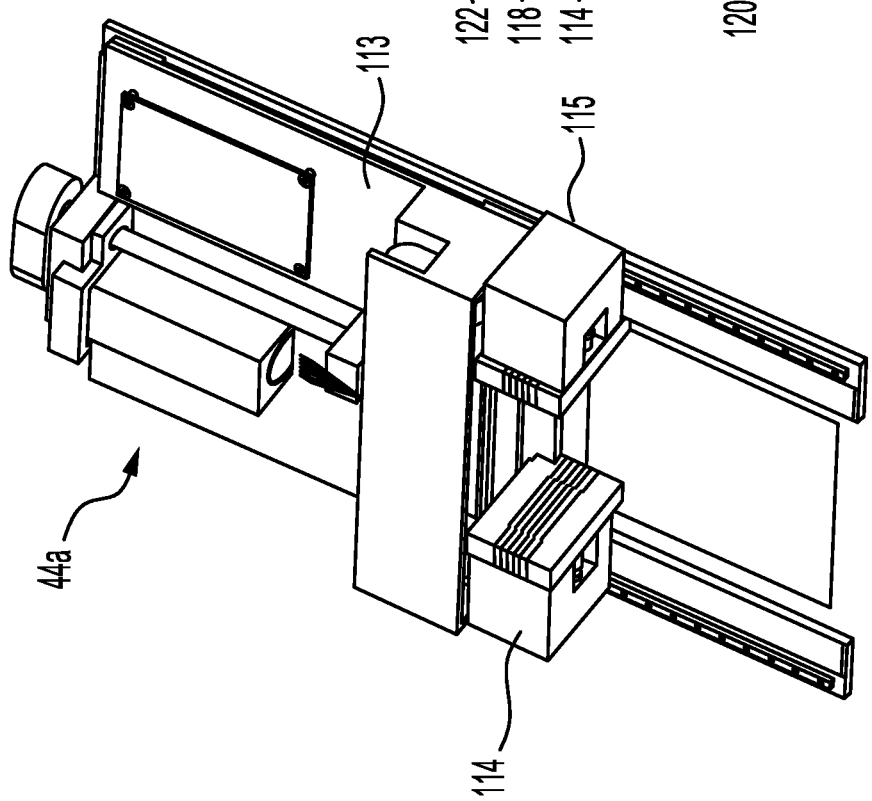
FIG. 13 is a drawing showing a perspective view of an example configurable collimator that may be part of the particle therapy system of claim 1.
Figure 15:
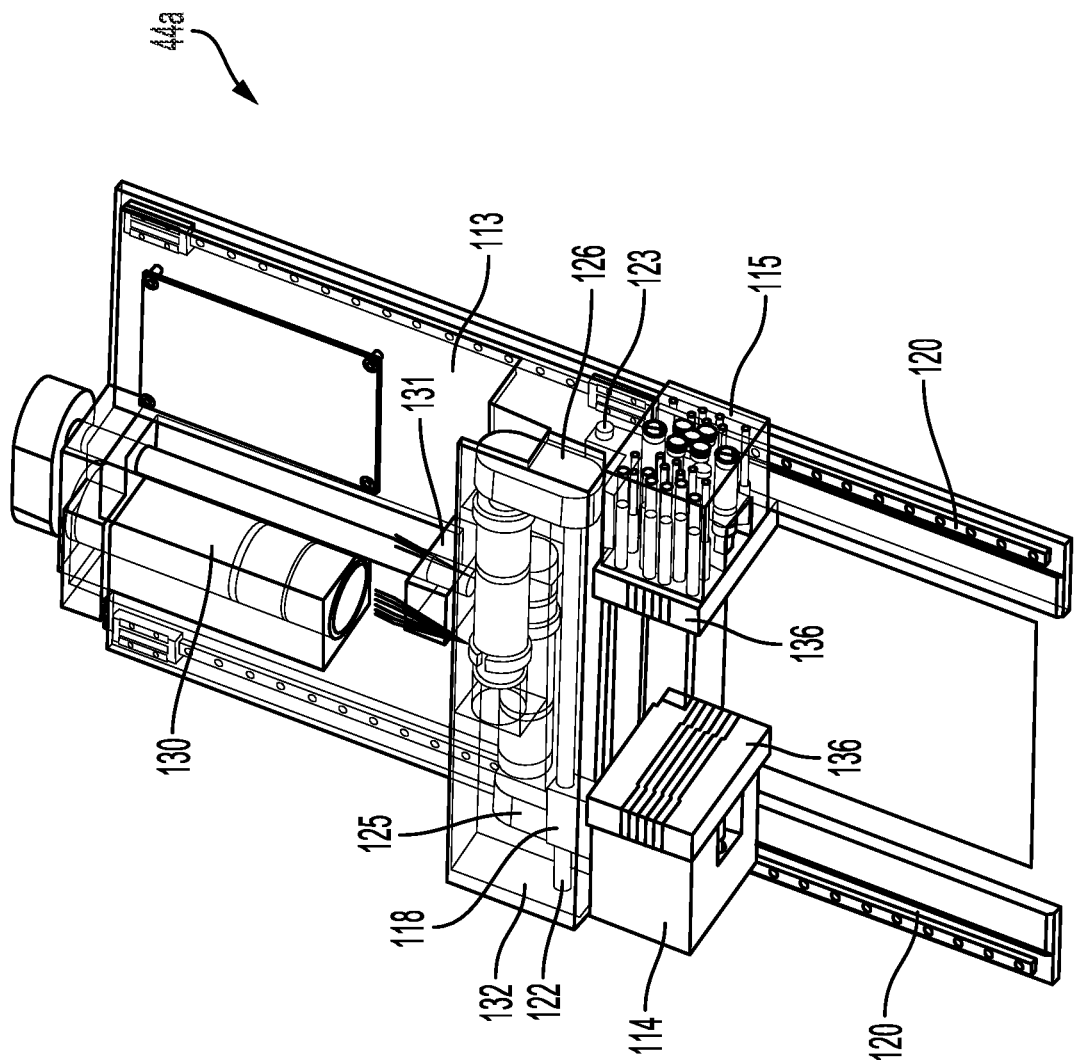
FIG. 15 is a drawing showing a perspective, partially-transparent view of the configurable collimator of FIGS. 13 and 14.

FIGS. 13, 14, and 15 show an example implementation of configurable collimator 44a, which may be used with the particle therapy system described herein. Collimator 44a including carriages 113, 114, and 115 configured to hold, and to move, the leaves described above both vertically and horizontally relative to an irradiation target. As shown, vertical movement includes movement in the Cartesian Z-dimension 117, and horizontal movement includes movement in the Cartesian X dimension 118 (with the Cartesian Y dimension being into, or out of, the page in FIGS. 13 and 14). FIGS. 14 and 15 show parts of carriage housings as transparent in order to show components inside the housings; however, the housings are not actually transparent.

Carriage 113 is referred to herein as the primary carriage, and carriages 114 and 115 are referred to herein as secondary carriages. Secondary carriages 114, 115 are coupled to primary carriage 113, as shown in FIGS. 13 to 15. In this example, secondary carriages 114, 115 each include a housing that is fixed to primary carriage 115 via a corresponding member 118, 119. In this example, primary carriage 113 is movable vertically (the Z dimension) relative to the irradiation target and relative to particle accelerator along tracks 120. The vertical movement of primary carriage 113 also causes the secondary carriages to move vertically. In some implementations, the secondary carriages move vertically in concert.

As shown in FIGS. 13 to 15, each secondary carriage 114, 115 is connected to a corresponding rod or rail 122, 123, along which the secondary carriage moves. More specifically, in this example, motor 125 drives secondary carriage 114 to move along rod 122 towards or away from secondary carriage 115. Likewise, in this example, motor 126 drives secondary carriage 115 to move along rod 123 towards or away from secondary carriage 114. Control over movement of the primary and secondary carriages is implemented to position the leaves relative to the irradiation target, as described herein. In addition, the leaves themselves are also configured to move in and out of the carriages, as also described herein.

As shown in FIG. 15, a motor 130 drives the vertical movement of primary carriage 113. For example, as shown in FIG. 15, lead screw 131 is coupled to housing 132, which holds motors 125, 126 that drive corresponding secondary carriages 114, 115, and which is mounted on tracks 120. Lead screw 131 is coupled to, and driven vertically by, motor 130. That is, motor 130 drives lead screw 131 vertically (the Cartesian Z dimension). Because lead screw 131 is fixed to housing 132, this movement also causes housing 132, and thus secondary carriages 114, 115, to move along tracks 120, either towards or away from the irradiation target.

In this example implementation, seven leaves 135, 136 are mounted on each secondary carriage 114, 115. Each secondary carriage may be configured to move its leaves horizontally into, or out of, the treatment area. Using linear motors, the individual leaves on each secondary carriage may be independently and linearly movable in the X dimension relative to other leaves on the same secondary carriage. In some implementations, the leaves may also be configured to move in the Y dimension. Furthermore, the leaves on one secondary carriage 114 may be movable independently of the leaves on the other secondary carriage 115. These independent movements of leaves on the secondary carriages, together with the vertical movements enabled by the primary carriage, allow the leaves to be moved into various configurations. As a result, the leaves can conform, both horizontally and vertically, to treatment areas that are randomly shaped both in horizontal and vertical dimensions. The sizes and shapes of the leaves may be varied to create different conformations. For example, the sizes and shapes may be varied to treat a single beam spot and, thus, a single column. In some implementations individual leaves on each secondary carriage may be independently and linearly movable using electric motors that drive lead screws in the X dimension relative to other leaves on the same secondary carriage.

The leaves may be made of any appropriate material that prevents or inhibits transmission of radiation. The type of radiation used may dictate what material(s) are used in the leaves. For example, if the radiation is X-ray, the leaves may be made of lead. In the examples described herein, the radiation is a proton or ion beam. Accordingly, different types of metals or other materials may be used for the leaves. For example, the leaves may be made of nickel, tungsten, lead, brass, steel, iron, or any appropriate combinations thereof. The height of each leaf may determine how well that leaf inhibits transmission of radiation.

Implementations of the configurable collimator described with respect to FIGS. 13 to 15 are described in U.S. Patent Publication No. 2017/0128746 (Zwart) entitled "Adaptive Aperture". The content of U.S. Patent Publication No. 2017/0128746, particularly the content relating to the description of the adaptive aperture (e.g., FIGS. 1 to 7 of U.S. Patent Publication No. 2017/0128746 and the accompanying description), is incorporated herein by reference.

Referring back to FIG. 1, as noted, example particle therapy system include an isocentric gantry that is compact in size, which reduces overall system size. In implementations of compact gantry 14, the diameter of support structure 15 may be less than 6 meters (m), less than 5 m, or less than 4 m. In an example, the diameter of support structure 15 is 4.8 m. The length of the beamline structure may be measured from, and equal to the distance between, the output of the accelerator and the system isocenter. In implementations of compact gantry 14, the length of beamline structure 16 may be less than 6 meters (m), less than 5 m, less than 4.5 m, or less than 4 m. In an example, the length of beamline structure 16 is 4.2 m (FIG. 2). In this regard, the distance between the particle accelerator and the system isocenter or treatment position may be less than 6 m, less than 5 m, less than 4.5 m, or less than 4 m. In implementations of compact gantry 14, the distance between the output of output channel 17 and the system isocenter or the treatment position is 2 m or less, 1.5 m or less, or 1 m or less. In implementations of compact gantry 14, the distance between the output of output channel 17 and the system isocenter or the treatment position is between 0.8 m and 1.4 m. In an example, the distance between the output of output channel 17 and the system isocenter or the treatment position is 1.01 m. Other implementations may have different dimensions than those listed here.

In some implementations, the particle therapy system has a footprint of 93 square meters ($m^2$) or less or of 75 $m^2$ or less. In some implementations, the particle therapy system is configured to fit within a vault designed for a LINAC. For example, the components of FIGS. 1 to 3 may be small enough fit within, and have dimensions that fit within, a vault having the following dimensions: 25 feet (7.62 m) or less in length, 20 feet (6.09 m) or less in width, and 11 feet (3.35 m) or less in height. For example, the components of FIGS. 1 to 3 may be small enough fit within, and have dimensions that fit within, a vault having the following dimensions: 25 feet (7.62 m) or less in length, 26 feet (7.92 m) or less in width, and 10 feet (3.05 m) or less in height. For example, the components of FIGS. 1 to 3 may be small enough fit within, and have dimensions that fit within, a LINAC vault having a footprint of 26.09 feet (11 m) or less by 29.62 feet (9 m) or less, with a height of 16.40 feet (5 m) or less. However, as noted, some implementations of the particle therapy system may have different dimensions including, but not limited to, diameters, heights, widths, and lengths. In some implementations, the ceiling of a preexisting LINAC vault may not be high enough to support full 360° rotation of or around the gantry. In such implementations, a pit 90 (FIG. 1) may be dug beneath the floor of the LINAC vault to enable the rotation.

Figure 16:
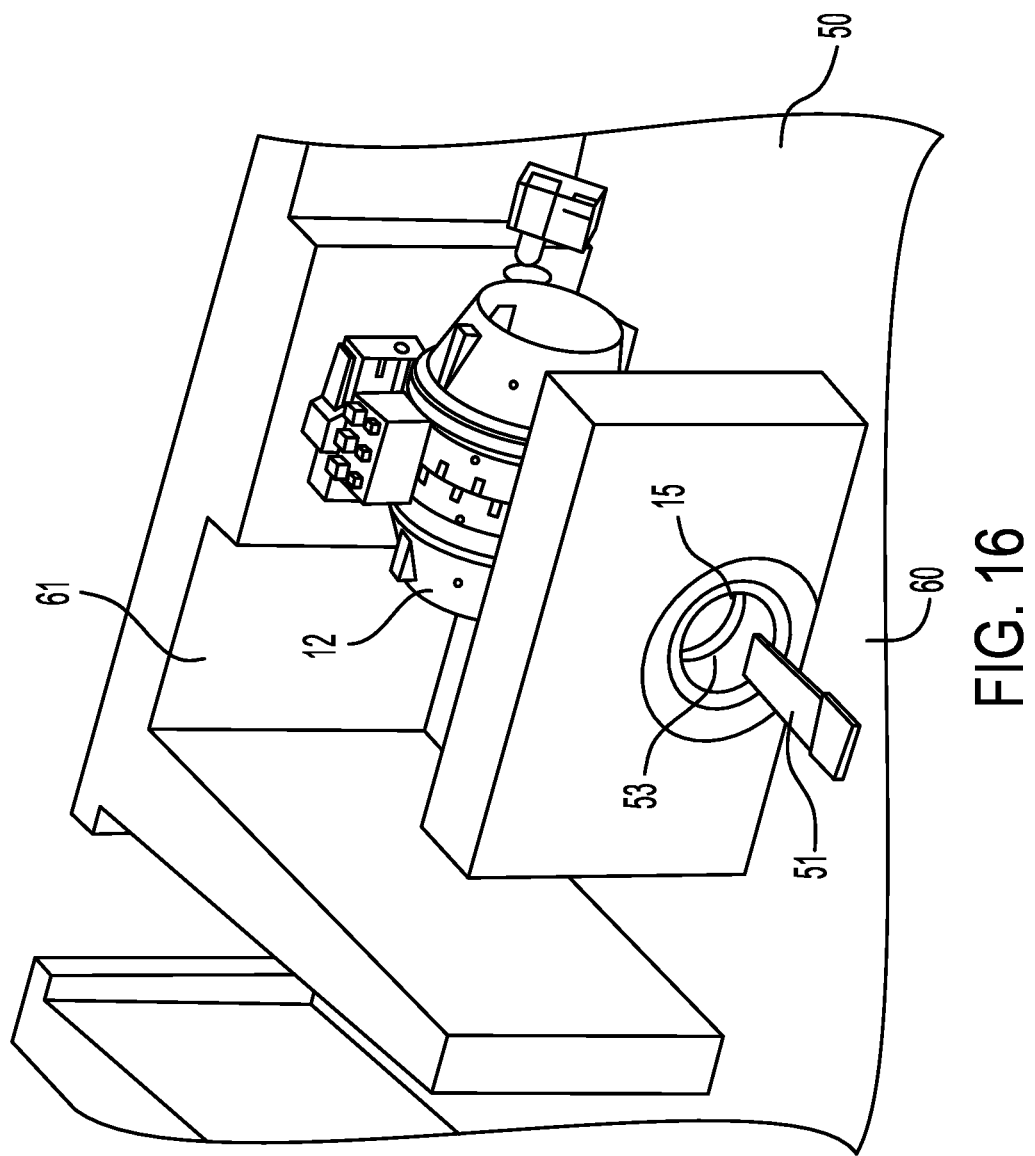
FIG. 16 is a block diagram of an example treatment space that is configured to house all or part of the particle therapy system of FIG. 1.

FIGS. 1 and 16 shows examples of treatment spaces 49 and 50 in which particle therapy system 10 and its variants may be housed. The treatment spaces are implemented in LINAC vaults in these examples, which may be shielded using lead or other appropriate materials such as concrete, borated polyethylene, and/or steel. In this regard, particles, such as protons, that are created by the particle accelerator but do not reach the irradiation target create secondary radiation through the production of high energy neutrons. In an example, particle accelerator 12 and/or gantry generates 10 millisieverts or less of such neutrons per gray of dose delivered by the particle beam.

Use of a monoenergetic particle bean and reliance on an energy degrader that is outside of the beamline structure enables the magnetics in the beamline to direct the beam efficiently. More specifically, changes in beam energy within the beamline increase production of stray neutrons and, therefore, losses of particle beam within the beamline, thereby degrading its efficiency. The monoenergetic particle beam used in the implementations of the systems described herein, combined with the magnetic structures in the beamline, may lead to increased efficiency. In some cases, decreases in the length of the beamline structure may also increase efficiency. In some implementations, the variants of the beamline structure described herein have an efficiency of 10% or more, 20% or more, 30% or more, 40% or more, 50% or more, 60% or more, 70% or more, 80% or more, or 90% or more. In some examples, efficiency is a measure of the percentage of particles output from the particle accelerator that are output from the beamline structure. So, an efficiency of 10% or more includes 10% or more of the particles output from the particle accelerator being output from the beamline structure; an efficiency of 20% or more includes 20% or more of the particles output from the particle accelerator being output from the beamline structure; an efficiency of 30% or more includes 30% or more of the particles output from the particle accelerator being output from the beamline structure; an efficiency of 40% or more includes 40% or more of the particles output from the particle accelerator being output from the beamline structure; an efficiency of 50% or more includes 50% or more of the particles output from the particle accelerator being output from the beamline structure; an efficiency of 60% or more includes 60% or more of the particles output from the particle accelerator being output from the beamline structure; an efficiency of 70% or more includes 70% or more of the particles output from the particle accelerator being output from the beamline structure; an efficiency of 80% or more includes 80% or more of the particles output from the particle accelerator being output from the beamline structure; and an efficiency of 90% or more includes 90% or more of the particles output from the particle accelerator being output from the beamline structure. In an example, the particle accelerator and gantry described herein transmit more than 70% of a proton beam to a patient even at energies in lower range of the accelerator.

Beamline efficiency of the type described herein enables a "single room" solution in which the particle accelerator, the gantry, and patient all reside with a single vault, as described above. Within this vault, the particle accelerator itself may include shielding, but separate compartments 60 and 61 (see FIG. 16) in the vault containing the patient and the particle accelerator, respectively, need not be shielded from each other. In other words, in some implementations, there is no electromagnetic shielding that is external to the particle accelerator and the gantry that separates the particle accelerator from the patient. Shielding may not be needed due to the low levels of neutrons emitted by the system. In some implementations, there may be minimal shielding between the separate compartments 60 and 61. For example, the shielding may be 30 cm or less in thickness, 20 cm or less in thickness, or 10 cm or less in thickness.

Referring also to FIG. 1, particle therapy system 10 also includes a treatment couch 51. Treatment couch 51 is configured to move relative to hole 53 in or through gantry 14 to position a patient at the system isocenter or treatment position. In this example, treatment couch 51 is mounted to a robotic arm 54. Arm 54 includes a first segment 55, a second segment 56, and third segment 57. First segment 55 is rotatably coupled to second segment 56 and second segment 56 is rotatably coupled to third segment 57. Treatment couch 51 is coupled to third segment 57 as shown in the figure. Arm 54 is controllable to move treatment couch 51 in and through hole 53 to position a patient lying on the couch for treatment; that is, to move the patient into the treatment position. In some implementations, arm 54 may position the patient in two degrees of freedom, in three degrees of freedom, in four degrees of freedom, in five degrees of freedom, or in six degrees of freedom. An example of two degrees of freedom is forward-backward movement and left-right movement; an example of three degrees of freedom is forward-backward movement, left-right movement, and up-down movement; an example of four degrees of freedom is forward-backward movement, left-right movement, up-down movement and one of pitch, yaw, or roll movement; an example of five degrees of freedom is forward-backward movement, left-right movement, up-down movement and two of pitch, yaw, or roll movement; and an example of six degrees of freedom is forward-backward movement, left-right movement, up-down movement, pitch movement, yaw movement, and roll movement. In some implementations, the treatment couch may be replaced by or include a couch that inclines at least in part or that is convertible to a chair, and that is still be controllable in two, three, four, five, or six degrees of freedom to position the patient for treatment. In some implementations, arm 54 may have a different configuration than that shown in FIG. 1. For example, arm 54 may have two segments or more than three segments. Hydraulics, robotics, or both, may control or implement non-planar movement of the treatment couch.

In some implementations, output channel 17 may rotate at least part-way, including all the way, around support structure 15 or output channel may remain fixed on support structure 15 and all or part of support structure 15 may rotate around the treatment position. In some implementations, output channel 17 may not rotate around support structure 15 and the support structure may not rotate around the patient. Instead, the output channel may remain stationary, thereby providing a particle beam that is fixed in one direction. In implementations such as these, the treatment couch or other seat moves relative to the fixed beam during treatment. In some system described herein, the location of the particle beam may be set through rotation of the gantry, after which the beam remains fixed except for scanning movements across the irradiation target and the treatment couch or other seat moves during treatment. In some implementations, treatment may be implemented using a combination of gantry movement and treatment couch (or other seat movement). For example, the output channel may be positioned and the beam may be fixed temporarily, during which time the treatment couch moves to implement treatment. After that, the output channel may be repositioned to fix the beam temporarily at a new position. Treatment may be implemented at the new position through couch movement. These operations may be repeated as defined by a treatment plan drafted for use with the particle therapy system.

Particle therapy system 10 may be an intensity-modulated proton therapy (IMPT) system. IMPT systems enable spatial control of circumscribed beams of protons that may have a variable energy and/or intensity. IMPT takes advantage of the charged-particle Bragg peak—as noted, the characteristic peak of dose at the end of particles' delivery range—combined with the modulation of particle beam variables to create target-local modulations in dose that achieve objectives set forth in a treatment plan. IMPT may involve directing particle beams toward the irradiation target at different angles and at different intensities to treat the target. In some implementations, the particle beam may be scanned—for example, moved—across layers of the irradiation target, with each layer being treated one or more times from the same or different angles. Movement across the irradiation target to implement scanning may be performed using the scanning magnet(s) described herein.

Figure 17:
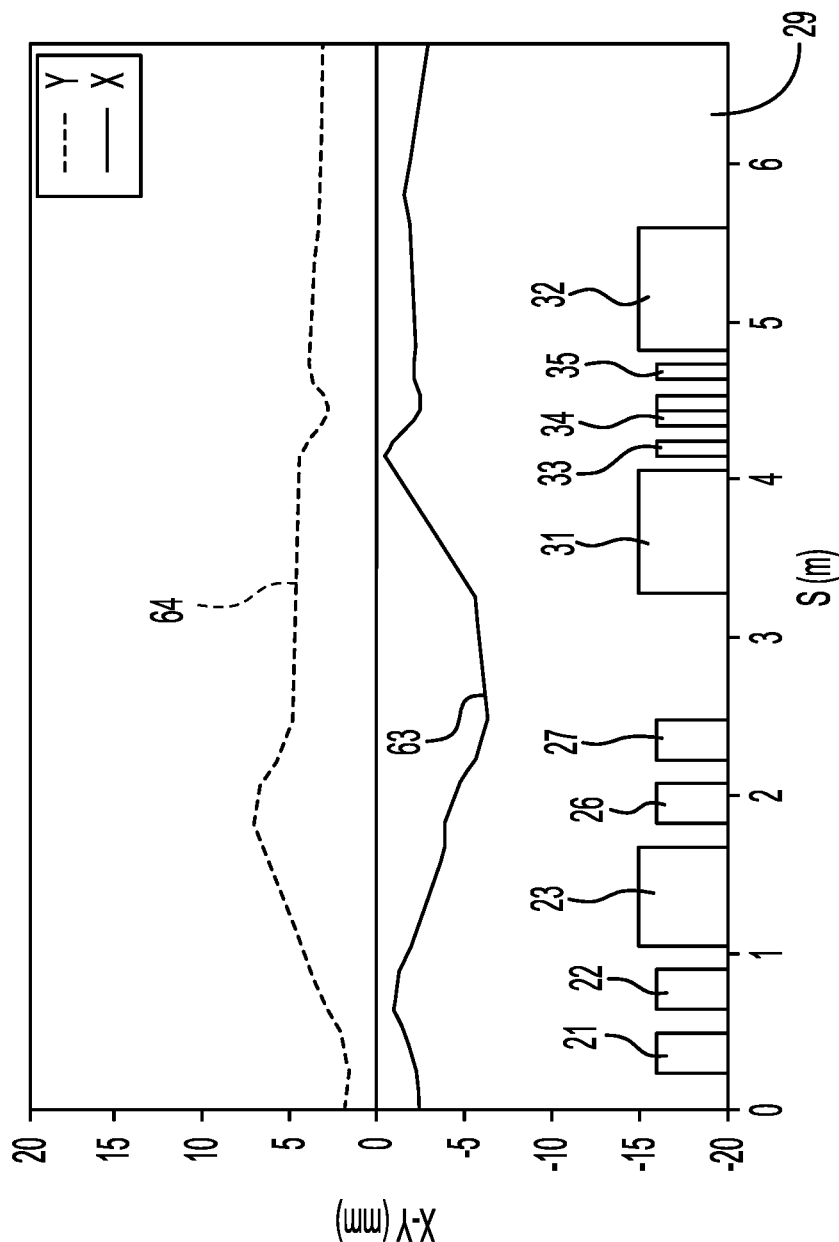
FIG. 17 is a graph showing example horizontal (x) and vertical (y) particle beam envelopes produced in the example gantry described herein.

FIG. 17 shows example horizontal (x) beam envelope 63 and vertical (y) beam envelope 64 (e.g., cross-sections) along the length 29 the compact gantry described herein. The x and y dimensions of the beam spot cross-section are determined for magnetic quadrupoles 21 and 22, magnetic dipole 23, magnetic quadrupoles 26 and 27, magnetic dipole 31, magnetic quadrupoles 33, 34, and 35, and magnetic dipole 32. Beam sizes are determined based on calculations of beam optics using measured beam parameters at the exit of particle accelerator 12 and the design parameters of all the beamline magnets. In some implementations, the beam spot radius at the isocenter (e.g., a treatment positions) is approximately 3 millimeters (mm) for both x and y. In some implementations, for 200 MeV to 230 MeV proton beams, magnetic fields at the magnetic dipoles in beamline structure 16 are no more than 4 T and the bending radius of the beam at each of the magnetic dipoles is approximately 0.6 meters. In some implementations, for 200 MeV to 230 MeV proton beams, magnetic fields at the magnetic dipoles in beamline structure 16 are at least 3 T, that is, 3 T or greater. As noted, the systems described herein are not limited to these parameter values and some implementations may have different dimensions, energies, and magnetic fields.

Figure 18:
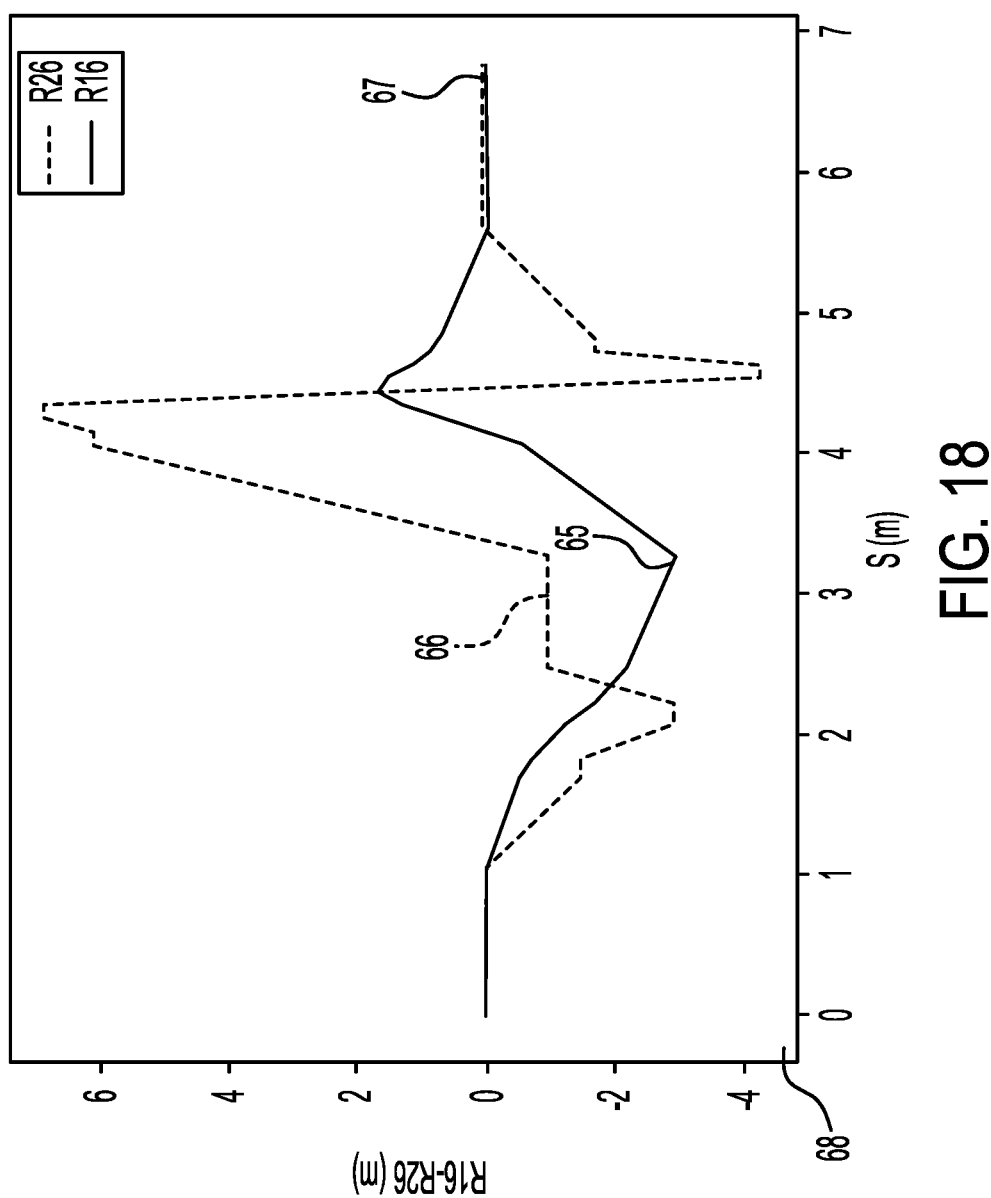
FIG. 18 is a graph showing an example achromatic lattice design for the beamline of the example gantry described herein.

Chromatic-aberration correction can occur in a beamline having dispersion, generated by inclusion of dipole magnets and multiple correctors in dispersive regions. The standard definition for an achromat is a beam transport line having zero values for spatial dispersion (R16) and angular dispersion (R26). Referring to FIG. 18, the magnetics in implementations of the compact gantry may be configured to be achromat—e.g., both R16 65 and R26 66 of the beam transfer matrix elements equal zero at the isocenter, which is at or near 0m along the beamline structure length 68 (the X-axis). Reducing or minimizing spatial and angular beam dispersions may be consequential to pencil beam scanning techniques implemented by the particle therapy systems described herein. In this regard, in some pencil beam scanning techniques, the cross-section of the particle beam is required to be substantially round at the isocenter. As such, the beam spot size in both x and y (FIG. 18) planes should be close at the isocenter 67. During beam scanning, changes to the beam shape and beam diameter over the entire scanning area should be reduced or minimized, otherwise, different beam particles of different energies may land at different locations in the bending plane. This may cause the beam shape and beam size to differ in another plane.

Figure 19:
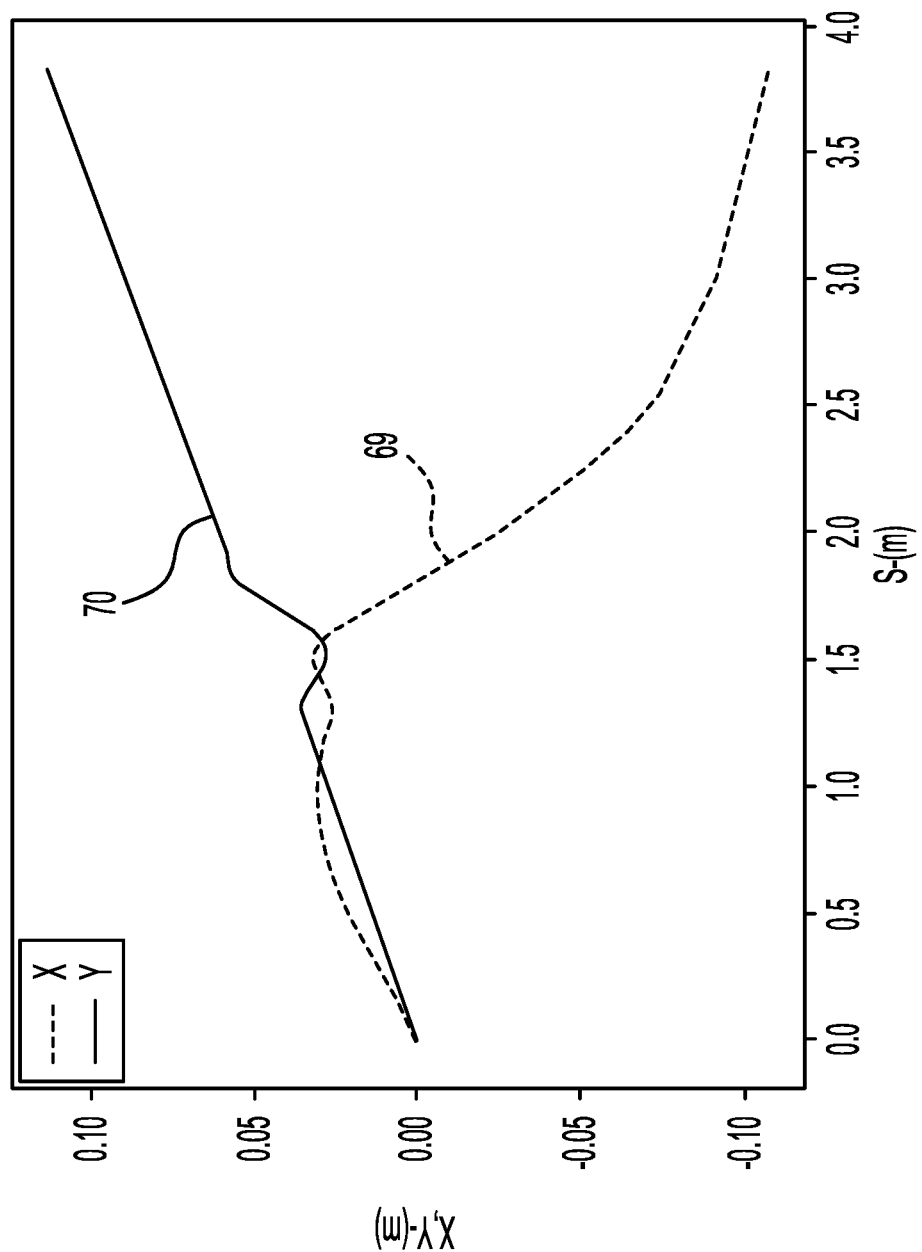
FIG. 19 is a graph showing results produced by scanning the particle beam in the horizontal (x) and vertical (y) planes using the example gantry described herein.

FIG. 19 shows examples of beam scans in the x dimension 69 and the y dimension 70. The firing of the scanning magnets allows the beam particle to be deflected to an angle proportional to the field strength of the scanning magnets. In the example of FIG. 19, a beam scanning range that fully covers a beam field area of 20 cm by 20 cm is shown with beam deflection angles of approximately ±20 milliradians (mrad) and ±30 mrad from the scanning magnets. In this example, the source-to-isocenter distance (SAD) (that is, the accelerator to isocenter distance) is approximately 4 meters. In some implementations, from the scanning magnet(s) to the exit of output channel 17, the beam bending angle can be as large as 110° to 170°.

Referring back to FIG. 1, in some implementations, an imaging system comprised of one or more imaging devices 99 may be mounted to support structure 15. Imaging may be performed before and/or during treatment to identify a target location within the patient and/or to control operation of the gantry and scanning in order to direct the particle beam to the irradiation target in the patient. The imaging system may include one or more of: a computerized tomography (CT) scanner, a two-dimensional (2D) X-ray device, a magnetic resonance imaging (MRI) device, a fan-beam CT scanner, a 2D camera, a three-dimensional (3D) camera, a surface imaging device, or a cone-beam CT scanner The imaging devices may be configured and controlled to rotate around gantry 14 or to rotate along with rotation of gantry 14. In some implementations, one or more nozzles, to which the beamline aligns and connects, are rotatable on a ring bearing located at the inner diameter of support structure 15. A variety of two-dimensional (2D) and/or three-dimensional (3D) imaging devices also may be mounted on the ring bearing and may be rotatable therewith. In some implementations, nozzles and imaging devices may be mounted to different internal circumferential tracks within the gantry. For example, nozzles may be rotatable around a circumferential track at a first radius of the support structure, and imaging devices may be rotatable around a different circumferential track at a second radius of the support structure that is different from the first radius. In some implementations, the gantry may include different rotatable inner rings, one of which mounts the nozzles for rotation and one of which mounts the imaging devices or systems for rotation.

In some implementations, two 2D imaging devices are mounted to support structure 15 in orthogonal planes to enable 2D image-guided radiation therapy (IGRT). IGRT includes the use of imaging during radiation treatment to improve the precision and accuracy of treatment delivery. IGRT may be used to treat tumors in areas of the body that move, such as the lungs. The 2D imaging devices can be rotated to enable cone-beam CT imaging, including simultaneously acquired dual energy imaging. The imaging devices may also, or alternatively, include an X-ray source and an image panel for cone-beam CT image acquisition or a fan-beam diagnostic quality CT imaging device. Alternatively, one plane may include a cone-beam CT imaging device and another plane may include a fan-beam diagnostic quality CT imaging device.

Figure 20:
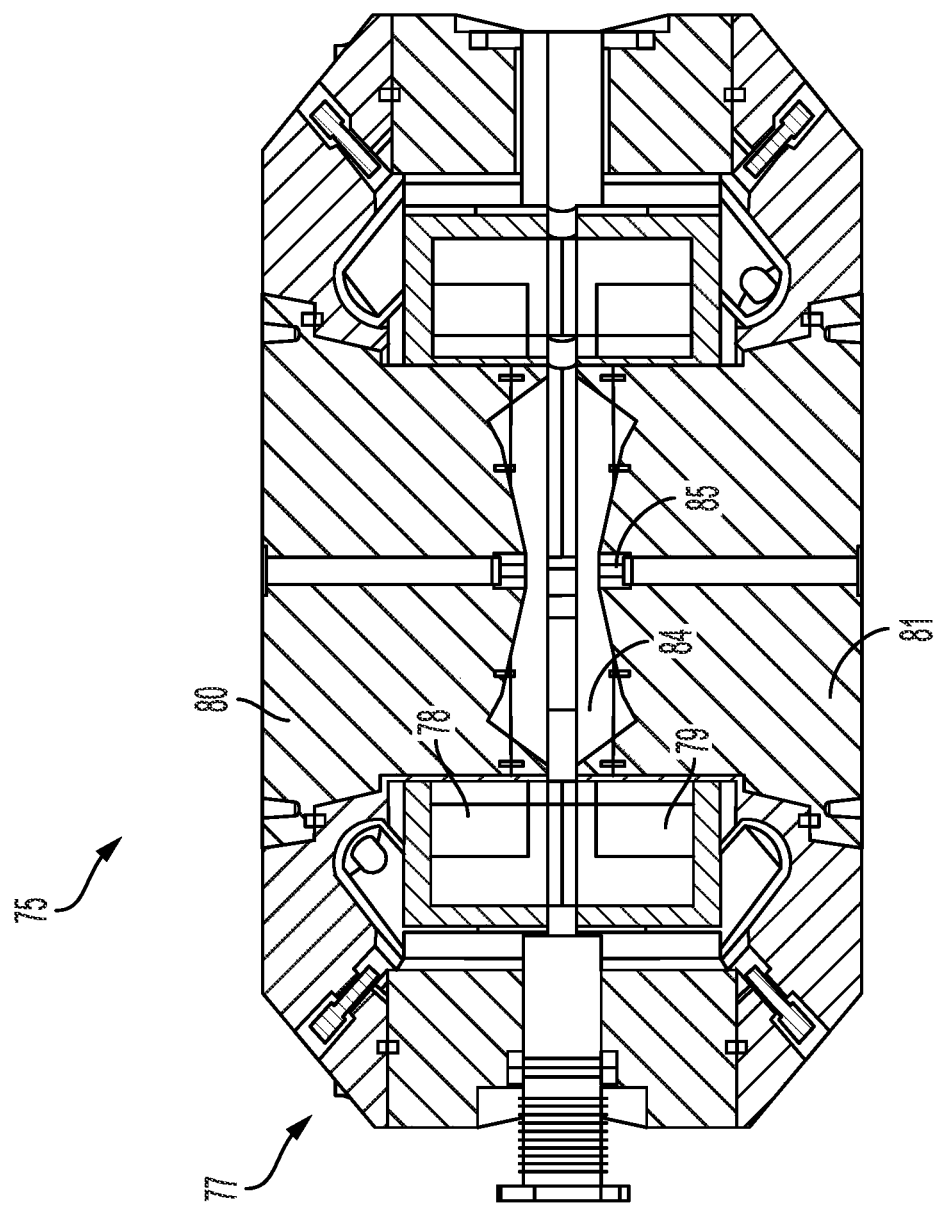
FIG. 20 is a cut-away, side view of components in an example particle accelerator that may be used with the particle therapy system described herein.

As described herein, an example proton therapy system scans a proton beam in three dimensions across an irradiation target in order to destroy malignant tissue. FIG. 20 shows a cross-section of components 75 of an example superconducting synchrocyclotron that may be used to provide a particle (e.g., a proton) beam in the proton therapy system. In this example, components 75 include a superconducting magnet 77. The superconducting magnet includes superconducting coils 78 and 79. The superconducting coils are formed of multiple integrated conductors, each of which includes superconducting strands—for example, four strands or six strands—wound around a center strand which may itself be superconducting or non-superconducting. Each of the superconducting coils 78, 79 is for conducting a current that generates a magnetic field (B). The magnetic yokes 80, 81 or smaller magnetic pole pieces shape that magnetic field in a cavity 84 in which particles are accelerated. In an example, a cryostat (not shown) uses liquid helium (He) to conductively cool each coil to low-temperature superconducting temperatures, e.g., around 4° Kelvin (K).

In some implementations, the particle accelerator includes a particle source 85, such as a Penning Ion Gauge—PIG source, to provide an ionized plasma column to cavity 84. Hydrogen gas, or a combination of hydrogen gas and a noble gas, is ionized to produce the plasma column. A voltage source provides a varying radio frequency (RF) voltage to cavity 84 to accelerate particles from the plasma column within the cavity. As noted, in an example, the particle accelerator is a synchrocyclotron. Accordingly, the RF voltage is swept across a range of frequencies to account for relativistic effects on the particles, such as increasing particle mass, when accelerating particles within the acceleration cavity. The RF voltage drives a dee plate contained within the cavity and has a frequency that is swept downward during the accelerating cycle to account for the increasing relativistic mass of the protons and the decreasing magnetic field. A dummy dee plate acts as a ground reference for the dee plate. The magnetic field produced by running current through the superconducting coils, together with sweeping RF voltage, causes particles from the plasma column to accelerate orbitally within the cavity and to increase in energy as a number of turns increases. The particles in the outermost orbit are directed to an extraction channel (not shown) and are output from the synchrocyclotron as a particle beam. In a synchrocyclotron, the particle beam is pulsed such that bunches of particles are output periodically.

The magnetic field in the cavity is shaped to cause particles to move orbitally within the cavity as described above. The example synchrocyclotron employs a magnetic field that is uniform in rotation angle and falls off in strength with increasing radius. In some implementations, the maximum magnetic field produced by the superconducting (main) coils may be within the range of 2.5 T to 20 T at a center of the cavity, which falls off with increasing radius. For example, the superconducting coils may be used in generating magnetic fields at, or that exceed, one or more of the following magnitudes: 2.5 T, 3.0 T, 3.1 T, 3.2 T, 3.3 T, 3.4 T, 3.5 T, 3.6 T, 3.7 T, 3.8 T, 3.9 T, 4.0 T, 4.1 T, 4.2 T, 4.3 T, 4.4 T, 4.5 T, 4.6 T, 4.7 T, 4.8 T, 4.9 T, 5.0 T, 5.1 T, 5.2 T, 5.3 T, 5.4 T, 5.5 T, 5.6 T, 5.7 T, 5.8 T, 5.9 T, 6.0 T, 6.1 T, 6.2 T, 6.3 T, 6.4 T, 6.5 T, 6.6 T, 6.7 T, 6.8 T, 6.9 T, 7.0 T, 7.1 T, 7.2 T, 7.3 T, 7.4 T, 7.5 T, 7.6 T, 7.7 T, 7.8 T, 7.9 T, 8.0 T, 8.1 T, 8.2 T, 8.3 T, 8.4 T, 8.5 T, 8.6 T, 8.7 T, 8.8 T, 8.9 T, 9.0 T, 9.1 T, 9.2 T, 9.3 T, 9.4 T, 9.5 T, 9.6 T, 9.7 T, 9.8 T, 9.9 T, 10.0 T, 10.1 T, 10.2 T, 10.3 T, 10.4 T, 10.5 T, 10.6 T, 10.7 T, 10.8 T, 10.9 T, 11.0 T, 11.1 T, 11.2 T, 11.3 T, 11.4 T, 11.5 T, 11.6 T, 11.7 T, 11.8 T, 11.9 T, 12.0 T, 12.1 T, 12.2 T, 12.3 T, 12.4 T, 12.5 T, 12.6 T, 12.7 T, 12.8 T, 12.9 T, 13.0 T, 13.1 T, 13.2 T, 13.3 T, 13.4 T, 13.5 T, 13.6 T, 13.7 T, 13.8 T, 13.9 T, 14.0 T, 14.1 T, 14.2 T, 14.3 T, 14.4 T, 14.5 T, 14.6 T, 14.7 T, 14.8 T, 14.9 T, 15.0 T, 15.1 T, 15.2 T, 15.3 T, 15.4 T, 15.5 T, 15.6 T, 15.7 T, 15.8 T, 15.9 T, 16.0 T, 16.1 T, 16.2 T, 16.3 T, 16.4 T, 16.5 T, 16.6 T, 16.7 T, 16.8 T, 16.9 T, 17.0 T, 17.1 T, 17.2 T, 17.3 T, 17.4 T, 17.5 T, 17.6 T, 17.7 T, 17.8 T, 17.9 T, 18.0 T, 18.1 T, 18.2 T, 18.3 T, 18.4 T, 18.5 T, 18.6 T, 18.7 T, 18.8 T, 18.9 T, 19.0 T, 19.1 T, 19.2 T, 19.3 T, 19.4 T, 19.5 T, 19.6 T, 19.7 T, 19.8 T, 19.9 T, 20.0 T, 20.1 T, 20.2 T, 20.3 T, 20.4 T, 20.5 T, 20.6 T, 20.7 T, 20.8 T, 20.9 T, or more. Furthermore, the superconducting coils may be used in generating magnetic fields that are outside the range of 2.5 T to 20 T or that are within the range of 3 T to 20 T but that are not specifically listed herein.

By generating a high magnetic field having a magnitude such as those described above, the bend radius of particles orbiting within cavity 84 can be reduced. As a result of the reduction in the bend radius, a greater number of particle orbits can be made within a given-sized cavity. So, the same number of orbits can be fit within a smaller cavity. Reducing the size of the cavity reduces the size of the particle accelerator in general, since a smaller cavity requires smaller magnetic yokes or pole pieces, among other components. In some implementations, the size or volume of the particle accelerator may be 4 m³ or less, 3 m³ or less, or 2 m³ or less.

In some implementations, such as the implementations shown in FIG. 20, the relatively large ferromagnetic magnetic yokes 80, 81 act as magnetic returns for stray magnetic fields produced by the superconducting coils. In some systems, a magnetic shield (not shown) surrounds the yokes. The return yokes and the shield together act to reduce stray magnetic fields, thereby reducing the possibility that stray magnetic fields will adversely affect the operation of the particle accelerator.

In some implementations, the return yokes and/or shield may be replaced by, or augmented by, an active return system. An example active return system includes one or more active return coils that conduct current in a direction opposite to current through the main superconducting coils. In some implementations, there is an active return coil for each superconducting main coil, e.g., two active return coils—one for each main superconducting coil. Each active return coil may also be a superconducting coil that surrounds the outside of a corresponding main superconducting coil concentrically. In some implementations, the active return coils may be or include non-superconducting coils. By using an active return system, the relatively large ferromagnetic magnetic yokes 80, 81 can be replaced with magnetic pole pieces that are smaller and lighter. Accordingly, the size and weight of the synchrocyclotron can be reduced further without sacrificing performance. An example of an active return system that may be used is described in U.S. Pat. No. 8,791,656 (Zwart) entitled "Active Return System". The content of U.S. Pat. No. 8,791,656, particularly the content related to the return coil configuration (e.g., FIGS. 2, 4, and 5 of U.S. Pat. No. 8,791,656 and the accompanying description), is incorporated herein by reference.

Another example of a particle accelerator that may be used in the particle therapy system herein is described in U.S. Pat. No. 8,975,836 (Bromberg) entitled "Ultra-Light Magnetically Shielded High-Current, Compact Cyclotron". The content of U.S. Pat. No. 8,975,836, particularly the content related to "cyclotron 11" or "iron-free cyclotron 11" of FIGS. 4, 17 and 18 of U.S. Pat. No. 8,975,836 and the accompanying description, is incorporated herein by reference.

In some implementations, the synchrocyclotron used in the proton therapy system described herein may be a variable-energy synchrocyclotron. In some implementations, a variable-energy synchrocyclotron is configured to vary the energy of the output particle beam by varying the magnetic field in which the particle beam is accelerated. For example, the current may be set to any one of multiple values to produce a corresponding magnetic field. For example, the current may be set to one of two values to produce the dual-energy particle accelerator described previously. In an example implementation, one or more sets of superconducting coils receives variable electrical current to produce a variable magnetic field in the cavity. In some examples, one set of coils receives a fixed electrical current, while one or more other sets of coils receives a variable current so that the total current received by the coil sets varies. In some implementations, all sets of coils are superconducting. In some implementations, some sets of coils, such as the set for the fixed electrical current, are superconducting, while other sets of coils, such as the one or more sets for the variable current, are non-superconducting (e.g., copper) coils.

Generally, in a variable-energy synchrocyclotron, the magnitude of the magnetic field is scalable with the magnitude of the electrical current. Adjusting the total electric current of the coils in a predetermined range can generate a magnetic field that varies in a corresponding, predetermined range. In some examples, a continuous adjustment of the electrical current can lead to a continuous variation of the magnetic field and a continuous variation of the output beam energy. Alternatively, when the electrical current applied to the coils is adjusted in a non-continuous, step-wise manner, the magnetic field and the output beam energy also varies accordingly in a non-continuous (step-wise) manner. The step-wise adjustment can produce the dual energies described previously. In some implementations, each step is between 10 MeV and 80 MeV in size. The scaling of the magnetic field to the current can allow the variation of the beam energy to be carried out relatively precisely, thus reducing the need for an energy degrader. An example of a variable-energy synchrocyclotron that may be used in the particle therapy systems described herein is described in U.S. Pat. No. 9,730,308 entitled "Particle Accelerator That Produces Charged Particles Having Variable Energies". The content U.S. Pat. No. 9,730,308 is incorporated herein by reference, particularly the content that enables operation of a synchrocyclotron at variable energies, including the content described in columns 5 through 7 of U.S. Pat. No. 9,730,308 and FIG. 13 and its accompanying description.

In implementations of the particle therapy system that use a variable-energy synchrocyclotron, controlling the energy of the particle beam to treat a portion of the irradiation target may be performed in accordance with the treatment plan by changing the energy of the particle beam output by the synchrocyclotron. In such implementations, an energy degrader may or may not be used. For example, controlling the energy of the particle beam may include setting the current in the synchrocyclotron main coils to one of multiple values, each which corresponds to a different energy at which the particle beam is output from the synchrocyclotron. An energy degrader may be used along with a variable-energy synchrocyclotron to provide additional changes in energy, for, example, between discrete energy levels provided by the synchrocyclotron.

The particle therapy system and its variations described herein may be used to apply ultra-high dose rates of radiation—so called, "FLASH" dose rates of radiation—to an irradiation target in a patient. In this regard, experimental results in radiation therapy have shown an improvement in the condition of healthy tissue subjected to radiation when the treatment dose is delivered at ultra-high (FLASH) dose rates. In an example, when delivering doses of radiation at 10 to 20 Gray (Gy) in pulses of less than 500 milliseconds (ms) reaching effective dose rates of 20 to 100 Gray-per-second (Gy/S), healthy tissue experiences less damage than when irradiated with the same dose over a longer time scale, while tumors are treated with similar effectiveness. A theory that may explain this "FLASH effect" is based on the fact that radiation damage to tissue is proportionate to oxygen supply in the tissue. In healthy tissue, the ultra-high dose rate radicalizes the oxygen only once, as opposed to dose applications that radicalize the oxygen multiple times over a longer timescale. This may lead to less damage in the healthy tissue using the ultra-high dose rate.

In some examples, as noted above, ultra-high dose rates of radiation may include doses of radiation that exceed 1 Gray-per-second for a duration of less than 500 ms. In some examples, ultra-high dose rates of radiation may include doses of radiation that exceed 1 Gray-per-second for a duration that is between 10 ms and 5 s. In some examples, ultra-high dose rates of radiation may include doses of radiation that exceed 1 Gray-per-second for a duration that is less than 5 s.

In some examples, ultra-high dose rates of radiation include doses of radiation that exceed one of the following doses for a duration of less than 500 ms: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second. In some examples, ultra-high dose rates of radiation include doses of radiation that exceed one of the following doses for a duration that is between 10 ms and 5 s: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second. In some examples, ultra-high dose rates of radiation include doses of radiation that exceed one of the following doses for a duration that is less than 5 s: 2 Gray-per-second, 3 Gray-per-second, 4 Gray-per-second, 5 Gray-per-second, 6 Gray-per-second, 7 Gray-per-second, 8 Gray-per-second, 9 Gray-per-second, 10 Gray-per-second, 11 Gray-per-second, 12 Gray-per-second, 13 Gray-per-second, 14 Gray-per-second, 15 Gray-per-second, 16 Gray-per-second, 17 Gray-per-second, 18 Gray-per-second, 19 Gray-per-second, 20 Gray-per-second, 30 Gray-per-second, 40 Gray-per-second, 50 Gray-per-second, 60 Gray-per-second, 70 Gray-per-second, 80 Gray-per-second, 90 Gray-per-second, or 100 Gray-per-second.

In some examples, ultra-high dose rates of radiation include doses of radiation that exceed one or more of the following doses for a duration of less than 500 ms, for a duration that is between 10 ms and 5 s, or for a duration that is less than 5 s: 100 Gray-per-second, 200 Gray-per-second, 300 Gray-per-second, 400 Gray-per-second, or 500 Gray-per-second.

In some examples, ultra-high dose rates of radiation include doses of radiation that are between 20 Gray-per-second and 100 Gray-per-second for a duration of less than 500 ms. In some examples, ultra-high dose rates of radiation include doses of radiation that are between 20 Gray-per-second and 100 Gray-per-second for a duration that is between 10 ms and 5 s. In some examples, ultra-high dose rates of radiation include doses of radiation that are between 20 Gray-per-second and 100 Gray-per-second for a duration that is less than 5 s. In some examples, ultra-high dose rate rates of radiation include doses of radiation that are between 40 Gray-per-second and 120 Gray-per-second for a time period such as less than 5 s. Other examples of the time period are those provided above.

In some implementations, the particle therapy systems may treat three-dimensional columns of the target using ultra-high dose rate radiation—the FLASH doses of radiation. These systems scale the ultra-high dose rate deliveries to targets using pencil beam scanning. In some examples, pencil beam scanning includes delivering a series of small beams of particle radiation that can each have a unique direction, energy, and charge. By combining doses from these individual beams, a three-dimensional target treatment volume may be treated with radiation. Furthermore, instead of organizing the treatment into layers at constant energies, the systems organize the treatment into columns defined by the direction of a stationary beam. The direction of the beam may be toward the surface of the target.

In some implementations, all or part of a column is treated before the particle beam is directed along another path through the irradiation target. In some implementations, a path through the target is all or part-way through the target. In an example, the particle beam may be directed along a path through a target and not deviate from that path. While directed along that path, the energy of the particle beam is changed. The particle beam does not move as its energy changes and, as a result, the particle beam treats all or a part of an interior portion of the target that extends along a length of the particle beam and along a width of the beam spot. The treatment is thus depth-wise along a longitudinal direction of the beam. For example, a portion of the target treated may extend from a spot of the beam at the surface of the target down through all or part of an interior of the target. The result is that the particle beam treats a three-dimensional columnar portion of the target using an ultra-high dose rate of radiation. In some examples, the particle beam may never again be directed along the same three-dimensional columnar portion more than once.

In some implementations, an irradiation target may be broken into micro-volumes. Although cubical micro-volumes may be used, the micro-volumes may have any appropriate shape, such as three-dimensional orthotopes, regular curved shapes, or irregular or amorphous shapes. In this example, each micro-volume is treated through delivery of FLASH radiation by column in the manner described herein. For example, column depths of a micro-volume may be treated with radiation by using energy degrader plates to change the beam energy or by controlling a variable-energy synchrocyclotron to change the beam energy. After an individual micro-volume has been treated, the next micro-volume is treated, and so forth until the entire irradiation target has been treated. Treatment of the micro-volumes may be in any appropriate order or sequence.

The particle therapy system described herein may deliver FLASH radiation by columns in the manner described in U.S. Patent Publication No. 2020/0298025 titled "Delivery Of Radiation By Column And Generating A Treatment Plan Therefor", the contents of which are incorporated herein by reference, particularly the contents relating to FIGS. 2, 11, 12 to 19, 33 to 43B thereof and the accompanying descriptions.

In some implementations, a particle accelerator other than a synchrocyclotron may be used in the particle therapy system described herein. For example, a cyclotron, a synchrotron, a linear accelerator, or the like may be substituted for the synchrocyclotron in the particle therapy systems described herein.

Figure 21:
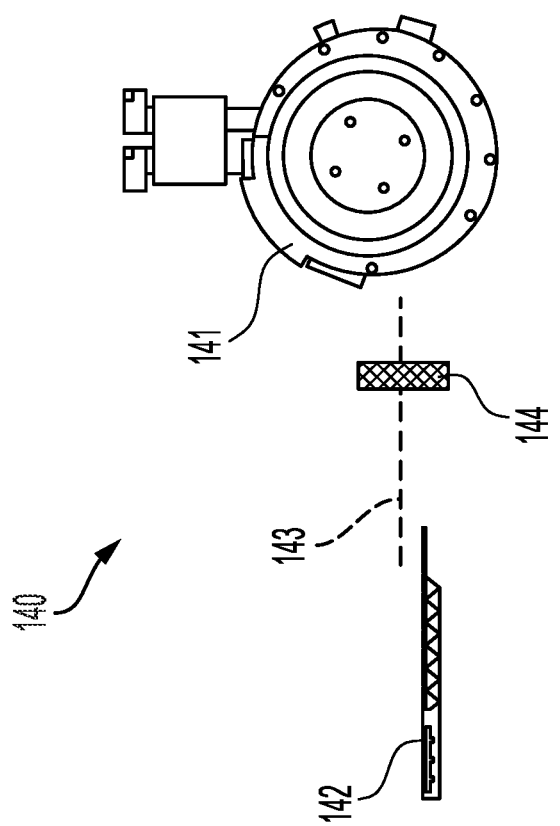
FIG. 21 is a side view of an example fixed-beam particle therapy system.

FIG. 21 shows an alternative implementation of a fixed-beam particle therapy system that includes a particle accelerator 141 and a treatment couch 142, which may be of the types described herein. In this implementation, particle accelerator 141 is stationary and is configured and controllable to output particles as a particle beam 143 in a single, fixed direction—for example, along a single directional vector. The particle beam may be monoenergetic and pulsed in the case of a synchrocyclotron. When other types of particle accelerators are used, the particle beam may be continuous rather than pulsed. As shown in the figure, in this example, there is no beamline structure between the particle accelerator and the patient.

One or more scanning magnets (not shown) may be located in the particle beam path between the particle accelerator and the treatment couch. The scanning magnets may be superconducting, non-superconducting, or a combination of superconducting and non-superconducting. The scanning magnets may be of the type shown in FIG. 5, in FIGS. 7 and 8, or a combination thereof. Control over scanning is achieved, in some implementations, by varying current through one or both sets of coils to thereby vary the magnetic field(s) produced thereby. By varying the magnetic field(s) appropriately, the particle beam can be moved in the X and/or Y dimension across the irradiation target.

An energy degrader 144 having a configuration as described herein is in the particle beam path between the treatment couch and the scanning magnet. The particle beam, in this example, is monoenergetic. Consequently, changes in the energy of the particle beam may be implemented solely by changing the configuration of the energy degrader. For example, plates or wedges may be moved to change the thickness of material in the path of the particle beam and, thus the energy of the particle beam.

A collimator (not shown) having a configuration as described herein may be in the particle beam path between the energy degrader and the treatment couch. The collimator is used as described herein to block portions of the particle beam from reaching non-target tissue in a patient. The collimator, the energy degrader, and the scanning magnets may be included in an output device, such as a nozzle, that may be mounted to a structure, such as a wall. The nozzle does not move relative to the particle accelerator or the treatment couch—although components of the devices contained therein may move during operation.

During operation, the treatment couch moves—for example, in three, four, five, or six degrees of freedom—relative to the particle beam or relative to the nozzle. The treatment couch may also be reclined to reach a treatment position. Accordingly, rather than moving the particle accelerator or the nozzle, the treatment couch moves the patient into a position for treatment and then the particle accelerator and devices in the nozzle are controlled to treat the patient in that position. The patient then may be repositioned to treat an irradiation target from a different position or angle.

In some implementations, the scanning magnet(s) may be replaced with a scattering foil and the energy degrader may be a range modulator. In implementations such as this, the scattering foil scatters the particle beam across a treatment area and the depth to which the scattered beam is applied is controlled by the range modulator. The configurable collimator may remain in place to trim edges of the scattered beam.

Operation of the example proton therapy systems described herein, and operation of all or some component thereof, can be controlled, at least in part, using a control system 192 (FIG. 1) configured to execute one or more computer program products, e.g., one or more computer programs tangibly embodied in one or more non-transitory machine-readable media, for execution by, or to control the operation of, one or more data processing apparatus, e.g., a programmable processor, a computer, multiple computers, and/or programmable logic components.

All or part of the systems described in this specification and their various modifications may be configured or controlled at least in part by one or more computers such as the control system using one or more computer programs tangibly embodied in one or more information carriers, such as in one or more non-transitory machine-readable storage media. A computer program can be written in any form of programming language, including compiled or interpreted languages, and it can be deployed in any form, including as a stand-alone program or as a module, part, subroutine, or other unit suitable for use in a computing environment. A computer program can be deployed to be executed on one computer or on multiple computers at one site or distributed across multiple sites and interconnected by a network.

Actions associated with configuring or controlling the systems described herein can be performed by one or more programmable processors executing one or more computer programs to control or to perform all or some of the operations described herein. All or part of the systems and processes can be configured or controlled by special purpose logic circuitry, such as, an FPGA (field programmable gate array) and/or an ASIC (application-specified integrated circuit) or embedded microprocessor(s) localized to the instrument hardware.

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, such as magnetic, magneto-optical disks, or optical disks. Non-transitory machine-readable storage media suitable for embodying computer program instructions and data include all forms of non-volatile storage area, including by way of example, semiconductor storage area devices, such as EPROM (erasable programmable read-only memory), EEPROM (electrically erasable programmable read-only memory), and flash storage area devices; magnetic disks, such as internal hard disks or removable disks; magneto-optical disks; and CD-ROM (compact disc read-only memory) and DVD-ROM (digital versatile disc read-only memory).

Elements of different implementations described may be combined to form other implementations not specifically set forth previously. Elements may be left out of the systems described previously without adversely affecting their operation or the operation of the system in general. Furthermore, various separate elements may be combined into one or more individual elements to perform the functions described in this specification.

Other implementations not specifically described in this specification are also within the scope of the following claims.

What is claimed is:

1. A particle therapy system comprising:
   a gantry comprising a beamline structure configured to direct a particle beam that is monoenergetic from an output of a particle accelerator towards an irradiation target, the beamline structure comprising magnetic bending elements to bend the particle beam along a length of the beamline structure; and
   an energy degrader downstream of the beamline structure relative to the particle accelerator, the energy degrader being configured and controllable to change an energy of the particle beam prior to at least part of the particle beam reaching the irradiation target;
   wherein the beamline structure has an efficiency of 10% or more; and
   wherein the efficiency of 10% or more includes 10% or more of particles output from the particle accelerator being output from the beamline structure.

2. The particle therapy system of claim 1, wherein the energy degrader is the sole mechanism by which to actively control the change in energy of the particle beam after the particle beam is output by the particle accelerator and prior to the particle beam reaching the irradiation target.

3. The particle therapy system of claim 1, wherein the beamline structure is configured so as not to actively control the energy of the particle beam after the particle beam is output by the particle accelerator and prior to the particle beam reaching the energy degrader.

4. The particle therapy system of claim 1, wherein the magnetic bending elements comprise a magnet having a magnetic field of 2.5 Tesla (T) or more; or
   wherein the magnetic bending elements comprise a magnet having a magnetic field of 3 Tesla (T) or more.

5. The particle therapy system of claim 1, wherein the gantry comprises a support structure configured to move part of the beamline structure in a circular path around the irradiation target; and
   wherein the support structure has a dimension that is 6 meters or less.

6. The particle therapy system of claim 5, wherein the dimension is a diameter of the support structure.

7. The particle therapy system of claim 1, wherein a length of the beamline structure is 6 meters (m) or less; or
   wherein a length of the beamline structure is 5 meters (m) or less.

8. The particle therapy system of claim 1, wherein an energy of the particle beam does not vary within the beamline structure by more than 1%.

9. The particle therapy system of claim 1, wherein a distance between an output of the beamline structure and an isocenter containing the irradiation target is 1.5 meters (m) or less.

10. The particle therapy system of claim 1, further comprising:
   a scanning system comprising one or more scanning magnets to move the particle beam in at least two dimensions across at least part of a beam field that covers at least part of the irradiation target.

11. The particle therapy system of claim 10, wherein at least one of the scanning magnets comprises a superconducting magnet.

12. The particle therapy system of claim 10, wherein at least one of the scanning magnets is located downstream of the beamline structure relative to the particle accelerator.

13. The particle therapy system of claim 10, wherein at least one of the scanning magnets is located within the beamline structure.

14. The particle therapy system of claim 10, wherein the one or more scanning magnets comprise a first scanning magnet located within the beamline structure and a second scanning magnet located downstream of the first scanning magnet relative to the particle accelerator, the first scanning magnet being separate from the second scanning magnet.

15. The particle therapy system of claim 14, wherein the first scanning magnet is configured to move the particle beam across the at least part of the beam field in the at least two dimensions; and
   wherein the second scanning magnet is configured to move the particle beam across the at least part of the beam field in the at least two dimensions.

16. The particle therapy system of claim 14, wherein the first scanning magnet is configured to move the particle beam across the at least part of the beam field a first dimension only; and
   wherein the second scanning magnet is configured to move the particle beam across the at least part of the beam field in a second dimension only, the second dimension being different from the first dimension.

17. The particle therapy system of claim 14, wherein the first scanning magnet is located among magnetics included in the beamline structure and the second scanning magnet is located in a particle beam output device downstream of the beamline structure, the particle beam output device comprising a nozzle.

18. The particle therapy system of claim 14, wherein the first scanning magnet is located in the beamline structure and the second scanning magnet is located in the beamline structure.

19. The particle therapy system of claim 1, wherein the beamline structure comprises an output channel comprising magnetic dipoles arranged in series to bend the particle beam by at least 90°.

20. The particle therapy system of claim 19, wherein the magnetic dipoles comprise at least a first magnetic dipole and a second magnetic dipole, the first magnetic dipole and the second magnetic dipole being between the first scanning magnet and the second scanning magnet.

21. The particle therapy system of claim 1, wherein the beamline structure comprises an output channel configured to bend the particle beam by at least 90° towards an irradiation target in a presence of a magnetic field of at least 3 Tesla (T); and
   wherein the beamline structure comprises magnetic dipoles to bend the particle beam and two or more magnetic quadrupoles or magnetic sextupoles arranged among the magnetic dipoles along a length of the beamline structure to focus the particle beam.

22. The particle therapy system of claim 1, further comprising:
   the particle accelerator, the particle accelerator being a compact particle accelerator.

23. The particle therapy system of claim 1, wherein the beamline structure has a length of 6 meters or less.

24. A particle therapy system comprising:
   a particle accelerator configured to output particles as a particle beam that is monoenergetic;
   a gantry comprising:
      an output channel comprising magnetics configured to bend the particle beam by at least 90° in a presence of a magnetic field of at least 2.5 Tesla (T);
      a support structure on which the output channel is mounted for movement at least part-way around an irradiation target; and
      a conduit to direct the particle beam to the output channel;
   an energy degrader that is downstream of the output channel relative to the particle accelerator; and
   a scanning system comprising two or more scanning magnets, at least one of the scanning magnets being upstream of at least some magnetics in the output channel relative to the particle accelerator, the two or more scanning magnets being separated by air or other magnetics and being configured to move the particle beam across at least part of a beam field in at least two dimensions.

25. The particle therapy system of claim 24, wherein the energy degrader is the sole mechanism by which to actively control a change in energy of the particle beam after the particle beam is output by the particle accelerator and prior to the particle beam reaching the irradiation target.

26. The particle therapy system of claim 24, wherein the gantry is configured so as not to actively control an energy of the particle beam after the particle beam is output by the particle accelerator and prior to the particle beam reaching the energy degrader.

27. The particle therapy system of claim 24, wherein the conduit and the output channel together having an efficiency of 10% or more; and
   wherein the efficiency of 10% or more includes 10% or more of the particles output from the particle accelerator being output from the output channel.

28. The particle therapy system of claim 24, wherein the gantry is 5 meters or less in length measured from the particle accelerator.

29. The particle therapy system of claim 24, wherein the magnetics comprise:
    a first magnetic dipole to bend the particle beam toward an irradiation target; and
    a second magnetic dipole upstream of the first magnetic dipole relative to the particle accelerator, the second magnetic dipole being configured to bend the particle beam toward the first magnetic dipole.

30. The particle therapy system of claim 24, wherein the gantry and the particle accelerator are in a same space and not separated by shielding external to the particle accelerator that exceeds 30 centimeters in thickness.

31. The particle therapy system of claim 24 having a footprint of 75 square meters or less.

32. The particle therapy system of claim 24, wherein the particle accelerator comprises a synchrocyclotron; and
    wherein the particle therapy system is sized to fit within a vault designed for a linear accelerator (LINAC).

* * * * *